US011857543B2

(12) United States Patent
Shalwitz et al.

(10) Patent No.: US 11,857,543 B2
(45) Date of Patent: *Jan. 2, 2024

(54) COMPOSITIONS AND METHODS FOR TREATING ANEMIA

(71) Applicant: Akebia Therapeutics, Inc., Cambridge, MA (US)

(72) Inventors: Robert Shalwitz, Bexley, OH (US); Charlotte Hartman, Carmel, IN (US); Akshay Buch, West Chester, OH (US); Isaiah Shalwitz, Columbus, OH (US); John Janusz, West Chester, OH (US); Joseph Gardner, Cincinnati, OH (US)

(73) Assignee: Akebia Therapeutics, Inc., Cambridge, MA (US)

( * ) Notice: Subject to any disclaimer, the term of this patent is extended or adjusted under 35 U.S.C. 154(b) by 5 days.

This patent is subject to a terminal disclaimer.

(21) Appl. No.: 14/897,849

(22) PCT Filed: Jun. 4, 2014

(86) PCT No.: PCT/US2014/040889
§ 371 (c)(1),
(2) Date: Dec. 11, 2015

(87) PCT Pub. No.: WO2014/200773
PCT Pub. Date: Dec. 18, 2014

(65) Prior Publication Data
US 2016/0143891 A1    May 26, 2016

Related U.S. Application Data

(60) Provisional application No. 61/912,185, filed on Dec. 5, 2013, provisional application No. 61/898,885, filed on Nov. 1, 2013, provisional application No. 61/898,890, filed on Nov. 1, 2013, provisional application No. 61/889,478, filed on Oct. 10, 2013, provisional application No. 61/834,808, filed on Jun. 13, 2013.

(51) Int. Cl.
*A61K 31/44* (2006.01)
*A61K 31/4412* (2006.01)
*A61K 9/00* (2006.01)
*A61K 33/26* (2006.01)
*A61K 38/18* (2006.01)

(52) U.S. Cl.
CPC ........... *A61K 31/44* (2013.01); *A61K 9/0053* (2013.01); *A61K 31/4412* (2013.01); *A61K 33/26* (2013.01); *A61K 38/1816* (2013.01)

(58) Field of Classification Search
CPC .... A61K 31/44; A61K 31/4412; A61K 33/26; A61K 38/1816; A61K 9/0053; A61K 9/2054; A61K 9/2059; A61K 9/2077; A61P 7/06; A61P 13/12; A61P 43/00
See application file for complete search history.

(56) References Cited

U.S. PATENT DOCUMENTS

| | | |
|---|---|---|
| 3,655,679 A | 4/1972 | Tsung-ying et al. |
| 3,703,582 A | 11/1972 | Shen et al. |
| 3,894,920 A | 7/1975 | Kondo et al. |
| 4,016,287 A | 4/1977 | Eberhardt et al. |
| 4,764,522 A | 8/1988 | Imhof et al. |
| 5,397,799 A | 3/1995 | Kress et al. |
| 5,405,613 A | 4/1995 | Rowland et al. |
| 5,607,954 A | 3/1997 | Weidmann et al. |
| 5,610,172 A | 3/1997 | Weidmann et al. |
| 5,620,995 A | 4/1997 | Wiedmann et al. |
| 5,620,996 A | 4/1997 | Weidmann et al. |
| 5,658,933 A | 8/1997 | Wiedmann et al. |
| 5,719,164 A | 2/1998 | Weidmann et al. |
| 5,726,305 A | 3/1998 | Weidmann et al. |
| 6,020,350 A | 2/2000 | Wiedmann et al. |
| 6,093,730 A | 7/2000 | Weidmann et al. |
| 6,159,379 A | 12/2000 | Means et al. |
| 6,420,427 B1 | 7/2002 | Takahashi et al. |
| 6,566,088 B1 | 5/2003 | McKnight et al. |
| 6,589,758 B1 | 7/2003 | Zhu |
| 7,183,287 B2 | 2/2007 | Durley |
| 7,588,924 B2 | 9/2009 | Evdokimov et al. |
| 7,811,595 B2 | 10/2010 | Kawamoto et al. |
| 8,050,873 B2 | 11/2011 | Evdokimov et al. |
| 8,124,582 B2 | 2/2012 | Guenzler-Pukall et al. |
| 8,323,671 B2 | 12/2012 | Wu et al. |
| 8,343,952 B2 | 1/2013 | Wu et al. |

(Continued)

FOREIGN PATENT DOCUMENTS

| | | |
|---|---|---|
| CA | 2098158 | 6/1993 |
| CA | 2253282 | 11/1997 |

(Continued)

OTHER PUBLICATIONS

Beuck, Hypoxia-inducible factor stabilizers, Drug Test. Analysis p. 830, Feb. 24, 2012.*
Wikipedia, Vadadustat—AKB-6548 , Jun. 5, 2019.*
Robert Shalwitz, J. Am Soc Nephrol 23, Oct. 30-Nov 4, p. 56A (Year: 2012).*
Akebia 2011, AKB-6548, Nov. 2011.*
Clinical Trials.Gov: Archive: NCT01235936 Nn Aug. 30, 2012 [online]. U.S. National Institute of Health. Aug. 30, 2012 [retrieved on Dec. 1, 2014]. Retrieved from the Internet: <URL: http://clinicaltrials.gov/archive/NCT01235936/2012_09_30>; pp. 1-3.
Akebia Closes $41 Million Series C [online]. Triathlon Medical Ventures. Jun. 4, 2013 [ retrieved on Dec. 1, 2014]. Retrieved from the internet <URL: http://www.tmvp.com/news_Akebia_06042013.html>; pp. 1-2.

(Continued)

Primary Examiner — David J Blanchard
Assistant Examiner — Thurman Wheeler
(74) Attorney, Agent, or Firm — Proskauer Rose LLP

(57) ABSTRACT

Provided herein are specific doses of, and dosing regimens for, using a HIF prolyl hydroxylase inhibitor in treating or preventing anemia, such as anemia secondary to or associated with chronic kidney disease, anemia associated with or resulting from chemotherapy, or anemia associated with AIDS.

30 Claims, 6 Drawing Sheets
Specification includes a Sequence Listing.

(56) References Cited

U.S. PATENT DOCUMENTS

| | | |
|---|---|---|
| 8,512,972 B2 | 8/2013 | Evdokimov et al. |
| 8,530,404 B2 | 9/2013 | Seeley et al. |
| 8,598,210 B2 | 12/2013 | Kawamoto et al. |
| 8,722,895 B2 | 5/2014 | Kawamoto et al. |
| 8,865,748 B2 | 10/2014 | Shalwitz et al. |
| 8,940,773 B2 | 1/2015 | Kawamoto et al. |
| 9,145,366 B2 | 9/2015 | Lanthier et al. |
| 9,598,370 B2 | 3/2017 | Kawamoto et al. |
| 9,701,636 B2 | 7/2017 | Copp et al. |
| 9,776,969 B2 | 10/2017 | Lanthier et al. |
| 9,987,262 B2 | 6/2018 | Copp et al. |
| 10,149,842 B2 | 12/2018 | Copp et al. |
| 10,246,416 B2 | 4/2019 | Lanthier et al. |
| 10,596,158 B2 | 3/2020 | Copp et al. |
| 10,729,681 B2 | 8/2020 | Kawamoto et al. |
| 10,738,010 B2 | 8/2020 | Lanthier et al. |
| 2002/0049161 A1 | 4/2002 | Lehmann |
| 2002/0192737 A1 | 12/2002 | Kaelin, Jr. et al. |
| 2003/0153503 A1* | 8/2003 | Klaus ............... A61K 31/00 514/1 |
| 2003/0176317 A1 | 9/2003 | Guenzler-Pukall et al. |
| 2004/0235082 A1 | 11/2004 | Fourney et al. |
| 2004/0254215 A1 | 12/2004 | Arend et al. |
| 2006/0142389 A1 | 6/2006 | Aurell et al. |
| 2006/0276477 A1 | 12/2006 | Klaus et al. |
| 2007/0154482 A1 | 7/2007 | Sukhatme et al. |
| 2007/0203174 A1 | 8/2007 | Klimko et al. |
| 2007/0213335 A1 | 9/2007 | Fitch et al. |
| 2007/0299086 A1 | 12/2007 | Kawamoto |
| 2008/0124740 A1 | 5/2008 | Evkokimov et al. |
| 2008/0213404 A1 | 9/2008 | Johnson et al. |
| 2009/0023666 A1 | 1/2009 | Gardiner et al. |
| 2009/0082357 A1 | 3/2009 | Fitch et al. |
| 2010/0021423 A1 | 1/2010 | Brameld et al. |
| 2011/0077267 A1 | 3/2011 | Mitani et al. |
| 2011/0305776 A1 | 12/2011 | Ho et al. |
| 2012/0282627 A1 | 11/2012 | Evdokimov et al. |
| 2012/0309977 A1 | 12/2012 | Lanthier et al. |
| 2012/0316204 A1 | 12/2012 | Shalwitz et al. |
| 2012/0329836 A1 | 12/2012 | Marsh et al. |
| 2013/0022974 A1 | 1/2013 | Chinnaiyan et al. |
| 2014/0045899 A1 | 2/2014 | Kawamoto et al. |
| 2014/0057892 A1 | 2/2014 | Kawamoto et al. |
| 2015/0119425 A1 | 4/2015 | Kawamoto et al. |
| 2015/0141467 A1 | 5/2015 | Copp et al. |
| 2015/0361043 A1 | 12/2015 | Lanthier et al. |
| 2016/0009648 A1 | 1/2016 | Kawamoto et al. |
| 2016/0199434 A1 | 7/2016 | Eubank et al. |
| 2016/0214939 A1 | 7/2016 | Hanselman |
| 2016/0339005 A1 | 11/2016 | Shalwitz et al. |
| 2017/0189387 A1 | 7/2017 | Kawamoto et al. |
| 2017/0362178 A1 | 12/2017 | Lanthier |
| 2018/0065933 A1 | 3/2018 | Hanselmann et al. |
| 2018/0092892 A1 | 4/2018 | Smith et al. |
| 2021/0206721 A1* | 7/2021 | Ranjan ............... C07D 213/81 |

FOREIGN PATENT DOCUMENTS

| | | |
|---|---|---|
| CN | 101506149 A | 8/2009 |
| EP | 0650960 | 5/1995 |
| EP | 0650961 | 5/1995 |
| EP | 2044005 | 10/2010 |
| EP | 1738751 B1 | 5/2011 |
| EP | 2455381 | 5/2012 |
| ES | 8800158 A1 | 11/1987 |
| GB | 2163746 | 3/1986 |
| GB | 2444904 | 6/2008 |
| JP | S6160657 | 3/1986 |
| JP | H09221476 | 8/1997 |
| JP | AH11512414 | 10/1999 |
| JP | 2001-48786 | 2/2001 |
| JP | 2007-194072 | 11/2006 |
| JP | 2010-527378 | 11/2009 |
| KR | 10-2010-0020893 A | 2/2010 |
| WO | WO 1996/022021 | 7/1996 |
| WO | WO 1997/041103 | 11/1997 |
| WO | WO 1997/044333 | 11/1997 |
| WO | WO-99/55372 A1 | 11/1999 |
| WO | WO 1999/048870 | 11/1999 |
| WO | WO 1999/063970 | 12/1999 |
| WO | WO 2002/074980 | 9/2002 |
| WO | WO 2002/074981 | 9/2002 |
| WO | WO 2002/083688 | 10/2002 |
| WO | WO 2003/028663 | 4/2003 |
| WO | WO 2003/032972 | 4/2003 |
| WO | WO 2003/049686 | 6/2003 |
| WO | WO 2003/053997 | 7/2003 |
| WO | WO 2003/097040 | 11/2003 |
| WO | WO 2004/019868 | 3/2004 |
| WO | WO 2004/035812 | 4/2004 |
| WO | WO 2004/048383 | 6/2004 |
| WO | WO 2004/108121 | 12/2004 |
| WO | WO 2005/007192 | 1/2005 |
| WO | WO 2005/115984 | 12/2005 |
| WO | WO 2005/118836 | 12/2005 |
| WO | WO 2006/019831 | 2/2006 |
| WO | WO 2006/030977 | 3/2006 |
| WO | WO 2006/114213 | 11/2006 |
| WO | 2007031933 A2 | 3/2007 |
| WO | WO 2007/047194 | 4/2007 |
| WO | WO 2007/070359 | 6/2007 |
| WO | WO 2007/082899 | 7/2007 |
| WO | WO 2007/084667 | 7/2007 |
| WO | WO 2007/088571 | 8/2007 |
| WO | WO 2007/103905 | 9/2007 |
| WO | WO 2007/136990 | 11/2007 |
| WO | WO 2007/150011 | 12/2007 |
| WO | WO 2008/002576 | 1/2008 |
| WO | WO 2008043167 A1 | 4/2008 |
| WO | WO 2008/089051 | 7/2008 |
| WO | WO 2008/089052 | 7/2008 |
| WO | WO 2009/020119 | 8/2008 |
| WO | WO-2008/125388 A1 | 10/2008 |
| WO | WO 2008/130508 | 10/2008 |
| WO | WO 2008/130527 | 10/2008 |
| WO | WO 2008/137060 | 11/2008 |
| WO | WO 2008/141731 | 11/2008 |
| WO | WO 2008/144266 | 11/2008 |
| WO | WO 2009/019656 | 2/2009 |
| WO | WO 2009/035534 | 3/2009 |
| WO | WO 2009/037570 | 3/2009 |
| WO | WO 2009/039321 | 3/2009 |
| WO | WO 2009/039323 | 3/2009 |
| WO | WO 2007/038571 | 4/2009 |
| WO | WO 2009/043093 | 4/2009 |
| WO | WO 2009/049112 | 4/2009 |
| WO | WO 2009/067790 | 4/2009 |
| WO | WO 2009/070644 | 6/2009 |
| WO | WO 2009/073497 | 6/2009 |
| WO | WO 2009/073669 | 6/2009 |
| WO | WO 2009/086044 | 7/2009 |
| WO | WO 2009/086592 | 7/2009 |
| WO | WO 2009/089547 | 7/2009 |
| WO | WO 2009/111337 | 9/2009 |
| WO | WO 2010/029577 | 3/2010 |
| WO | WO 2010/113942 | 10/2010 |
| WO | WO-2010/114801 A1 | 10/2010 |
| WO | WO 2011/057112 | 11/2010 |
| WO | WO-2012/097331 A1 | 7/2012 |
| WO | WO 2012/170377 | 12/2012 |
| WO | WO 2012/170439 | 12/2012 |
| WO | WO 2012/170442 | 12/2012 |
| WO | WO 2013/013609 | 1/2013 |
| WO | WO 2014/168986 | 10/2014 |
| WO | WO 2014/200773 | 12/2014 |
| WO | WO 2015/023967 | 4/2015 |
| WO | WO 2015/073779 | 5/2015 |
| WO | WO 2015/112831 | 7/2015 |
| WO | WO 2016/118858 | 7/2016 |
| WO | WO 2016/153996 | 9/2016 |
| WO | WO 2016/161094 | 10/2016 |

(56) References Cited

FOREIGN PATENT DOCUMENTS

| WO | WO 2006/138511 | 12/2016 |
|---|---|---|
| WO | WO 2019/028150 A1 | 2/2019 |
| WO | WO 2020/072645 A1 | 4/2020 |

OTHER PUBLICATIONS

Stohlawetz, PJ et al., "Effects of Eryhtropoietin on Platelet Reactivity and Thrombopoiesis in Humans," Blood. 2000, vol. 95, No. 9; pp. 2983-2989.
Pasqualetti, P. et al., "Circadian Rhythm of Serum Erythropoietin in Myelodysplastic Syndromes," European Review for Medical and Pharmacological Sciences. 2000, vol. 4; pp. 111-115.
"Hippuric acid sodium salt", Science Lab.com: Chemicals & Laboratory Equipment; retrieved from the internet at <http://web.archive.org/web/20041107121553/http://www.sciencelab.com/page/S/PVAR/10415/SLH2620> on Mar. 11, 2010.
"Standards of Medical Care in Diabetes—2006", 2006, Diabetes Care, 29: s4-s42.
Acker et al., 2005, "Genetic evidence for a tumor suppressor role of HIF-2α", Cancer Cell, 8:131-141.
Alesso et al., 2003, "Improving resins for solid phase synthesis: incorporation of 1-[2-(2-methoxyethoxy) ethoxy]4-vinyl-benzene" Tetrahedron: 59: 7163-7169.
Altschul et al., 1997, "Gapped BLAST and PSI-BLAST: A New Generation of Protein Database Search Programs," Nucleic Acids Res., 25(27): 3389-3402.
Anderson et al., 1979, "Antileukemic Activity of Derivatives of 1,2-Dimethyl-3,4-bis(hydroxymethyl)-5-phenylpyrrole Bis(N-methylcarbamate)", J. Med. Chem., 22(8): 977-980.
Anderson et al., 2012, "Practical process research and development: a guide for organic chemists", p. 331.
Annex et al., 2005, "Growth Factor-Induced Therapeutic Angiogenesis in the Heart: Protein Therapy," Cardiovascular Research, 65(3): 649-655.
Ardelt et al., 2005, "Estradiol Regulates Angiopoietin-1 mRNA Expression Through Estrogen Receptor-α in a Rodent Experimental Stroke Model," Stroke, 36: 337-341.
Auerbach et al., 2003, "Angiogenesis Assays: A Critical Overview," Clinical Chemistry, 49: 32-40.
Barany et al., 1987, "Solid-phase Peptide Synthesis: A Silver Anniversary Report," Int. J. Peptide Protein Res., 30( 6): 705-739.
Bartlett et al., Apr. 1989, "Caveat: A Program to Facilitate the Structure-derived Design of Biologically Active Molecules", Molecular Recognition in Chemical and Biological Problems, Special Pub., Royal Chem. Soc., 78: 182-196.
Böhm, 1992, "The Computer Program LUSI: A New Method for the Novo Design of Enzyme Inhibitors," J. Computer-Aided Molecular Design, 6: 61-78.
Branden et al., 1999, "Introduction to Protein Structure Second Edition," Garland Publishing, Inc., New York: 374-375.
Brittain et al., 2009, "Polymorphism in Pharmaceutical Solids." Drugs and the Pharmaceutical Sciences, 2nd Edition, Edited by Brittain H.G., 192: 333-335.
Burger, 1991, "Isosterism and biososterism in drug design", Progress in Drug Research, Birkhauser Verlag.
Bussolino, 1997, "Molecular Mechanisms of Blood Vessel Formation," Trends Biochem. Sci., 22(7): 251-256.
Byrn et al., 1995, "Pharmaceutical Solids: A Strategic Approach to Regularity Considerations", Pharmaceutical Research, 12(7): 945-954.
CAS Registry Nos. 1261813-98-2, 1261613-86-8, and 1261518-21-1. Chemcats, 2011.
Catrina et al., 2004, "Hyperglycemia Regulates Hypoxia-Inducible Factor-1a Protein Stability and Function," Diabetes 53: 3226-3232.
Carey, 2006, Organic Chemistry 6th Ed., McGraw Hill, Chapter 19: 839-840.

Cheeseright, 2009, "The Identification of Bioisosteres as Drug Development Candidates", Innovations in Pharmaceutical Technology, issue 28.
Cherng, 2002, "Synthesis of substituted pryidines by the reactions of halopyridines with sulfur, oxygen and carbon nucleophiles under focused microwave irradition", Tetrahedron, Jun. 10, 2002, 58(24): 4931-4935.
Clinicaltrials.gov: archive: NCT01235936 Nn Sep. 30, 2012[online]. U.S. National Institute of Health, Aug. 30, 2012; retrieved from the internet at <http:clinicaltrials.gov/archive/NCT01235936/2012_09_30> on Aug. 30, 2012.
Cousins, "Retina Today", Oct. 2009, 2 pages; retrieved from the internet at <http://reinatoday.com/2009/10/1009_12.php>.
Costello et al., 2012, "Evidence for changes in RREB-1, ZIP3, and zinc in the early development of pancreatic adenocarcinoma", J Gastrointest Canc, 43: 570-578.
Cunliffe et al., 1992, "Novel Inhibitors of Proly14-Hydroxylase. 3. Inhibition by the Substrate Analogue N-Oxaloglycine and Its Derivatives," J. Med. Chem. 35: 2652-2658.
Demetriades et al., 2012, "Dynamic combinatinatorial chemistry employing embryonic boronic acids/boronate esters leads to potent oxygenase inhibitors", Angewandte Chemie, International Edition, May 25, 2012, 51(27): 6672-6675.
Designation of Inventors filed on entry into EP Regional Phase of EP Pat. No. 2044005.
Dranoff, 2003, "GM-CSF-secreting melanoma vaccines", Oncogene, 22: 3188-3192.
Elson et al., 2001, "Induction of hypervascularity without leakage or inflammation in transgenic mice overexpressing hypoxia-inducible factor-1α," Genes & Dev., 15: 2520-2532.
El Vidge et al., 2006, "Concordant Regulation of Gene Expression by Hypoxia and 2-Oxoglutarate-dependent Dioxygenase Inhibition", J. Biol. Chem., 281(22): 15215-15226.
Enoch et al., 2006, "ABC of wound healing. Non-surgical and drug treatments", BMJ, 332(7546):332:900-3.
European Patent Office, Interlocutory Decision in Opposition Proceedings dated May 3, 2013 for European Patent No. 2044005, 76 pages.
European Patent Office, Minutes of the Oral Proceedings Before the Opposition Division dated May 3, 2013 for European Patent No. 2044005, 6 pages.
Extract from USPTO patent assignment database regarding U.S. Appl. No. 11/821,936.
Favier et al., 2007, "HIF2α reduces growth rate but promotes angiogenesis in a mouse model of neuroblastoma", BMC Cancer, 7:139: 1-10.
Flower, 1999, "Modelling G-protein-coupled receptors for drug design," Biochimica et Biophysica Acta, 1422: 207-234.
Folkman et al., 1995, "Tumor Angiogenesis," The Molecular Basis of Cancer, Mendelsohn et al., eds., W. B. Saunders, Chapter 10: 206-232.
Franklin et al., Nov. 1991, "Approaches to the Design of Anti-Fibrotic Drugs," Biochem. Soc. Trans., 19(4): 812-5.
Gaunt, 1998, "Rational Design of Benzyl-Type Protecting Groups Allows Sequential Deprotection of Hydroxyl Groups by Catalytic Hydrogenolysis", 63(13): 4172-4173.
Gavhane et al., 2011, "Solid tumors: Facts, challenges, and solutions", International Journal of Pharma Sciences and Research, 2(1): 1-12.
Goodford, 1985, "A Computational Procedure for Determining Energetically Favorable Binding Sites on Biologically Important Macromolecules," J. Med. Chem., 28(7): 849-857.
Goodsell et al., 1990, "Automated Docking of Substrates to Proteins by Simulated Annealing", Proteins: Structure, Function, and Genetics, 8: 195-202.
Greer et al., 2012 "The updated biology of hypoxia inducible factor", EMBO J. 31: 2448-2460.
Guillory, 1999, "Generation of polymorphs, hydrates, solvates, and amorphous solids", HG Brittain (Ed.), Polymorphism in Pharmaceutical Solids, V. 95, Marcel Dekker, New York: 183-226.

(56) References Cited

OTHER PUBLICATIONS

Hardcastle et al., 2005, "Discovery of Potent Chromen-4-one Inhibitors of the DNA-Dependent Protein Kinase (DNA-PK) Using a Small-Molecule Library Approach", J. of Medicinal Chem., 48(24): 7829-7846.
Hoeksema et al., 1982, "Structure of Rubradirin", J. of American Chem. Society, 104(19): 5173-5181.
Hu et al., 2003, "Differential Roles of Hypoxia-Inducible Factor 1a (HIF-1α) and HIF-2α in Hypoxic Gene Regulation", Mol. Cell. Biol., 23: 9361-9374.
Ingersoll et al. "Hippuric Acid", Organic Syntheses, CV 2, 328; retrieved from the internet at <http:web.archive.org/web20020724135719/http://orgsyn.org/orgsyn/prepContent.asp?prep=cv2p0328> on Mar. 11, 2010.
International Preliminary Report on Patentability dated Dec. 10, 2013 for PCT/US2012/40833.
International Search Report dated May 8, 2008 for PCT/US2007/014832.
International Search Report and Written Opinion dated Aug. 29, 2012 for PCT/US2012/40833.
International Search Report and Written Opinion dated Apr. 20, 2015 for PCT/US2015/12634.
International Union of Pure and Applied Chemistry, Glossary of Class Names of Organic Compounds and Reactive Intermediates Based on Structure, Pure & D Appl. Chern., 67(8/9): 1307-1375 (1995).
Ivan et al., 2002, "Biochemical purification and pharmacological inhibition of a mammalian prolyl hydroxylase acting on hypoxia-inducible factor," Proceedings of the National Academy of Science, 99(21): 13459-13464.
Ivan et al., 2001, "HIFα Targeted for VHL-Mediated Destruction by Proline Hydroxylation: Implications for O2 Sensing", Science, 292: 464-468.
Ivanisevic et al., 2011, "Uses of X-Ray Powder Diffraction in the Pharmaceutical Industry." Pharmaceutical Formulation & Quality. Aug./Sep. 2011: 30-33.
Iyoda et al., 1990, "Homocoupling of aryl halides using nickel(II) complex and zinc in the presence of Et4NI. An efficient method for the synthesis of biaryls and bipyridines", Bull. Chem. Soc. Jpn., 63(1): 80-87.
Jaakkola et al., 2001, "Targeting of HIF-α to the von Hippel-Lindau Ubiquitylation Complex by O2-Regulated Prolyl Hydroxylation," Science, 292: 468-472.
Jones et al., 1995, "Molecular Recognition of Receptor Sites Using a Genetic Algorithm with a Description of Desolvation", J. Mol. Biol., 245: 43-53.
Kaelin, 2005, "Proline Hydroxylation and Gene Expression," Annual Rev. Biochem., 74: 115-125.
Karuppagounder et al., 2012 "Hypoxia-inducible factor prolyl hydroxylase inhibition: robust new target or another big bust for stroke therapeutics?", J. Cereb. Blood F. Met., 32: 1347-1361.
Kawashima et al., 1987, "Suppressive effect of quinolinic acid and hippuric acid on bone marrow erythroid growth and lymphocyte blast formation in uremia", Advances in Experimental Medicine and Biology, 223: 69-72.
Ke and Costa, 2006, "Hypoxia-Inducible Factor-1 (HIF-1)", Molecular Pharmacology, 70(5): 1469-1480.
Khandhadia et al., 2012, "Neurodegenerative Diseases", edited by Shamim I. Ahmed, Published by Landes Biosciences and Springer Science + Business Media, Chapter 2: 15-36.
Kietzmann et al., 2001, "Perivenous expression of the mRNA of the three hypoxia-inducible factor α-subunits, HIF1α, HIF2α and HIF3α, in rat liver", Biochem. J., 354: 531-537.
Kim et al., 2015, "Recent advances in developing inhibitors for hypoxia-inducible factor prolyl hydroxylases and their therapeutic implications", Molecules, 20: 20551-20568.
Krantz, 1991, "Erythropoietin," Blood, 77: 419-434.
Kuntz et al., 1982, "A Geometric Approach to Macromolecule-Ligand Interactions," J. Mol. Biol., 161: 269-288.
Kurti et al., 2005, "Strategic applications of named reactions in organic synthesis", El Sevior: 448-449.
Langsetmo et al., 2006, "Inhibition of HIF-Prolyl Hydroxylases with FG-4539 Is Neuroprotective in a Mouse Model of Permanent Focal Ischemia", International Stroke Conference, Kissimmee Florida, Presentation No. 427.
Lee et al., 2003, "Structure of Human FIH-1 Reveals a Unique Active Site Pocket and Interaction Sites for HIF-1 and von Hippel Lindau", JBC, 278: 7558-7563.
Li et al., 2000, "PR39, A Peptide Regulator of Angiogenesis," Nat Med., 6(1): 49-55.
Lima and Barreiro, 2005, "Bioisosterism: A Useful Strategy for Molecular Modification and Drug Design", Current Medicinal Chemistry, 12: 23-49.
Liu et al., Jun. 2011, "Hypoxia Induces Genomic DNA Demethylation through the Activation of HIF-1alpha and Transcriptional Upregulation of MAT2A in Hepatoma Cells", Mol. Cancer Ther., 10: 1113-1123.
Mancini et al., 2003, "Effect of Erythropoietin on Exercise Capacity in Patients with Moderate to Severe Chronic Heart Failure", Circulation, 107: 294-299.
McDonough et al., 2006, "Cellular Oxygen Sensing: Crystal Structure of Hypoxia-Inducible Factor Prolyl Hydroxylase (PHD2)", PNAS, 103(26): 9814-9819.
Miranker et al., 1991, "Functionality Maps of Binding Sites: A Multiple Copy Simultaneous Search Method", Proteins: Structure, Function and Genetics, 11: 29-34.
Morissette et al., 2004, "High-throughput crystallization: polymorphs, salts, co-crystals and solvates of pharmaceutical solids", Advanced Drug Delivery Reviews, 56: 275-300.
Myerson, 2002, Handbook of Industrial Crystallization, p. 249.
Nielsen et al., 2010, "Antiangiogenic therapy for Breast Cancer", Breast Cancer Res. 12: 209-227.
Nguyen et al., 2001, "Cellular Interactions in Vascular Growth and Differentiation", Int. Review of Cytology, 204: 1-48.
Nishibata et al., 1991, "Automatic Creation of Drug Candidate Structures Based on Receptor Structure. Starting Point for Artificial Lead Generation", Tetrahedron, 47( 43): 8985-8990.
Nowak et al., 2006, "Age-related macular degeneration (AMD): pathogenesis and therapy", Pharmacological Reports, 58: 353-363.
O'Reilly et al., 1994, "Angiostatin: A Novel Angiogenesis Inhibitor that Mediates the Suppression of Metastases by a Lewis Lung Carcinoma", Cell, 79: 315-328.
O'ReillyY et al., 1997, "Endostatin: An Endogenous Inhibitor of Angiogenesis and Tumor Growth", Cell, 88: 277-285.
Online Abstract showing publication date of Mcdonough et al. (2006) as Jun. 16, 2006.
PCT Request Form dated Jun. 26, 2007 for PCT/US2007/014832.
Pergola et al., 2016, "Vadadustat, a novel oral HIF stabilizer, provides effective anemia treatment in nondialysis-dependent chronic kidney disease", 90: 1115-1122.
Peyssonnaux et al., 2005, "HIF-1α Expression Regulates the Bactericidal Capacity of Phagocytes", J. Clinical Invest., 115(7): 1806-1815.
Piyamongkol et al., 2010, "Amido-3-hydroxypyridin-4-ones as Iron (III) Ligands", Chemistry A European Journal, 16: 6374-6381.
Prabhakar et al., 2012 "Adaptive and Maladaptive Cardiorespiratpry Responses to Continuous and Intermittent Hypoxia Mediated by Hypoxia-Inducible Factors 1 and 2", Physiol. Rev., 92: 967-1003.
PubChem Open Chemistry Database Compound Name: SCHEMBL3484399 (CID 49848485); Retrieved on from the internet: <https://pubchem.ncbi.nlm.nih.gov/compound/49848485> on Mar. 15, 2016.
PubChem Open Chemistry Database Compound Name: Zeadcohjerwfoi-Uhfffaoysa-M (CID 71491828); retrieved from the internet: <https://pubchem.ncbi.nlm.nih.gov/compound/71491828> on Mar. 21, 2016.
Qian et al., 2013, "A Randomized, Double-Blind, Placebo Controlled Trial of FG-4592 for Correction of Anemia in Subjects with Chronic Kidney Disease in China," Oral Abstract FR-OR011, J. Am. Soc. Nephrol., 24: 38A.
Qunibi et al., 2011, "A randomized controlled trial comparing intravenous ferric carboxymaltose with oral iron for treatment of

(56) References Cited

OTHER PUBLICATIONS iron deficiency of non-dialysis-dependent chronic kidney disease patients", Nephrol Dial Transplant, 26(5): 1599-1607.
Rahtu-Korpela et al., 2014, "HIF Prolyl 4-Hydroxylase-2 Inhibition Improves Glucose and Lipid Metabolism and Protects Against Obesity and Metabolic Dysfunction," Diabetes 63: 3324-3333.
Rankin et al., 2007, "Hypoxia-inducible factor-2 (HIF-2) regulates hepatic erythropoietin in vivo" J. Clin. Invest. 117:1069-1076.
Ratcliffe et al., 2007, "HIF-1 and HIF-2: working alone or together in hypoxia?" J. Clin. Inv., 117(4):862-865.
Redondo et al., 2000, "Vascular endothelial growth factor (VEGF) and melanoma. N-Acetylcysteine downregulates VEGF production in vitro", Cytokine, 12(4):374-378.
Request for Correction of Inventorship at USPTO regarding U.S. Appl. No. 11/821,936.
Roda et al., 2012, "Stabilization of HIF-2a induces sVEGFR-1 production from tumor-associated macrophages and decreases tumor growth in a murine melanoma model", J. Immunology, 189: 3168-3177.
Schelhass and Waldmann, 1996, "Protecting Group Strategies in Organic Synthesis", Chem. Int. Ed. Engl., 36: 2056-2083.
Schoneberg et al., 1999, "Structural Basis of G Protein-Coupled Receptor Function," Molecular and Cellular Endocrinology, 151: 181-193.
Search Report dated Apr. 28, 2011 for European Pat. App. No. 11000872.9.
Semenza et al., 1994, "Transcriptional Regulation of Genes Encoding Glycolytic Enzymes by Hypoxia-Inducible Factor 1", J. Biol. Chem., 269: 23757-23763.
Semenza et al., 1994, "Regulation of Erythropoietin Production: New Insights into Molecular Mechanisms of Oxygen Homeostasis", Hematol. Oncol. Clin. North Am., 8: 863-884.
Semenza, 2000, "HIF-1 and human disease: one highly involved factor", Genes & Development, 14: 1983-1991.
Semenza, 2002, "Signal Transduction to Hypoxia-inducible Factor 1", Biochem. Pharmacol, 64: 993-998.
Sexton, 1999, "Recent advances in our understanding of peptide hormone receptors and RAMPS", Current Opinion in Drug Discovery and Development, 2(5): 440-448.
Seymour et al., 2011, "Decision T 0777/08 of the Boards of Appeal of the European Patent Office", retrieved from the internet: <http://www.epo.org/law-practice/case-law-appeals/pdf/t080777ex1.pdf> on Dec. 19, 2017.
Sheehan, 1996, "3-Hydroxypicolinic Acid and Some of its Derivatives", J. Organic Chemistry 31(3): 636-638.
Siddiq, 2005, "Hypoxia-inducible factor prolyl 4-hydroxylase inhibition", J. of Biological Chemistry, 280(50): 41732-41743.
Sowter et al., 2003 "Predominant Role of Hypoxia-Inducible Transcription Factor (Hif)-1α versus (Hif)-2α in Regulation of the Transcriptional Response to Hypoxia", Cancer Res. 63: 6130-6134.
Sporn and Suh, 2000, "Chemoprevention of cancer", Carcinogenesis, 21(3): 525-530.
Stille, J. K., 1986, Angew. Chem., Int. ED. Engl., vol. 25: 508.
Sutter, 2000, "Hypoxia-inducible factor 1 alpha protein expression is controlled by oxygen-regulated ubiquitination that is disrupted by deletions and missense mutations", PNAS, 97(9): 4748-4753.
Teicher et al., 1994, "Potentiation of Cytotoxic Cancer Therapies by TNP-470 Alone and with Other Anti-Angiogenic Agents", Int. J. Cancer, 57: 920-925.
Thoppil and Bishayee, 2011, "Terpenoids as potential chemopreventive and therapeutic agents in liver cancer", World J. Hepatol., 3(9): 228-249.
Thornber, 1979, "Isosterism and Molecular Modification in Drug Design", Progress Drug Res., vol. 37: 563-580.
Tzschucke et al., 2004, "Fluorous-Silica-Supported Perfluoro-Tagged Palladium Complexes Catalyze Suzuki Coupling in Water", Helvetica Chimica Acta; 87: 2882-2889.
Variankaval et al., 2008, "From form to unction: crystallization of active pharmaceutical ingredients", AICHE Journal, Jul. 2008, 54(7): 1682-1688.

Vickerstaffe et al., 2004, "Fully Automated Polymer-Assisted Synthesis of 1,5-Biaryl Pyrazoles", J. Comb. Chem., 6:332-33.
Vincent et al., 2000, "Angiogenesis is Induced in a Rabbit Model of Hindlimb Ischemia by Naked DNA Encoding an HIF-1a/VP16 Hybrid Transcription Factor", Circulation, 102: 2255-2261.
Vippagunta et al., 2001, "Crystalline solids", Adv. Drug Deliv. Rev., 48(1): 3-26.
Wade et al., 2006, "Organic Chemistry", 6th ED., Pearson Prentice Hall, US: 780-781.
Warnecke et al., 2003, "Activation of the Hypoxia-Inducible Factor Pathway and Stimulation of Angiogenesis by Application of Prolyl Hydroxylase Inhibitors", FASEB Journal, 17: 1186-1188.
Warshakoon et al., 2006, "Design and synthesis of substituted pyridine derivatives as HIF-1alpha prolyl hydroxylase inhibitors", Bioorganic & Medicinal Chemistry Letters, 16: 5616-5620.
Wax et al., 1996, "SM-20 is a Novel20-kd Protein Whose Expression in the Arterial Wall is Restricted to Smooth Muscle", Lab. Invest., 74(4): 797-808.
Weidner et al., 1991, "Tumor Angiogenesis and Metastasis—Correlation in Invasive Breast Carcinoma", New Eng. J. Med., 324(1): 1-8.
Wiesener et al., 2003 "Widespread hypoxia-inducible expression of HIF-2alpha in distinct cell populations of different organs." FASEB J.17(2): 271-3.
Wright et al., 2003, "Activation of the Prolyl Hydroxylase Oxygen-Sensor Results in Induction of GLUT1, Heme Oxygenase-1, and Nitric-Oxide Synthase Proteins and Confers Protection from Metabolic Inhibition to Cardiomyocytes", J. Bio. Chem., 278(22): 20235-20239.
Wu et al., 2010 "A systems biology perspective on sVEGFR1: its biological function, pathogenic role and therapeutic use", J. Cell. Mol. Med. 14:528-552.
Yang et al., 2012, "Desmoplakin acts as a tumor suppressor by inhibition of the Wnt/beta-catenin signaling pathway in human lung cancer", Carcinogenesis, 33(10): 1863-1870.
U.S. Appl. No. 15/875,495, filed Jan. 19, 2018, Kawamoto et al.
U.S. Appl. No. 15/994,348, filed May 31, 2018, Copp et al.
U.S. Appl. No. 16/119,146, filed Aug. 31, 2018, Kawamoto et al.
Bao et al., "Chronic Inhibition of Hypoxia-inducible Factor Prolyl 4-hydroxylase Improves Ventricular Performance, Remodeling, and Vascularity After Myocardial Infarction in the Rat", J Cardiovasc Pharmacol, 56(2): 147-155 (2010) (Exhibit C).
Beuck et al., "Hypoxia-inducible factor stabilizers and other small-molecule erythropoiesis-stimulating agents in current and preventive doping analysis", Drug Test. Analysis, 4(11): 830-845 (2012).
Krapf et al., "Arterial Hypertension Induced by Erythropoietin and Erythropoiesis-Stimulating Agents (ESA)", Clin J Am Soc Nephrol 4: 470-480 (2009) (Exhibit A).
Tekin et al., "Hypoxia inducible factor 1 (HIF-1) and cardioprotection", Acta Pharmacologica Sinica, 31: 1085-1094 (2010).
Waknine, "Black Box Warning for Erythropoiesis-Stimulating Agents", Medscape, Mar. 12, 2007 (Exhibit B).
Buch et al., "Dose Exposure Relationship of AKB-6548 Is Independent of the Level of Renal Function," J. Am. Soc. Nephrol., 26 (Suppl):Abstract SA-PO537, 2015 (Exhibit D).
Buch et al., "Dose Exposure Relationship of AKB-6548 Is Independent of the Level of Renal Function," Poster SA-PO537 at American Society of Nephrology (ASN) Kidney Week 2015, Nov. 3-8, 2015 (Exhibit E).
Donkin et al., "A Substance P Antagonist Reduces Axonal Injury and Improves Neurologic Outcome When Administered Up to 12 Hours after Traumatic Brain Injury", Journal of Neurotrauma., US, (Feb. 1, 2011), vol. 28, No. 2, doi: 10.1089/neu.2010.1632, ISSN 0897-7151, pp. 217-224, XP055344482[Y] 1-9* abstract *.
Donkin et al., "Substance P is Associated with the Development of Brain Edema and Functional Deficits after Traumatic Brain Injury", Journal of Cerebral Blood Flow & Metabolism, US, (Aug. 1, 2009), vol. 29, No. 8, doi:10.1038/jcbfm.2009.63, ISSN 0271-678X, pp. 1388-1398, XP055344477[Y] 1-9* abstract *.
Stern et al, "Long-term Consequences of Repetitive Brain Trauma: Chronic Traumatic Encephalopathy", PM&R, vol. 3, No. 10, doi:10.1016/J.PMRJ.2011.08.008, ISSN 1934-1482, (Oct. 26, 2011), pp. S460-S467, (Aug. 19, 2011), XP028328976[Y] 1-9* abstract *.

(56) References Cited

OTHER PUBLICATIONS

BPT closes $12 million in Series B financing. Membrane Technology, Oct. 10, 2009, Elsevier Science, XX. vol. 2009, Nr: 10, pp. 1,16 https://www.sciencedirect.com/science/article/pii/S0958211809701983.
WHO Drug Information, International Nonproprietary Names for Pharmaceutical Substances (INN): vol. 29, No. 4 (2015), pp. 503-573 (Exhibit A).
U.S. Appl. No. 16/786,187, filed Feb. 10, 2020, Copp et al.
U.S. Appl. No. 16/908,092, filed Jun. 22, 2020, Kawamoto et al.
U.S. Appl. No. 16/921,273, filed Jul. 6, 2020, Lanthier et al.
Crowley, Patrick, and Luigi G. Martini. "Drug-excipient interactions." *Pharm Technol* 4 (2001): 7-12.
Haywood, Alison, and Beverley Glass. "Pharmaceutical excipients: where do we begin ?." *Australian Prescribing* 34 (2011): 112-114.
Leuenberger, Hans, and Michael Lanz. "Pharmaceutical powder technology—from art to science: the challenge of the FDA's Process Analytical Technology initiative." *Advanced powder technology* 16.1 (2005): 3-25.
Exhibit A—Appeal 2009-1066, 2009 Pat. App. LEXIS 10905 (BPAI Mar. 11, 2009).
Exhibit B—Appeal No. 2012-008295, 2015 Pat. App. LEXIS 435 (PTAB Jan. 27, 2015).
Akebia Therapeutics, "Akebia Announces Vadadustat Efficacy and Safety Data to be Presented at American Society of Nephrology Kidney Week 2021," Oct. 18, 2021, https://www.prnewswire.com/news-releases/akebia-announces-vadadustat-efficacy-and-safety-data-to-be-presented-at-american-society-of-nephrology-kidney-week-2021-301401831.html.
Abstract: PO0460, "Comprehensive Safety Profile of Vadadustat from Global Phase 3 Clinical Trials."
Abstract: PO0461, "Vadadustat, an Oral HIF-PHI, Is Not Associated with Increased Risk of Neoplasm in Patients with Anemia due to CKD."
Abstract: PO0462, "Assessment of Thromboembolic Events with Vadadustat vs. Darbepoetin Alfa for Treatment of Anemia in Patients with Non-Dialysis-Dependent CKD."
Abstract: PO0463, "Thromboembolic Events with Vadadustat vs Darbepoetin Alfa for Anemia Treatment in Patients with Dialysis-Dependent CKD."
Abstract: PO0464, "Vadadustat for Treatment of Anemia in Patients with Dialysis-Dependent CKD Receiving Peritoneal Dialysis."
Abstract: PO0482, "Iron-Related Outcomes in Patients with Non-Dialysis-Dependent CKD Randomized to Vadadustat vs Darbepoetin Alfa."
Abstract: PO0457, "Iron-Related Outcomes in Patients with Dialysis-Dependent CKD Randomized to Vadadustat vs. Darbepoetin Alfa."
Chertow et al., "Vadadustat in Patients with Anemia and Non-Dialysis-Dependent CKD," The New England Journal of Medicine, vol. 384, No. 17, Apr. 29, 2021.
Bolhuis et al., "Polyols as filler-binders for disintegrating tablets prepared by direct compaction," Drug Development and Industrial Pharmacy, 2009; 35(6):671-677.
Lim, "Clinical Practice Guidelines and Clinical Practice Recommendations for Anemia in Chronic Kidney Disease in Adults," Appendix No. 2, vol. 25, Kidney Research and Clinical Practice.
Apsden et al., Preventing Medical Errors (National Academy of Sciences—Institute of Medicine), 2007, English, totaling 481 pages.
ClinicalTrials.gov archive NCT01381094 (2012): "42-Day Repeat Oral Dose Study of AKB-6548 in Subjects With Chronic Kidney Disease and Anemia". U.S. National Institutes of Health, Mar. 29, 2012. 116 pages.
Handbook of Pharmaceutical Excipients, Sixth Edition 2009, Edited by Raymond C Rowe BPharm, PhD, DSC, FRPharmS, FRSC, CPhys, MinstP. pp.s 129-133 and 663-666.
International Search Report and Written Opinion for PCT/US14/40889, dated Dec. 31, 2014. 20 pages.
National Center for Biotechnology Information (2022). PubChem Compound Summary for CID 23634441, Vadadustat. Retrieved Sep. 14, 2022 from https://pubchem.ncbi.nim.nih.gov/compoundVadadustat. 1 page.
Perrie et al., "Chapter One. Controlling Drug Delivery," Pharmaceutics—Drug Delivery and Targeting (Second Edition), Pharmaceutical Press, 2007, English, totaling 24 pages.

\* cited by examiner

SEQUENCE LISTING

```
<160> NUMBER OF SEQ ID NOS: 3

<210> SEQ ID NO 1
<211> LENGTH: 19
<212> TYPE: PRT
<213> ORGANISM: Unknown
<220> FEATURE:
<223> OTHER INFORMATION: HIF-1a peptide

<400> SEQUENCE: 1

Asp Leu Asp Leu Glu Ala Leu Ala Pro Tyr Ile Pro Ala Asp Asp
1               5                   10                  15

Phe Gln Leu

<210> SEQ ID NO 2
<211> LENGTH: 354
<212> TYPE: PRT
<213> ORGANISM: Homo sapiens
<220> FEATURE:
<223> OTHER INFORMATION: human erythroferrone protein
<300> PUBLICATION INFORMATION:
<308> DATABASE ACCESSION NUMBER: AHL84165.1
<309> DATABASE ENTRY DATE: 2014-03-18
<313> RELEVANT RESIDUES IN SEQ ID NO: (1)..(354)

<400> SEQUENCE: 2

Met Ala Pro Ala Arg Arg Pro Ala Gly Ala Arg Leu Leu Leu Val Tyr
1               5                   10                  15
```

Ala Gly Leu Leu Ala Ala Ala Ala Gly Leu Gly Ser Pro Glu Pro
            20                  25                  30

Gly Ala Pro Ser Arg Ser Arg Ala Arg Arg Glu Pro Pro Gly Asn
        35                  40                  45

Glu Leu Pro Arg Gly Pro Gly Glu Ser Arg Ala Gly Pro Ala Ala Arg
 50                  55                  60

Pro Pro Glu Pro Thr Ala Glu Arg Ala His Ser Val Asp Pro Arg Asp
 65                  70                  75                  80

Ala Trp Met Leu Phe Val Arg Gln Ser Asp Lys Gly Val Asn Gly Lys
                85                  90                  95

Lys Arg Ser Arg Gly Lys Ala Lys Lys Leu Lys Phe Gly Leu Pro Gly
            100                 105                 110

Pro Pro Gly Pro Pro Gly Pro Gln Gly Pro Pro Gly Pro Ile Ile Pro
        115                 120                 125

Pro Glu Ala Leu Leu Lys Glu Phe Gln Leu Leu Leu Lys Gly Ala Val
130                 135                 140

Arg Gln Arg Glu Arg Ala Glu Pro Glu Pro Cys Thr Cys Gly Pro Ala
145                 150                 155                 160

Gly Pro Val Ala Ala Ser Leu Ala Pro Val Ser Ala Thr Ala Gly Glu
                165                 170                 175

Asp Asp Asp Asp Val Val Gly Asp Val Leu Ala Leu Leu Ala Ala Pro
            180                 185                 190

Leu Ala Pro Gly Pro Arg Ala Pro Arg Val Glu Ala Ala Phe Leu Cys
        195                 200                 205

Arg Leu Arg Arg Asp Ala Leu Val Glu Arg Arg Ala Leu His Glu Leu
210                 215                 220

Gly Val Tyr Tyr Leu Pro Asp Ala Glu Gly Ala Phe Arg Arg Gly Pro
225                 230                 235                 240

Gly Leu Asn Leu Thr Ser Gly Gln Tyr Arg Ala Pro Val Ala Gly Phe
                245                 250                 255

Tyr Ala Leu Ala Ala Thr Leu His Val Ala Leu Gly Glu Pro Pro Arg
            260                 265                 270

Arg Gly Pro Pro Arg Pro Arg Asp His Leu Arg Leu Leu Ile Cys Ile
        275                 280                 285

Gln Ser Arg Cys Gln Arg Asn Ala Ser Leu Glu Ala Ile Met Gly Leu
290                 295                 300

Glu Ser Ser Ser Glu Leu Phe Thr Ile Ser Val Asn Gly Val Leu Tyr
305                 310                 315                 320

Leu Gln Met Gly Gln Trp Thr Ser Val Phe Leu Asp Asn Ala Ser Gly
                325                 330                 335

Cys Ser Leu Thr Val Arg Ser Gly Ser His Phe Ser Ala Val Leu Leu
            340                 345                 350

Gly Val

<210> SEQ ID NO 3
<211> LENGTH: 1065
<212> TYPE: DNA
<213> ORGANISM: Homo sapiens
<220> FEATURE:
<223> OTHER INFORMATION: human erythroferrone (FAM132B) mRNA
<300> PUBLICATION INFORMATION:
<308> DATABASE ACCESSION NUMBER: KF984314
<309> DATABASE ENTRY DATE: 2014-03-18
<313> RELEVANT RESIDUES IN SEQ ID NO: (1)..(1065)

<400> SEQUENCE: 3

```
atggccccgg cccgccgccc cgccggagcc cgcctgctgc tcgtctacgc gggcctgctg      60
gccgccgccg ccgcgggcct ggggtccccg gagcctgggg cgccctcgag gagccgcgcc     120
cgcagggagc cgccgcccgg gaacgagctg ccccggggcc ccggggagag ccgcgcgggg     180
ccggccgctc gtccgccgga gcccaccgct gagcgtgcac acagcgtcga cccccgggac     240
gcctggatgc tcttcgtcag gcagagtgac aagggtgtca atggcaagaa gaggagcagg     300
ggcaaggcca agaagctgaa gttcggcttg ccagggcccc ctgggcctcc cggtccccag     360
ggccccccag gccccatcat cccacccgag gcgctgctga aggagttcca gctgctgctg     420
aaaggtgcgg tgcggcagcg ggagcgcgcg gagcccgaac cctgtacgtg tggcccccgcc    480 gggccggtcg ctgcgagcct cgccccggtc tcggccaccg ccggggagga cgacgacgac     540
gtggtggggg acgtgctggc actgctggcc gcgcccctgg ccccggggcc gcgggcgccg     600
cgcgtggagg ccgctttcct ctgccgcctg cgccgggacg cgttggtgga gcggcgcgcg     660
ctgcacgagc ttggcgtcta ctacctgccc gacgccgagg gtgccttccg ccgcggcccg     720
ggcctgaact tgaccagcgg ccagtacagg gcgcccgtgg ctggcttcta cgctctcgcc     780
gccacgctgc acgtggcgct cggggagccg ccgaggaggg ggccgccgcg ccccgggac      840 cacctgcgcc tgctcatctg catccagtcc cggtgccagc gcaacgcctc cctggaggcc     900
atcatgggcc tggagagcag cagtgagctc ttcaccatct ctgtgaatgg cgtcctgtac     960
ctgcagatgg ggcagtggac ctccgtgttc ttggacaacg ccagcggctg ctccctcaca   1020
gtgcgcagtg gctcccactt cagtgctgtc ctcctgggcg tgtga                   1065
```

COMPOSITIONS AND METHODS FOR TREATING ANEMIA

The present application is a national stage entry of International Patent Application No. PCT/US2014/040889, filed on Jun. 4, 2014, which claims benefit of priority from U.S. provisional patent application numbers 61/834,808 filed on Jun. 13, 2013; 61/889,478 filed on Oct. 10, 2013; 61/898,890 filed on Nov. 1, 2013; 61/898,885 filed on Nov. 1, 2013; and 61/912,185 filed on Dec. 5, 2013, each of which is incorporated herein by reference in its entirety.

1 FIELD OF THE INVENTION

The present disclosure relates to uses of a HIF prolyl hydroxylase inhibitor in treating or preventing anemia, such as anemia secondary to or associated with chronic kidney disease, anemia associated with or resulting from chemotherapy, or anemia associated with AIDS. Further, the present disclosure relates to HIF prolyl hydroxylase inhibitor compounds and pharmaceutically acceptable salts thereof, compositions comprising the HIF prolyl hydroxylase inhibitor compounds, and to methods for treating or preventing diseases such as, Peripheral Vascular Disease (PVD), Coronary Artery Disease (CAD), heart failure, ischemia, hypoxia and anemia. In addition, the present disclosure relates to specific doses of, and dosing regimens for, uses of a HIF prolyl hydroxylase inhibitor in treating or preventing anemia, such as anemia secondary to or associated with chronic kidney disease, anemia associated with or resulting from chemotherapy, or anemia associated with AIDS.

2 BACKGROUND OF THE INVENTION

2.1 Hypoxia-Inducible Factor

Hypoxia-inducible factor (HIF) is a transcription factor that is a key regulator of responses to hypoxia. In response to hypoxic conditions, i.e., reduced oxygen levels in the cellular environment, HIF upregulates transcription of several target genes, including those encoding erythropoietin. HIF is a heteroduplex comprising an alpha and beta subunit. While the beta subunit is normally present in excess and is not dependent on oxygen tension, the HIF-alpha subunit is only detectable in cells under hypoxic conditions. In this regard, the accumulation of HIF-alpha is regulated primarily by hydroxylation at two proline residues by a family of prolyl hydroxylases known as HIF prolyl hydroxylases, wherein hydroxylation of one or both of the proline residues leads to the rapid degradation of HIF-alpha. Accordingly, inhibition of HIF prolyl hydroxylase results in stabilization and accumulation of HIF-alpha (i.e., the degradation of HIF-alpha is reduced), thereby leading to an increase in the amount of HIF-alpha available for formation of the HIF heterodimer and upregulation of target genes, such as the Erythropoietin gene. Conversely, activation of HIF prolyl hydroxylase results in destabilization of HIF-alpha (i.e., the degradation of HIF-alpha is increased), thereby leading to a decrease in the amount of HIF-alpha available for formation of the HIF heterodimer and downregulation of target genes, such as VEGF.

The family of hypoxia inducible factors includes HIF-1-alpha, HIF-2-alpha, and HIF-3-alpha.

A new class of prolyl hydroxylase inhibitors and their use to treat or prevent diseases ameliorated by modulation of hypoxia-inducible factor (HIF) prolyl hydroxylase are described in U.S. Pat. No. 7,811,593, which is incorporated herein by reference in its entirety. The synthesis of such prolyl hydroxylase inhibitors is described in U.S. Patent Publication No. 2012/0309977, which is incorporated herein by reference in its entirety. Such compounds inhibit HIF prolyl hydroxylase, thereby stabilizing HIF-alpha. As a consequence of stabilizing HIF-alpha, endogenous erythropoietin (EPO) production is increased. As with all drugs, proper doses and dosing regimens for treating patients having diseases such as anemia are essential for achieving a desired or optimal therapeutic effect without adverse effects or unwanted side-effects. Indeed, many active compounds fail in clinical trials because an effective and safe dosing regimen cannot be found.

Therefore, a need exists for safe, effective, and non-toxic doses and dosing regimens that either avoid or reduce adverse or unwanted effects, provide an optimal therapeutic effect or both, that is, provide a desirable therapeutic profile.

2.2 Erythropoietin

Treatment of anemia associated with chronic kidney disease (CKD) using erythropoiesis-stimulating agents often results in prolonged, supraphysiologic erythropoietin (EPO) levels, which are implicated in increased unwanted cardiovascular side effects, including hypertension and thromboembolic events. Therefore a need exists for treatment of anemia associated with chronic kidney disease (CKD) without prolonged, supraphysiologic erythropoietin (EPO) levels.

2.3 Iron Metabolism

HIF regulates transcription of several target genes, including those encoding proteins involved in iron metabolism. Although iron is considered to be essential for living cells, excess iron accumulation is associated with formation of toxic free radicals and progressive tissue damage. An excess of iron may also lead to a higher risk for cardiovascular events and thromboembolic events. Iron overload may be caused for example by blood transfusions or anemias that arise from ineffective crythropoiesis. A need exists for treatment of anemia without increasing the risk of iron overload.

2.4 Hepcidin

Under anemic or hypoxic conditions, not only is erythropoietin expression increased, leading to a stimulation of erythropoietic activity, but in parallel, hepcidin gene expression is decreased. Hepcidin blocks the action of ferroportin. Ferroportin moves iron out of cells. Therefore, when hepcidin expression is decreased in a subject, ferroportin action is unblocked, and iron is released from the cells, thereby increasing the risk of iron overload in a subject. A need exists for treatment of anemias without decreasing the levels of hepcidin, especially in situations where iron overload is a concern. Erythroferrone has been identified as a suppressor of hepcidin (Kautz et al. 2014, Nature Genetics, Advance Online Publication on Jun. 1, 2014, Identification of erythroferrone as an erythroid regulator of iron metabolism).

3 SUMMARY OF THE INVENTION

3.1 Dosage

Disclosed herein are dosing regimens wherein specific doses of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, and Metabolite 2 or a pharmaceutically acceptable salt, solvate, or hydrate thereof are administered according to a specific dosing regimen to modulate HIF prolyl hydroxylase, thereby stabilizing HIF-alpha, and thereby treating anemia (e.g. anemia secondary to chronic kidney disease). See Section 5.2 for a description of these formulae and compounds. Further disclosed herein are specific doses and unit dosage forms of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, and Metabolite 2 or a pharmaceutically acceptable salt, solvate, or hydrate thereof. In specific embodiments, the compound is {[5-(3-chlorophenyl)-3-hydroxypyridine-2-carbonyl]amino}acetic acid. In certain specific embodiments, the compound is a pharmaceutically acceptable salt of Compound 1. In certain specific embodiments, the compound is a solvate of Compound 1. In certain specific embodiments, the compound is a hydrate of Compound 1.

In certain embodiments, described herein are methods for treating or preventing a disease ameliorated by modulation of HIF prolyl hydroxylase comprising administering to a patient having a disease ameliorated by modulation of HIF prolyl hydroxylase an effective amount of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, and Metabolite 2 or a pharmaceutically acceptable salt, solvate, or hydrate thereof. In specific embodiments, the compound is Compound 1. In specific embodiments, the compound is Compound 7.

In certain embodiments, a daily dose of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, and Metabolite 2 or a pharmaceutically acceptable salt, solvate, or hydrate thereof for the uses described herein is about 100 mg, about 110 mg, about 120 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, about 260 mg, about 270 mg, about 280 mg, about 290 mg, about 300 mg, about 310 mg, about 320 mg, about 330 mg, about 340 mg, about 350 mg, about 360 mg, about 370 mg, about 380 mg, about 390 mg, about 400 mg, about 410 mg, about 420 mg, about 430 mg, about 440 mg, about 450 mg, about 600 mg, or about 750 mg. In certain such embodiments, the daily dose is about 150 mg, about 300 mg, about 450 mg, or about 600 mg. Such daily doses may be administered orally, once daily, twice daily, or three times daily, preferably once daily. In certain embodiments, the daily dose is 2 mg/kg, 2.1 mg/kg, 2.2 mg/kg, 2.3 mg/kg, 2.4 mg/kg, 2.5 mg/kg, 2.6 mg/kg, 2.7 mg/kg, 2.8 mg/kg, 2.9 mg/kg, 3 mg/kg, 3.1 mg/kg, 3.2 mg/kg, 3.3 mg/kg, 3.4 mg/kg, 3.5 mg/kg, 3.6 mg/kg, 3.7 mg/kg, 3.8 mg/kg, 3.9 mg/kg, or 4 mg/kg.

In certain embodiments, provided herein are methods for treating or preventing anemia, such as anemia secondary to chronic kidney disease, comprising administering to a patient having anemia an effective amount of an effective amount of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, and Metabolite 2 or a pharmaceutically acceptable salt, solvate, or hydrate thereof. In certain such embodiments, a daily dose a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, and Metabolite 2 or a pharmaceutically acceptable salt, solvate, or hydrate thereof, specifically a daily dose of Compound 1 is about 100 mg, about 110 mg, about 120 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, about 260 mg, about 270 mg, about 280 mg, about 290 mg, about 300 mg, about 310 mg, about 320 mg, about 330 mg, about 340 mg, about 350 mg, about 360 mg, about 370 mg, about 380 mg, about 390 mg, about 400 mg, about 410 mg, about 420 mg, about 430 mg, about 440 mg, about 450 mg, about 600 mg, or about 750 mg. In certain such embodiments, the daily dose is about 150 mg, about 300 mg, about 450 mg, or about 600 mg. Such daily doses may be administered orally, once daily, twice daily, or three times daily, preferably once daily. In certain embodiments, the daily dose is 2 mg/kg, 2.1 mg/kg, 2.2 mg/kg, 2.3 mg/kg, 2.4 mg/kg, 2.5 mg/kg, 2.6 mg/kg, 2.7 mg/kg, 2.8 mg/kg, 2.9 mg/kg, 3 mg/kg, 3.1 mg/kg, 3.2 mg/kg, 3.3 mg/kg, 3.4 mg/kg, 3.5 mg/kg, 3.6 mg/kg, 3.7 mg/kg, 3.8 mg/kg, 3.9 mg/kg, or 4 mg/kg.

In certain embodiments, provided herein are a unit dosage form comprising a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, and Metabolite 2 or a pharmaceutically acceptable salt, solvate, or hydrate thereof, specifically Compound 1, in an amount of about 150 mg. In certain such embodiments, the unit dosage form is a tablet or capsule.

In certain embodiments, provided herein are methods of maintaining the level of hemoglobin in a patient having anemia, such as anemia secondary to chronic kidney disease, at a level of at least about 8.0 g/dL and at or below about 13.0 g/dL, at least about 8.5 g/dL and at or below 13.0 g/dL, at least about 9.0 g/dL and at or below 13.0 g/dL, at least about 9.5 g/dL and at or below 13.0 g/dL, or at least about 10.0 g/dL and at or below about 13.0 g/dL, comprising administering an effective amount of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, and Metabolite 2 or a pharmaceutically acceptable salt, solvate, or hydrate thereof, specifically Compound 1, to a patient having anemia. In certain such embodiments, provided herein are maintaining the level of hemoglobin in a patient having anemia at a level of at least about 11.0 g/dL, such as at least about 11.0 g/dL and at or below about 13.0 g/dL, comprising administering an effective amount of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, and Metabolite 2 or a pharmaceutically acceptable salt, solvate, or hydrate thereof, specifically Compound 1. In certain such embodiments, a daily dose of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, and Metabolite 2 or a pharmaceutically acceptable salt, solvate, or hydrate thereof, specifically Compound 1, is about 150 mg, about 300 mg, about 450 mg, about 600, or about 750 mg. In certain such embodiments, the daily dose is about 150 mg, about 300 mg, about 450 mg, or about 600 mg. Such daily doses may be administered orally, once daily, twice daily, or three times daily, preferably once daily. In certain embodiments, the daily dose is 2 mg/kg, 2.1 mg/kg, 2.2 mg/kg, 2.3 mg/kg, 2.4 mg/kg, 2.5 mg/kg, 2.6 mg/kg, 2.7 mg/kg, 2.8 mg/kg, 2.9 mg/kg, 3 mg/kg, 3.1 mg/kg, 3.2 mg/kg, 3.3 mg/kg, 3.4 mg/kg, 3.5 mg/kg, 3.6 mg/kg, 3.7 mg/kg, 3.8 mg/kg, 3.9 mg/kg, or 4 mg/kg.

In certain embodiments, provided herein are methods for increasing the level of hemoglobin in a patient having anemia, such as anemia of chronic kidney disease, by at least about 0.1 g/dL, by at least about 0.2 g/dL, by at least about 0.3 g/dL, by at least about 0.4 g/dL, by at least about 0.5 g/dL, by at least about 0.6 g/dL, by at least about 0.7 g/dL, by at least about 0.8 g/dL, by at least about 0.9 g/dL, by at least about 1.0 g/dL, by at least about 1.1 g/dL, by at least about 1.2 g/dL, by at least about 1.3 g/dL, by at least about 1.4 g/dL, or by at least about 1.5 g/dL relative to a baseline hemoglobin level in a patient, comprising administering an effective amount a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, and Metabolite 2 or a pharmaceutically acceptable salt, solvate, or hydrate thereof, preferably Compound 1, to a patient having anemia. In certain such embodiments, such a daily dose is about 150 mg, about 300 mg, about 450 mg, about 600, or about 750 mg of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, and Metabolite 2. In certain such embodiments, the daily dose is about 150 mg, about 300 mg, about 450 mg, or about 600 mg. Such daily doses may be administered orally, once daily, twice daily, or three times daily, preferably once daily.

In certain embodiments, provided herein is a method for treating or preventing anemia in a patient, wherein the method comprises administering to the patient a pharmaceutically effective amount of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, and Metabolite 2 or a pharmaceutically acceptable salt, solvate, or hydrate thereof, wherein the pharmaceutically effective amount is suitable to increase the level of hemoglobin by at least about 0.5 g/dL, by at least about 0.6 g/dL, by at least about 0.7 g/dL, by at least about 0.8 g/dL, by at least about 0.9 g/dL, by at least about 1.0 g/dL, by at least about 1.2 g/dL, or by at least about 1.5 g/dL relative to a baseline hemoglobin level in the patient while:

a) restoring or maintaining the diurnal pattern of EPO serum levels;
b) increasing the total iron binding capacity;
c) increasing the total iron binding capacity without increasing significantly the total iron levels; and/or
c) not significantly decreasing hepcidin levels.

In certain embodiments, provided herein is a compound as disclosed in section 5.2 for the treatment of a disease, condition, or disorder as disclosed in sections 5.4 and 5.7 at a dose as disclosed in 5.5.

3.2 Erythropoietin

In certain embodiments, provided herein are various methods for treating a disease or condition related to diminished endogenous production of erythropoietin (EPO), comprising administering to a patient having a disease or condition related to diminished endogenous production of EPO a sufficient number of successive doses of a HIF prolyl hydroxylase inhibitor or a HIF-alpha stabilizer, so as to raise the level of hemoglobin relative to a baseline hemoglobin level in a patient, while mimicking the diurnal variation of serum EPO levels in healthy individuals, wherein the HIF prolyl hydroxylase inhibitor or a HIF-alpha stabilizer is a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, and Metabolite 2 or a pharmaceutically acceptable salt, solvate, or hydrate thereof.

In certain embodiments, provided herein are methods for treating a disease or condition related to diminished endogenous production of erythropoietin (EPO), comprising administering to a patient having a disease or condition related to diminished endogenous production of EPO a sufficient number of successive doses of a HIF prolyl hydroxylase inhibitor or a HIF-alpha stabilizer so as to raise the level of hemoglobin relative to a baseline hemoglobin level in a patient, wherein the time period between the administration of at least one of said successive doses and the administration of the immediately preceding dose is a sufficient time period to permit the level of serum EPO in a patient to return to about baseline serum EPO level, wherein the HIF prolyl hydroxylase inhibitor or a HIF-alpha stabilizer is a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, and Metabolite 2 or a pharmaceutically acceptable salt, solvate, or hydrate thereof. In certain such embodiments, the cardiovascular side-effects and risk of thromboembolic events associated with administration of exogenous EPO are minimized.

In certain embodiments, provided herein are methods for treating a disease or condition related to diminished endogenous production of erythropoietin (EPO), comprising administering to a patient having a disease or condition related to diminished endogenous production of EPO a sufficient number of successive doses of a HIF prolyl hydroxylase inhibitor or a HIF-alpha stabilizer so as to raise the level of hemoglobin relative to a baseline hemoglobin level in a patient, wherein prior to the addition of one or more doses following the initial dose the level of serum EPO returns to about a baseline level, wherein the HIF prolyl hydroxylase inhibitor or a HIF-alpha stabilizer is a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, and Metabolite 2 or a pharmaceutically acceptable salt, solvate, or hydrate thereof. In certain such embodiments, the cardiovascular side-effects and risk of thromboembolic events associated with administration of exogenous EPO are minimized.

In certain embodiments, provided herein are methods for treating a disease or condition related to diminished endogenous production of erythropoictin (EPO), comprising administering to a patient having a disease or condition related to diminished endogenous production of EPO a sufficient number of successive doses of a HIF prolyl hydroxylase inhibitor or a HIF-alpha stabilizer so as to raise the level of hemoglobin relative to a baseline hemoglobin level in a patient without significantly increasing the level of serum EPO relative to the baseline level of serum EPO, wherein the HIF prolyl hydroxylase inhibitor or a HIF-alpha stabilizer is a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, and Metabolite 2 or a pharmaceutically acceptable salt, solvate, or hydrate thereof. In certain such embodiments, the cardiovascular side-effects and risk of thromboembolic events associated with administration of exogenous EPO are minimized.

In certain such embodiments, the level of serum EPO returns to about baseline level within about one week, about six days, about five days, about four days, about three days, about two days, about twenty four hours, about eighteen hours, or about twelve hours of administering a dose of a HIF prolyl hydroxylase inhibitor or HIF-alpha stabilizer disclosed herein.

In certain embodiments, the level of serum EPO returns to within about 5 mIU/mL, about 4 mIU/mL, about 3 mIU/mL, about 2 mIU/mL, or about 1 mIU/mL of the baseline level of EPO.

In certain embodiments, the level of hemoglobin is raised by between about 0.1 and about 1.0 g/dL over a period of one week relative to the baseline hemoglobin level. In certain such embodiments, the level of hemoglobin is raised by about 0.1 g/dL over a period of one week relative to the baseline hemoglobin level.

In certain embodiments, the level of hemoglobin is raised by between about 0.1 and about 1.0 g/dL over a period of two weeks relative to the baseline hemoglobin level. In certain such embodiments, the level of hemoglobin is raised by about 0.1 g/dL over a period of two weeks relative to the baseline hemoglobin level.

In certain embodiments, the level of hemoglobin is raised by between about 0.1 and about 1.0 g/dL over a period of three weeks relative to the baseline hemoglobin level. In certain such embodiments, the level of hemoglobin is raised by about 0.6 g dL over a period of three weeks relative to the baseline hemoglobin level.

In certain embodiments, the level of hemoglobin is raised by between about 0.1 and about 1.0 g/dL over a period of four weeks relative to the baseline hemoglobin level. In certain such embodiments, the level of hemoglobin is raised by about 0.6 g/dL over a period of four weeks relative to the baseline hemoglobin level.

In certain embodiments, the disease or condition is anemia. In certain such embodiments, the anemia is anemia secondary to chronic kidney disease (CKD). In certain such embodiments, the chronic kidney disease is stage 3, 4, or 5 chronic kidney disease. In certain such embodiments, the chronic kidney disease is pre-dialysis chronic kidney disease.

In certain embodiments, the HIF prolyl hydroxylase inhibitor or HIF-alpha stabilizer is administered once daily. In certain embodiments, the HIF prolyl hydroxylase inhibitor or HIF-alpha stabilizer is administered orally.

In certain embodiments, the HIF prolyl hydroxylase inhibitor or HIF-alpha stabilizer is Compound 1 or a pharmaceutically acceptable salt, solvate or hydrate thereof.

In certain embodiments, the HIF prolyl hydroxylase inhibitor or HIF-alpha stabilizer is Compound 7 or a pharmaceutically acceptable salt, solvate or hydrate thereof.

In certain embodiments, provided herein is a compound as disclosed in section 5.2 for the treatment of a disease, condition, or disorder as disclosed in sections 5.4 and 5.7 at a dose as disclosed in 5.5, specifically at a dose suitable to mimic natural EPO diurnal pattern (see Section 5.3.1).

3.3 Iron Metabolism

Conventionally, it has been thought that in order to effectively treat a disease or condition related to diminished endogenous production of erythropoietin (EPO), such as anemia or anemia secondary to chronic kidney disease an increase in serum iron levels and an increase in transferrin saturation (TSAT) was desired. Surprisingly, it has been found that a disease or condition related to diminished endogenous production of erythropoietin (EPO) or a disease or condition related to deficiencies in endogenous hemoglobin production, such as anemia or anemia secondary to chronic kidney disease, may be effectively treated by raising total iron binding capacity while not increasing serum iron levels, thereby resulting in a decrease of transferrin saturation. Accordingly, unwanted side-effects associated with increased serum iron levels may be reduced or avoided.

In certain embodiments, provided herein is a method of treating a disease or condition related to diminished endogenous production of erythropoietin (EPO), comprising administering to a patient having a disease or condition related to diminished endogenous production of EPO a sufficient number of successive doses of a HIF prolyl hydroxylase inhibitor or a HIF-alpha stabilizer so as to raise the total iron binding capacity (TIBC) relative to a baseline TIBC in a patient, without significantly increasing the serum iron level relative to a baseline serum iron level.

In certain embodiments, provided herein is a method for treating or preventing anemia in a subject, wherein the method comprises administering to the subject a pharmaceutically effective amount of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, and Metabolite 2 or a pharmaceutically acceptable salt, solvate, or hydrate thereof. In certain, more specific embodiments, the pharmaceutically effective amount of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, and Metabolite 2 or a pharmaceutically acceptable salt, solvate, or hydrate thereof is suitable to raise TIBC at least about 10 µg/dL, at least about 20 µg/dL, at least about 30 µg/dL, at least about 40 µg/dL, at least about 50 µg/dL, or at least about 60 µg/dL relative to baseline TIBC and/or the level of hemoglobin by at least about 0.5 g/dL, by at least about 0.6 g/dL, by at least about 0.7 g/dL, by at least about 0.8 g/dL, by at least about 0.9 g/dL, by at least about 1.0 g/dL, by at least about 1.2 g/dL, or by at least about 1.5 g/dL relative to a baseline hemoglobin level in the patient while:
a) restoring or maintaining the diurnal pattern of EPO serum levels; and/or
b) maintaining pre-treatment levels of total iron (i.e., without increasing significantly the total iron levels); and/or
c) not significantly decreasing hepcidin levels.

In certain embodiments, provided herein are methods of treating a disease or condition related to diminished endogenous production of erythropoietin (EPO) while minimizing the cardiovascular side-effects and risk of thromboembolic events associated with increased serum iron levels, comprising administering to a patient having a disease or condition related to diminished endogenous production of EPO a sufficient number of successive doses of a HIF prolyl hydroxylase inhibitor or a HIF-alpha stabilizer so as to raise the total iron binding capacity (TIBC) relative to a baseline TIBC in a patient, without significantly increasing the serum iron level relative to a baseline serum iron level.

In certain embodiments, the transferrin saturation (TSAT) decreases relative to a baseline TSAT. In certain embodiments, the serum iron level decreases relative to a baseline scrum iron level.

In certain embodiments, the TIBC increases by at least about 10 µg/dL, at least about 20 µg/dL, at least about 30 µg/dL, at least about 40 µg/dL, at least about 50 µg/dL, or at least about 60 µg/dL relative to a baseline TIBC.

In certain embodiments, the TIBC increase relative to a baseline TIBC occurs over about 1 week, over about 2 weeks, over about 3 weeks, over about 4 weeks, over about 5 weeks, or over about 6 weeks.

In certain embodiments, the serum iron level increases by less than about 20 µg/dL, less than about 15 µg/dL, less than about 10 µg/dL, or less than about 5 µg/dL relative to a baseline serum iron level.

In certain embodiments, the disease or condition is anemia. In certain such embodiments, the anemia is anemia secondary to chronic kidney disease (CKD). In certain such embodiments, the chronic kidney disease is stage 3, 4, or 5 chronic kidney disease. In certain such embodiments, the chronic kidney disease is pre-dialysis chronic kidney disease.

In certain embodiments, the HIF prolyl hydroxylase inhibitor or HIF-alpha stabilizer is administered once daily.

In certain embodiments, the HIF prolyl hydroxylase inhibitor or HIF-alpha stabilizer is administered orally.

In certain embodiments, the HIF prolyl hydroxylase inhibitor or HIF-alpha stabilizer is a heterocyclic carboxamide. In certain such embodiments, the HIF prolyl hydroxylase inhibitor or HIF-alpha stabilizer is selected from a pyridine carboxamide, a quinoline carboxamide, and an isoquinoline carboxamide. In certain embodiments, the HIF prolyl hydroxylase inhibitor or HIF-alpha stabilizer is a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, and Metabolite 2 or a pharmaceutically acceptable salt, solvate, or hydrate thereof.

In certain embodiments, provided herein is a compound as disclosed in section 5.2 for the treatment of a disease, condition, or disorder as disclosed in sections 5.4 and 5.7 at a dose as disclosed in 5.5, specifically at a dose suitable to increase total iron binding capacity as described in Section 5.3.2.

3.4 Hepcidin

Surprisingly, it has been found that certain types of anemia, such as non-severe anemia secondary to chronic kidney disease, non-severe anemia secondary to chronic heart failure, or idiopathic anemia of aging, may be treated by raising serum hemoglobin levels without decreasing hepcidin expression. Accordingly, hepcidin expression is similar to the expression in healthy adults and functions to regulate iron transport normally.

In certain embodiments, provided herein is a method of treating a disease or condition selected from non-severe anemia secondary to chronic kidney disease, non-severe anemia secondary to congestive heart failure, and idiopathic anemia of aging, comprising administering to a patient having non-severe anemia secondary to chronic kidney disease, non-severe anemia secondary to congestive heart failure, or idiopathic anemia of aging a sufficient number of successive doses of a HIF prolyl hydroxylase inhibitor or a HIF-alpha stabilizer so as to raise the serum hemoglobin levels relative to a baseline serum hemoglobin level in a patient, without significantly decreasing hepcidin expression relative to a baseline hepcidin expression level.

In certain embodiments, the serum hemoglobin level is raised by between about 0.1 and about 1.0 g/dL over a period of one week relative to the baseline hemoglobin level. In certain such embodiments, the serum hemoglobin level is raised by about 0.1 g/dL over a period of one week relative to the baseline hemoglobin level.

In certain embodiments, the serum hemoglobin level is raised by between about 0.1 and about 1.0 g/dL over a period of two weeks relative to the baseline hemoglobin level. In certain such embodiments, the serum hemoglobin level is raised by about 0.1 g/dL over a period of two weeks relative to the baseline hemoglobin level.

In certain embodiments, the serum hemoglobin level is raised by between about 0.1 and about 1.0 g/dL over a period of three weeks relative to the baseline hemoglobin level. In certain such embodiments, the serum hemoglobin level is raised by about 0.5 g/dL over a period of three weeks relative to the baseline hemoglobin level.

In certain embodiments, the serum hemoglobin level is raised by between about 0.1 and about 1.0 g/dL over a period of four weeks relative to the baseline hemoglobin level. In certain such embodiments, the serum hemoglobin level is raised by about 0.6 g/dL over a period of four weeks relative to the baseline hemoglobin level.

In certain embodiments, the serum hemoglobin level is raised by between about 0.1 and about 1.0 g/dL over a period of five weeks relative to the baseline hemoglobin level. In certain such embodiments, the serum hemoglobin level is raised by about 0.6 g/dL over a period of five weeks relative to the baseline hemoglobin level.

In certain embodiments, the serum hemoglobin level is raised by between about 0.1 and about 1.0 g/dL over a period of six weeks relative to the baseline hemoglobin level. In certain such embodiments, the serum hemoglobin level is raised by about 0.6 g/dL over a period of six weeks relative to the baseline hemoglobin level.

In certain embodiments, hepcidin expression decreases less than about 20%, less than about 15%, less than about 10% relative to the baseline hepcidin expression level, less than about 5%, less than about 4%, less than about 3%, less than about 2%, or less than about 1% relative to the baseline hepcidin expression level.

In certain embodiments, the disease or condition is non-severe anemia secondary to chronic kidney disease. In certain embodiments, the disease or condition is non-severe congestive heart failure. In certain embodiments, the disease or condition is idiopathic anemia of aging.

In certain embodiments, the HIF prolyl hydroxylase inhibitor or HIF-alpha stabilizer is administered once daily. In certain embodiments, the HIF prolyl hydroxylase inhibitor or HIF-alpha stabilizer is administered orally.

In certain embodiments, the HIF prolyl hydroxylase inhibitor or HIF-alpha stabilizer is a heterocyclic carboxamide. In certain such embodiments, the HIF prolyl hydroxylase inhibitor or HIF-alpha stabilizer is selected from a pyridine carboxamide, a quinoline carboxamide, and an isoquinoline carboxamide.

In certain embodiments, the HIF prolyl hydroxylase inhibitor or HIF-alpha stabilizer is a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, and Metabolite 2 or a pharmaceutically acceptable salt, solvate, or hydrate thereof. In a specific embodiment, the HIF prolyl hydroxylase inhibitor or HIF-alpha stabilizer is Compound 1 or a pharmaceutically acceptable salt, solvate, or hydrate thereof. In a specific embodiment, the HIF prolyl hydroxylase inhibitor or HIF-alpha stabilizer is Compound 7 or a pharmaceutically acceptable salt, solvate, or hydrate thereof.

In certain embodiments, provided herein is a compound as disclosed in section 5.2 for the treatment of a disease, condition, or disorder as disclosed in sections 5.4 and 5.7 at a dose as disclosed in 5.5, specifically at a dose suitable to treat anemia without decreasing hepcidin levels as described in Section 5.3.3 and/or increase erythroferrone levels as described in Section 5.3.4.

4 BRIEF DESCRIPTION OF THE FIGURES

5 DETAILED DESCRIPTION

Figure 1A:
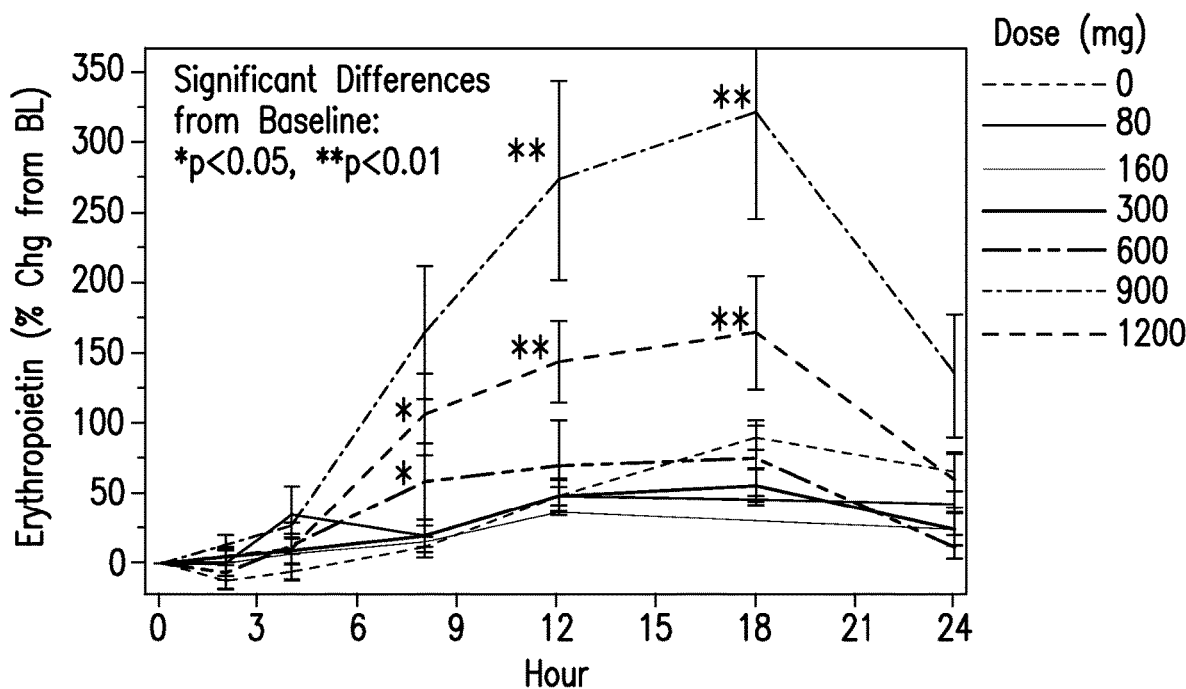
FIG. 1a shows the serum concentration of Compound 1 in healthy male adults over twenty-four hours.

In certain embodiments, provided herein is a method for treating or preventing anemia in a patient, wherein the method comprises administering to the patient a pharmaceutically effective amount of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, and Metabolite 2 or a pharmaceutically acceptable salt, solvate, or hydrate thereof, wherein the pharmaceutically effective amount is suitable to increase the level of hemoglobin by at least about 0.2 g/dL, 0.3 g/dL, 0.4 g/dL, 0.5 g/dL, by at least about 0.6 g/dL, by at least about 0.7 g/dL, by at least about 0.8 g/dL, by at least about 0.9 g/dL, by at least about 1.0 g/dL, by at least about 1.2 g/dL, or by at least about 1.5 g/dL relative to a baseline hemoglobin level in the patient while: a) restoring or maintaining the diurnal pattern of EPO serum levels; and/or b) increasing the total iron binding capacity; and/or c) increasing the total iron binding capacity without increasing significantly the total iron levels; and/or c) not significantly decreasing hepcidin levels.

5.1 Definitions and Abbreviations

In certain embodiments, as used throughout the description and claims of this specification the word "comprise"

and other forms of the word, such as "comprising" and "comprises," means including but not limited to, and is not intended to exclude, for example, other additives, components, integers, or steps. In certain embodiments, as used in the description and the appended claims, the singular forms "a," "an," and "the" include plural referents unless the context clearly dictates otherwise. Thus, for example, reference to "a composition" includes mixtures of two or more such compositions. In certain embodiments, "optional" or "optionally" means that the subsequently described event or circumstance can or cannot occur, and that the description includes instances where the event or circumstance occurs and instances where it does not As used herein, an "alkyl" group is a saturated straight chain or branched non-cyclic hydrocarbon having, for example, from 1 to 12 carbon atoms, 1 to 9 carbon atoms, 1 to 6 carbon atoms, 1 to 4 carbon atoms, or 2 to 6 carbon atoms. Representative alkyl groups include -methyl, -ethyl, -n-propyl, -n-butyl, -n-pentyl and -n-hexyl; while branched alkyls include -isopropyl, -sec-butyl, -iso-butyl, -tert-butyl, -iso-pentyl, 2-methylpentyl, 3-methylpentyl, 4-methylpentyl, 2,3-dimethylbutyl and the like.

$C_{1-6}$ alkyl units include the following non-limiting examples: methyl ($C_1$), ethyl ($C_2$), n-propyl ($C_3$), iso-propyl ($C_3$), n-butyl ($C_4$), sec-butyl ($C_4$), iso-butyl ($C_4$), tert-butyl ($C_4$), n-pentyl ($C_5$), tert-pentyl ($C_5$), neo-pentyl ($C_5$), iso-pentyl ($C_5$), sec-pentyl ($C_5$), 3-pentyl ($C_5$), n-hexyl ($C_6$), iso-hexyl ($C_6$), neo-hexyl ($C_6$), 3-methylpentyl ($C_6$), 4-methylpentyl ($C_6$), 3-methylpentan-2-yl ($C_6$), 4-methylpentan-2-yl ($C_6$), 2,3-dimethylbutyl ($C_6$), 3,3-dimethylbutan-2-yl ($C_6$), 2,3-dimethylbutan-2-yl ($C_6$), and the like.

As used herein, an "alkenyl" group is a partially unsaturated straight chain or branched non-cyclic hydrocarbon containing at least one carbon-carbon double bond and having, for example, from 1 to 6 carbon atoms. Representative alkenyl groups include propenyl and the like.

As used herein, an "alkynyl" group is a partially unsaturated straight chain or branched non-cyclic hydrocarbon containing at least one carbon-carbon triple bond and having, for example, from 2 to 6 carbon atoms. Representative alkynyl groups include propynyl, butynyl and the like.

As used herein, an "alkoxy" group is an alkyl-O— group in which the alkyl group is as defined herein. Representative alkoxy groups include methoxy, ethoxy, n-propoxy, iso-propoxy and n-butoxy.

As used herein, an "cycloalkyl" group is a saturated cyclic alkyl group of from 3 to 6 carbon atoms having a single cyclic ring. Representative cycloalkyl groups include cyclopropyl, cyclobutyl, and cyclopentyl.

As used herein, an "cycloalkenyl" group is a partially unsaturated cyclic alkyl group containing at least one carbon-carbon double bond and from 3 to 6 carbon atoms having a single cyclic ring. Representative cycloalkenyl groups include cyclopropenyl and cyclobutenyl.

As used herein, a "cycloalkoxy" group is a cycloalkyl-O— group in which the cycloalkyl group is as defined herein. Representative cycloalkoxy groups include cyclopropyloxy, cyclobutyloxy and cyclopentyloxy.

As used herein, a "haloalkyl" group is an alkyl group as defined herein above with one or more (e.g., 1 to 5) hydrogen atoms are replaced by halogen atoms. Representative haloalkyl groups include $CF_3$, $CHF_2$, $CH_2F$, $CCl_3$, $CF_3CH_2CH_2$ and $CF_3CF_2$.

As used herein, a "halocycloalkyl" group is a cycloalkyl group as defined herein above with one or more (e.g., 1 to 5) hydrogen atoms are replaced by halogen atoms. Representative halocycloalkyl groups include 2,2-difluorocyclopropyl, 2,2-dichlorocyclopropyl, 2,2-dibromocyclopropyl, tetrafluorocyclopropyl, 3,3-difluorocyclobutyl and 2,2,3,3-tetrafluorocyclobutyl.

As used herein, a "heterocycloalkyl" group is a saturated ring of 4 to 7 atoms, preferably 5 or 6 ring atoms, wherein 1 or 2 ring members are selected from the group consisting of O, S and NR" and the remaining atoms are carbon. There are no adjacent oxygen and/or sulfur atoms in the rings. Representative heterocycloalkyl groups are piperidyl, pyrrolidinyl, piperazinyl, morpholinyl, thiomorpholinyl, thiazolidinyl, 1,3-dioxolanyl, 1,4-dioxanyl, oxazolinyl, tetrahydrofuranyl, tetrahydrothiophenyl and tetrahydrothiopyranyl.

As used herein, an "aryl" group is an aromatic monocyclic or multi-cyclic ring system comprising 6 to 10 carbon atoms. Representative aryl groups include phenyl and naphthyl.

As used herein, a "heteroaryl" is a single ring, bicyclic or benzofused heteroaromatic group of 5 to 10 atoms comprised of 2 to 9 carbon atoms and 1 to 4 heteroatoms independently selected from the group consisting of N, O and S, provided that the rings do not include adjacent oxygen and/or sulfur atoms. N-oxides of the ring nitrogens are also included. Representative single-ring heteroaryl groups include pyridyl, oxazolyl, isoxazolyl, oxadiazolyl, furanyl, pyrrolyl, thienyl, imidazolyl, pyrazolyl, tetrazolyl, thiazolyl, isothiazolyl, thiadiazolyl, pyrazinyl, pyrimidyl, pyridazinyl and triazolyl. Representative bicyclic heteroaryl groups are naphthyridyl (e.g., 1,5 or 1,7), imidazopyridyl, pyridopyrimidinyl and 7-azaindolyl. Representative benzofused heteroaryl groups include indolyl, quinolyl, isoquinolyl, phthalazinyl, benzothienyl (i.e., thianaphthenyl), benzimidazolyl, benzofuranyl, benzoxazolyl, benzisoxazolyl, benzothiazolyl and benzofurazanyl. All positional isomers are contemplated, e.g., 2-pyridyl, 3-pyridyl and 4-pyridyl.

For the purposes of the present disclosure the terms "compound," "analog," and "composition of matter" stand equally well for the HIF prolyl hydroxylase enzyme inhibitors described herein, including all enantiomeric forms, diasteromeric forms, salts, tautomers, and the like. The compounds disclosed herein include all salt forms, for example, salts of both basic groups, inter alia, amines, as well as salts of acidic groups, inter alia, carboxylic acids. The following are non-limiting examples of anions that can form pharmaceutically acceptable salts with basic groups: chloride, bromide, iodide, sulfate, bisulfate, carbonate, bicarbonate, phosphate, formate, acetate, propionate, butyrate, pyruvate, lactate, oxalate, malonate, maleate, succinate, tartrate, fumarate, citrate, and the like. The following are non-limiting examples of cations that can form pharmaceutically acceptable salts of the anionic form of acidic substituent groups on the compounds described herein: sodium, lithium, potassium, calcium, magnesium, zinc, bismuth, and the like. The following are non-limiting examples of cations that can form pharmaceutically acceptable salts of the anionic form of phenolic, aryl alcohol, or heteroaryl alcohol substituent groups on the compounds described herein: sodium, lithium, and potassium. In certain embodiments, terms "compound," "analog," and "composition of matter" are used interchangeably throughout the present specification.

It should be noted that if there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

As used herein, the term "anemia" is art-recognized and is defined by hemoglobin threshold as follows:

| Age or Gender Group | Hemoglobin Threshold (g/dL) |
| --- | --- |
| Children (0.50-4.99 yrs.) | 11.0 |
| Children (5.00-11.99 yrs.) | 11.5 |
| Children (12.00-14.99 yrs.) | 12.0 |
| Non-pregnant Women (≥15.00 yrs) | 12.0 |
| Pregnant Women | 11.0 |
| Men (≥15.00 yrs) | 13.0 |

Anemia may be chronic (e.g., anemia secondary to chronic kidney disease, anemia secondary to chronic heart failure, idiopathic anemia of aging, anemia of chronic disease, such as inflammatory bowel disease or rheumatoid arthritis, myelodysplastic syndrome, bone marrow fibrosis, and other aplastic or dysplastic anemias), subacute (e.g., chemotherapy induced anemia, such as chemotherapy for treating cancer, hepatitis C, or other chronic disease that reduces bone marrow production), acute (e.g., blood loss from injury or surgery), nutrition related (e.g., iron deficiency or vitamin B12 deficiency), or hemaglobinpathies (e.g., sickle cell disease, thalassemia, etc.), or anemia due to prematurity, or anemia due to autologous blood donation.

As used herein the term "non-severe anemia" refers to a patient having anemia wherein the hemoglobin is at least 9.0 g/dL. In certain such embodiments, non-severe anemia refers to anemia in a patient, wherein the patient does not require a transfusion.

As used herein, the term "dose(s)" means a quantity of the compound or a pharmaceutically acceptable salt, solvate, or hydrate thereof to be administered at one time. A dose may comprise a single unit dosage form, or alternatively may comprise more than a single unit dosage form (e.g., a single dose may comprise two tablets), or even less than a single unit dosage form (e.g., a single dose may comprise half of a tablet). Accordingly, if the compound is administered at a daily dose of 450 mg, once daily, then the dose of compound may be three tablets, each comprising 150 mg of compound administered once daily.

As used herein, the term "daily dose" means a quantity of the compound, or a pharmaceutically acceptable salt, solvate, or hydrate thereof that is administered in a 24 hour period. Accordingly, a daily dose may be administered all at once (i.e., once daily dosing) or alternatively the daily dosing may be divided such that administration of the compound is twice daily, three times daily, or even four times daily. When a daily dose is administered every day without interruption, the dosing is referred to as "continuous" dosing.

As used herein, the term "unit dosage form(s)" includes tablets; caplets; capsules, such as soft elastic gelatin capsules; sachets; cachets; troches; lozenges; dispersions; powders; solutions; gels; liquid dosage forms suitable for oral or mucosal administration to a patient, including suspensions (e.g., aqueous or non-aqueous liquid suspensions), emulsions (e.g., oil-in-water emulsions, or a water-in-oil liquid emulsion), solutions, and elixirs; and sterile solids (e.g., crystalline or amorphous solids) that can be reconstituted to provide liquid dosage forms suitable for oral or parenteral administration to a patient. The unit dosage form does not necessarily have to be administered as a single dose nor does a single unit dosage form necessarily constitute an entire dose.

As used herein, an "effective amount" refers to that amount of a compound or a pharmaceutically acceptable salt, solvate or hydrate thereof sufficient to provide a therapeutic benefit in the treatment of the disease or to delay or minimize symptoms associated with the disease. Certain preferred effective amounts are described herein. In certain embodiments, the compound is a compound disclosed herein.

As used herein, the terms "prevent", "preventing" and "prevention" are art-recognized, and when used in relation to a condition, such as a local recurrence (e.g., pain), a disease such as cancer, a syndrome complex such as heart failure or any other medical condition, is well understood in the art, and includes administration of a compound provided herein or a pharmaceutically acceptable salt, solvate or hydrate thereof, which reduces the frequency of, or delays the onset of, symptoms of a medical condition in a subject relative to a subject which does not receive the composition. In certain embodiments, the compound is a compound that is not disclosed herein. In certain embodiments, the condition is a disease or condition related to diminished endogenous production of erythropoietin (EPO) or a disease or condition related to deficiencies in endogenous hemoglobin production, such as anemia or anemia secondary to chronic kidney disease.

As used herein, the terms "treat", "treating" and "treatment" refer to the reversing, reducing, or arresting the symptoms, clinical signs, and underlying pathology of a condition in manner to improve or stabilize a subject's condition. The terms "treat" and "treatment" also refer to the eradication or amelioration of the disease or symptoms associated with the disease. In certain embodiments, such terms refer to minimizing the spread or worsening of the disease resulting from the administration of a compound provided herein or a pharmaceutically acceptable salt, solvate or hydrate thereof to a patient with such a disease.

As used herein, the term "pharmaceutically acceptable salt" refers to a salt prepared from pharmaceutically acceptable non-toxic acids or bases including inorganic acids and bases and organic acids and bases. Suitable pharmaceutically acceptable base addition salts for a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, and Metabolite 2 include, but are not limited to, sodium, lithium, potassium, calcium, magnesium, zinc, bismuth, ammonium (including alkyl substituted ammonium), amino acids (e.g., lysine, omithine, arginine, or glutamine), tromethamine, and meglumine. Suitable non-toxic acids include, but are not limited to, inorganic and organic acids such as acetic, alginic, anthranilic, benzenesulfonic, benzoic, camphorsulfonic, citric, ethanesulfonic, formic, fumaric, furoic, galacturonic, gluconic, glucuronic, glutamic, glycolic, hydrobromic, hydrochloric, isethionic, lactic, maleic, malic, mandelic, methanesulfonic, mucic, nitric, pamoic, pantothenic, phenylacetic, phosphoric, propionic, salicylic, stearic, succinic, sulfanilic, sulfuric, tartaric acid, and p-toluenesulfonic acid. Other examples of salts are well known in the art, see, e.g., Remington's Pharmaceutical Sciences, 22nd ed., Pharmaceutical Press, (2012).

In certain embodiments, "pharmaceutically acceptable" is meant a material that is not biologically or otherwise undesirable, i.e., the material can be administered to an individual along with the relevant active compound without causing clinically unacceptable biological effects or interacting in a deleterious manner with any of the other components of the pharmaceutical composition in which it is contained.

As used herein, the term "hydrate" means a compound provided herein or a pharmaceutically acceptable salt thereof, that further includes a stoichiometric or non-stoichiometric amount of water bound by non-covalent intermolecular forces.

As used herein, the term "solvate" means a compound provided herein or a pharmaceutically acceptable salt thereof, that further includes a stoichiometric or non-stoichiometric amount of a solvent, other than water, bound by non-covalent intermolecular forces.

As used herein, and unless otherwise indicated, the term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 50%, 20%, 15%, 10%, 9%, 8%, 7%, 6%, 5%, 4%, 3%, 2%, 1%, 0.5%, or 0.05% of a given value or range. In certain embodiments, ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed, then "less than or equal to" the value, "greater than or equal to the value," and possible ranges between values are also disclosed, as appropriately understood by the skilled artisan. For example, if the value "10" is disclosed, then "less than or equal to 10" as well as "greater than or equal to 10" is also disclosed. It is also understood that throughout the application data are provided in a number of different formats and that this data represent endpoints and starting points and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

In certain embodiments, the term subject or patient can refer to a mammal, such as a human, mouse, dog, donkey, horse, rat, guinea pig, bird, or monkey. In specific embodiments, a subject or a patient is a human subject or patient.

In certain embodiments, a compound provided herein is Compound 1, namely {[5-(3-chlorophenyl)-3-hydroxypyridine-2-carbonyl]amino}acetic acid having the structure

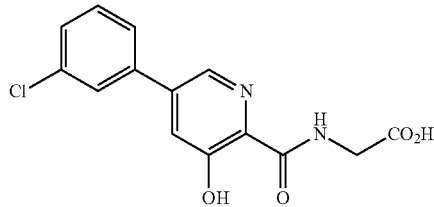 [SMILES: O=C(O)CNC(=O)c1ncc(-c2cccc(Cl)c2)cc1O]

In certain embodiments, the compound may be {[5-(3-chlorophenyl)-3-hydroxypyridine-2-carbonyl]amino}acetic acid, while in certain alternative embodiments, the compound may be a pharmaceutically acceptable salt of {[5-(3-chlorophenyl)-3-hydroxypyridine-2-carbonyl]amino}acetic acid. In certain alternative embodiments, the compound may be a solvate of {[5-(3-chlorophenyl)-3-hydroxypyridine-2-carbonyl]amino}acetic acid. In certain alternative embodiments, the compound may be a hydrate of {[5-(3-chlorophenyl)-3-hydroxypyridine-2-carbonyl]amino}acetic acid. In certain preferred embodiments, the invention relates to the compound in its parent form (i.e., not a salt, solvate, or hydrate). In certain alternative preferred embodiments, the invention relates to the compound or a pharmaceutically acceptable salt thereof.

As used herein, the term "HIF prolyl hydroxylase" is art-recognized and may be abbreviated as "PHD". HIF prolyl hydroxylase is also known as "prolyl hydroxylase domain-containing protein" which may be abbreviated as "PHD". In this regard, there are three different PHD isoforms, PHD1, PHD2, and PHD3, also referred to as EGLN2, EGLN1, and EGLN3, or HPH3, HPH2, and HPH1, respectively. In certain embodiments. HIF prolyl hydroxylase may refer to a particular target of the enzyme (e.g., HIF-1α prolyl hydroxylase. HIF-2α prolyl hydroxylase, and/or HIF-3α prolyl hydroxylase).

5.2 Compounds

In certain embodiments, a compound for use with the methods provided herein is a modulator of a HIF prolyl hydroxylase. In more specific embodiments, a compound for use with the methods provided herein is a modulator of a HIF-1-alpha prolyl hydroxylase. In other, more specific embodiments, a compound for use with the methods provided herein is a modulator of a HIF-2-alpha prolyl hydroxylase. In certain, even more specific embodiments, a compound for use with the methods provided herein is a modulator of a HIF-2-alpha prolyl hydroxylase that is more active against HIF-2-alpha prolyl hydroxylase than HIF-1-alpha prolyl hydroxylase by at least 10%, 20%, 25%, 30%, 40%, 50%, 60%, 70%, 75%, 80%, 90%, 100%, 125%, 150%, 175%, 200%, 250%, 500%, 750%, or at least 1000%. Thus, in certain embodiments, a compound provided herein for use with the methods provided herein preferentially stabilizes HIF-2-alpha over HIF-1-alpha. To determine preferential stabilization of HIF-2-alpha over HIF-1-alpha, the concentrations of HIF-1-alpha and HIF-2-alpha in a subject with and without test compound can be determined using a HIF-1-alpha and a HIF-2-alpha ELISA kit. Care should be taken that the primary antibodies in the respective kits are not cross-reactive with the other HIF (i.e., the primary antibody against HIF-1-alpha reacts immunospecifically with HIF-1-alpha and does not cross-react with HIF-2-alpha; the primary antibody against HIF-2-alpha reacts immunospecifically with HIF-2-alpha and does not cross-react with HIF-1-alpha).

In certain embodiments, a compound of the invention which is a HIF prolyl hydroxylase inhibitor or a HIF-alpha stabilizer is a heterocyclic carboxamide. In certain such embodiments, the heterocyclic carboxamide is selected from a pyridyl carboxamide, a quinoline carboxamide, and an isoquinoline carboxamide.

In certain embodiments, the HIF prolyl hydroxylase inhibitor or HIF-alpha stabilizer has a structure of Formula (I):

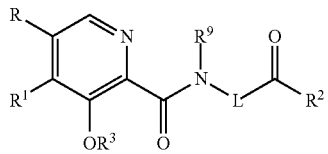

Formula (I)

or a pharmaceutically acceptable salt, solvate or hydrate thereof, wherein
R and $R^1$ are each independently:
(i) hydrogen
(ii) substituted or unsubstituted phenyl; or
(iii) substituted or unsubstituted heteroaryl;
said substitution selected from:
(i) $C_1$-$C_4$ alkyl;
(ii) $C_3$-$C_4$ cycloalkyl;
(iii) $C_1$-$C_4$ alkoxy;
(iv) $C_3$-$C_4$ cycloalkoxy;
(v) $C_1$-$C_4$ haloalkyl;
(vi) $C_3$-$C_4$ halocycloalkyl;
(vii) halogen;
(viii) cyano;
(ix) NHC(O)$R^4$;
(x) C(O)N$R^{5a}R^{5b}$; and
(xi) heteroaryl; or
(xii) two substituents are taken together to form a fused ring having from 5 to 7 atoms:
$R^4$ is a $C_1$-$C_4$ alkyl or $C_3$-$C_4$ cycloalkyl;
$R^{5a}$ and $R^{5b}$ are each independently selected from:
(i) hydrogen;
(ii) $C_1$-$C_4$ alkyl;
(iii) $C_3$-$C_4$ cycloalkyl; or
(iv) $R^{5a}$ and $R^{5b}$ are taken together to form a ring having from 3 to 7 atoms;
$R^2$ is selected from:
(i) $OR^6$
(ii) $NR^{7a}R^{7b}$; and
$R^6$ is selected from hydrogen and $C_1$-$C_4$ alkyl or $C_3$-$C_4$ cycloalkyl;
$R^{7a}$ and $R^{7b}$ are each independently selected from:
(i) hydrogen;
(ii) $C_1$-$C_4$ alkyl or $C_3$-$C_4$ cycloalkyl; or
(iii) $R^{7a}$ and $R^{7b}$ are taken together to form a ring having from 3 to 7 atoms;
$R^3$ is selected from hydrogen, methyl, and ethyl;
L is a linking unit having a structure —[C($R^{8a}R^{8b}$)]$_n$—
$R^{8a}$ and $R^{8b}$ are each independently selected from hydrogen, methyl and ethyl;
n is an integer from 1 to 3; and
$R^9$ is selected from hydrogen and methyl.

In certain, more specific embodiments, in Formula (I) R and $R^1$ are not both hydrogen.

In certain embodiments, the HIF prolyl hydroxylase inhibitor or HIF-alpha stabilizer has a structure of Formula (II):

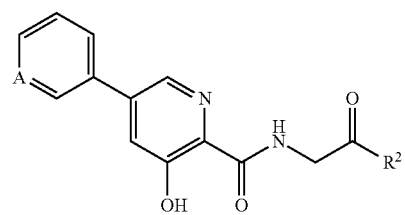

Formula (II)

or a pharmaceutically acceptable salt, solvate or hydrate thereof, wherein

A is selected from the group consisting of CR', N, $N^+$—$O^-$ and $N^+$($C_1$-$C_6$ alkyl);

R' is selected from the group consisting of H, $C_1$-$C_6$ alkyl, $C_3$-$C_6$ cycloalkyl, $C_2$-$C_6$ alkenyl, $C_3$-$C_6$ cycloalkenyl, $C_2$-$C_6$ alkynyl, $C_4$-$C_7$ heterocycloalkyl, $C_6$-$C_{10}$ aryl, $C_5$-$C_{10}$ heteroaryl, $NH_2$, NHR", $N(R")_2$, NHC(O)R", NR"C(O)R", F, Cl, Br, I, OH, OR", SH, SR", S(O)R", S(O)$_2$R", S(O)NHR", S(O)$_2$NHR", S(O)N$R"_2$, S(O)$_2$N$R"_2$, C(O)R", $CO_2$H, $CO_2$R", C(O)$NH_2$, C(O)NHR", C(O)N$R"_2$, CN, $CH_2$CN, $CF_3$, $CHF_2$, $CH_2$F, NH(CN), N(CN)$_2$, CH(CN)$_2$, C(CN)$_3$; and R" is independently selected from the group consisting of $C_1$-$C_6$ alkyl, $C_3$-$C_6$ cycloalkyl, $C_4$-$C_7$ heterocycloalkyl, $C_6$-$C_{10}$ aryl and $C_5$-$C_{10}$ heteroaryl; and wherein $C_1$-$C_6$ alkyl, $C_3$-$C_6$ cycloalkyl, or $C_4$-$C_7$ heterocycloalkyl are optionally substituted with oxo, $NH_2$, NHR", $N(R")_2$, F, Cl, Br, I, OH, OR", SH, SR", S(O)R", S(O)$_2$R", S(O)NHR", S(O)$_2$NHR", S(O)N$R"_2$, S(O)$_2$N$R"_2$, C(O)R", $CO_2$H, $CO_2$R", C(O)$NH_2$, C(O)NHR", C(O)N$R"_2$, CN, $CH_2$CN, $CF_3$, $CHF_2$, $CH_2$F, NH(CN), N(CN)$_2$, CH(CN)$_2$, C(CN)$_3$; and wherein $C_6$-$C_{10}$ aryl or $C_5$-$C_{10}$ heteroaryl are optionally substituted with $C_1$-$C_6$ alkyl, $C_3$-$C_6$ cycloalkyl, $C_2$-$C_6$, alkenyl, $C_3$-$C_6$ cycloalkenyl, $C_2$-$C_6$ alkynyl, $C_4$-$C_7$ heterocycloalkyl, $C_6$ aryl, $C_3$-$C_6$ heteroaryl, $NH_2$, NHR", $N(R")_2$, NHC(O)R", NR"C(O)R", F, Cl, Br, I, OH, OR", SH, SR", S(O)R", S(O)$_2$R", S(O)NHR", S(O)$_2$NHR", S(O)N$R"_2$, S(O)$_2$N$R"_2$, C(O)R", $CO_2$H, $CO_2$R", C(O)$NH_2$, C(O)NHR", C(O)N$R"_2$, CN, $CH_2$CN, $CF_3$, $CHF_2$, $CH_2$F, NH(CN), N(CN)$_2$, CH(CN)$_2$, or C(CN)$_3$; and wherein two R" groups on a nitrogen can be taken together to form a ring having from 2 to 7 carbon atoms and from 1 to 3 heteroatoms chosen from nitrogen, oxygen and sulfur including the nitrogen atom to which the two R" groups are bonded;

$R^2$ is selected from:
(i) $OR^6$;
(ii) $NR^{7a}R^{7b}$; and
$R^6$ is selected from hydrogen and $C_1$-$C_4$ alkyl or $C_3$-$C_4$ cycloalkyl;
$R^{7a}$ and $R^{7b}$ are each independently selected from:
(i) hydrogen;
(ii) $C_1$-$C_4$ alkyl or $C_3$-$C_4$ cycloalkyl; or
(iii) $R^{7a}$ and $R^{7b}$ are taken together to form a ring having from 3 to 7 atoms.

In certain embodiments, the HIF stabilizer is a compound having a structure of Formula (III)

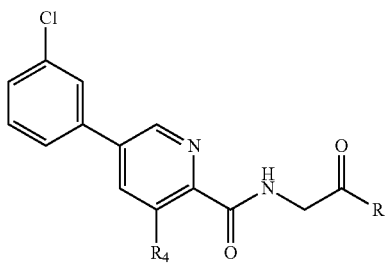

Formula (III)

or a pharmaceutically acceptable salt, solvate or hydrate thereof, wherein
R is chosen from
(i) —$OR^1$; or
(ii) —$NR^2R^3$; or
(iii) —$OM^1$;
$R^1$ is:
(i) hydrogen; or
(ii) $C_1$-$C_6$ alkyl or $C_3$-$C_6$ cycloalkyl;
$R^2$ and $R^3$ are each independently selected from:
(i) hydrogen;
(ii) $C_1$-$C_4$ alkyl or $C_3$-$C_4$ cycloalkyl; or
(iii) $R^2$ and $R^3$ can be taken together to form a ring having from 2 to 7 carbon atoms and from 1 to 3 heteroatoms chosen from nitrogen, oxygen and sulfur including the nitrogen atom to which $R^2$ and $R^3$ are bonded; and
$M^1$ is a cation; and
$R^4$ is:
(i) —OH; or
(ii) —$OM^2$; and
$M^2$ is a cation.

In certain embodiments, the HIF stabilizer is a compound having a structure of Formula (IV)

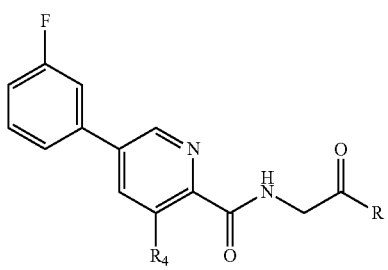

Formula (IV)

or a pharmaceutically acceptable salt, solvate or hydrate thereof, wherein
R is chosen from
(i) —$OR^1$; or
(ii) —$NR^2R^3$; or
(iii) —$OM_1$;
$R^1$ is:
(i) hydrogen; or
(ii) $C_1$-$C_6$ alkyl or $C_3$-$C_6$ cycloalkyl;
$R^2$ and $R^3$ are each independently selected from:
(i) hydrogen;
(ii) $C_1$-$C_4$ alkyl or $C_3$-$C_4$ cycloalkyl; or
(iii) $R^2$ and $R^3$ can be taken together to form a ring having from 2 to 7 carbon atoms and from 1 to 3 heteroatoms chosen from nitrogen, oxygen and sulfur including the nitrogen atom to which $R^2$ and $R^3$ are bonded; and
$M^1$ is a cation; and
$R^4$ is:
(i) —OH; or
(ii) —$OM^2$; and
$M^2$ is a cation.

HIF prolyl hydroxylase inhibitor compounds described herein are unsubstituted or substituted 3-hydroxy-pyridine-2-carboxamides, having the structure shown in Formula (V) below:

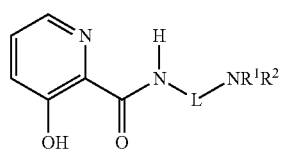

Formula (V)

and pharmaceutically acceptable salts and tautomers thereof, wherein: L is $C_{1-6}$ alkyl; and wherein $R^1$ and $R^2$ are independently H or $C_{1-6}$ alkyl.

In certain embodiments, the HIF prolyl hydroxylase inhibitor or HIF-alpha stabilizer is {[5-(3-chlorophenyl)-3-hydroxypyridine-2-carbonyl]amino}acetic acid (Compound 1):

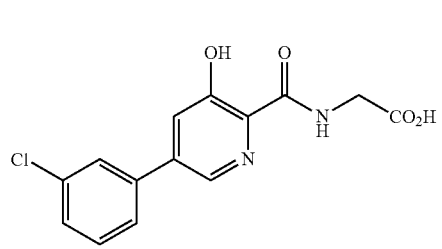

Compound 1 or a pharmaceutically acceptable salt, solvate or hydrate thereof.

In certain embodiments, the HIF stabilizer is Compound 2 having the structure:

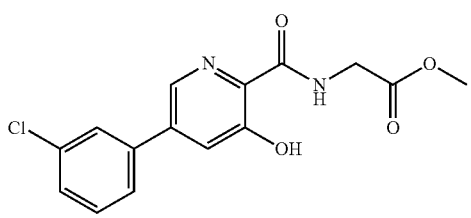

Compound 2 or a pharmaceutically acceptable salt, solvate or hydrate thereof.

In certain embodiments, the HIF stabilizer is Compound 3 having a structure

Compound 3

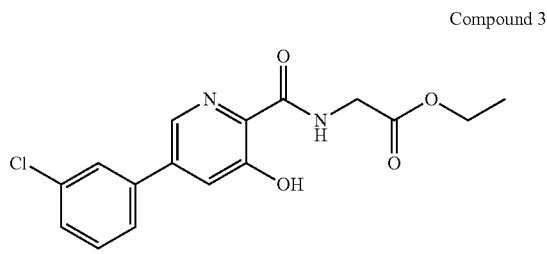 [SMILES: CCOC(=O)CNC(=O)c1ncc(-c2cccc(Cl)c2)cc1O]

or a pharmaceutically acceptable salt, solvate or hydrate thereof.

In certain embodiments, the HIF stabilizer is Compound 4 having a structure

Compound 4

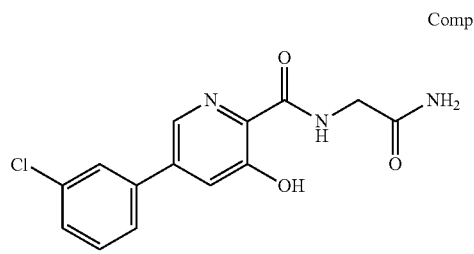

or a pharmaceutically acceptable salt, solvate or hydrate thereof.

In certain embodiments, the HIF stabilizer is Compound 5 having the structure

Compound 5

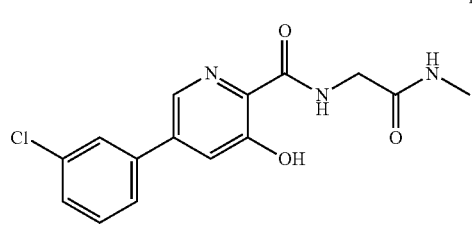

or a pharmaceutically acceptable salt, solvate or hydrate thereof.

In certain embodiments, the HIF stabilizer is Compound 6 having the structure

Compound 6

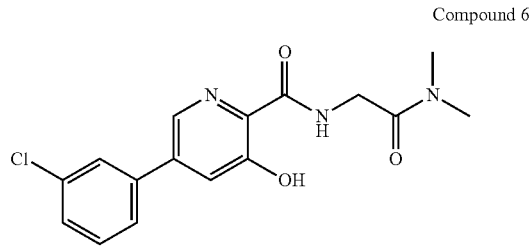 [SMILES: CN(C)C(=O)CNC(=O)c1ncc(-c2cccc(Cl)c2)cc1O]

or a pharmaceutically acceptable salt, solvate or hydrate thereof.

In certain embodiments, the HIF prolyl hydroxylase inhibitor or HIF-alpha stabilizer is Compound 7 having the structure:

Compound 7

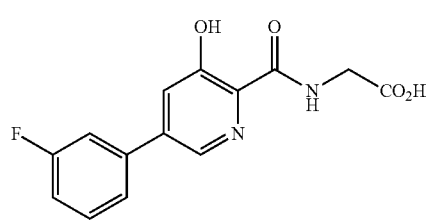

or a pharmaceutically acceptable salt, solvate or hydrate thereof.

In certain embodiments, the HIF stabilizer is Compound 8 having the structure:

Compound 8

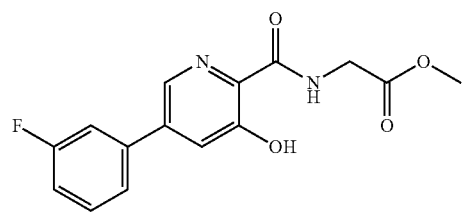

or a pharmaceutically acceptable salt, solvate or hydrate thereof.

In certain embodiments, the HIF stabilizer is Compound 9 having a structure

Compound 9

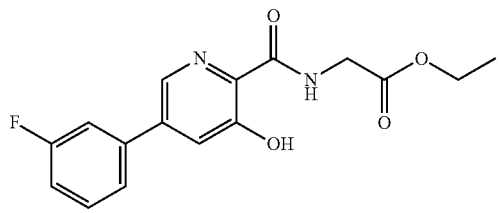

or a pharmaceutically acceptable salt, solvate or hydrate thereof.

In certain embodiments, the HIF stabilizer is Compound 10 having a structure

Compound 10

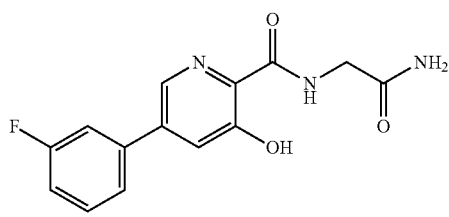

or a pharmaceutically acceptable salt, solvate or hydrate thereof.

In certain embodiments, the HIF stabilizer is Compound 11 having the structure

Compound 11

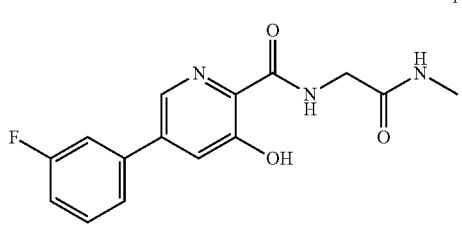

or a pharmaceutically acceptable salt, solvate or hydrate thereof.

In certain embodiments, the HIF stabilizer is Compound 12 having the structure

Compound 12

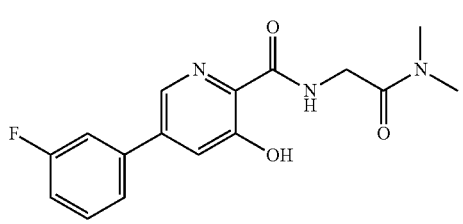

or a pharmaceutically acceptable salt, solvate or hydrate thereof.

In certain embodiments, the HIF stabilizer is Compound 13 having the structure

Compound 13

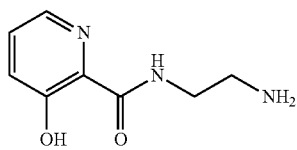

having a name N-(2-aminoethyl)-3-hydroxy-pyridine-2-carboxamide, including pharmaceutically acceptable salts and tautomers thereof. Tautomers of Compound 13 include the following:

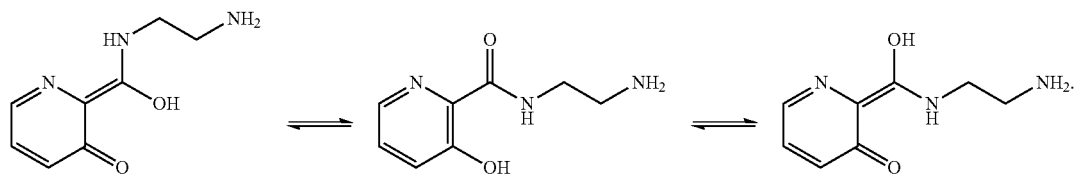 [SMILES: NCCN/C(O)=C1\N=CC=CC1=O ; NCCNC(=O)c1ncccc1O ; NCCN/C(O)=C1/N=CC=CC1=O]

In certain embodiments, a metabolite of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, or Compound 13 can be used with the methods provided herein. In certain more specific embodiments, such a metabolite is a phenolic glucuronide or an acyl-glucuronide.

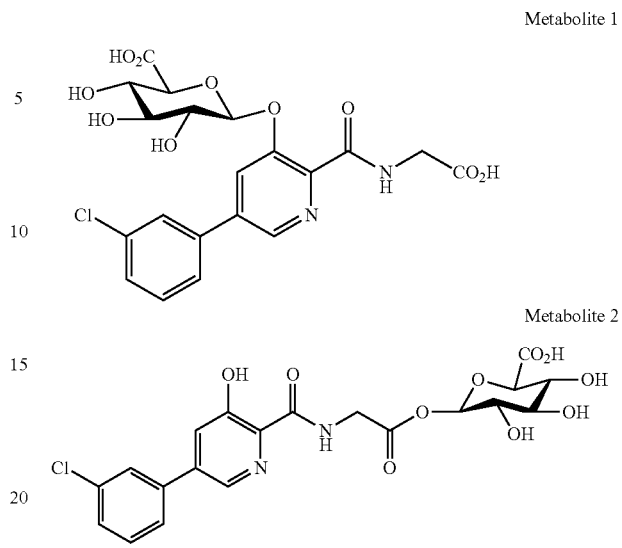

Compound 13 can be prepared using reagents and methods known in the art, including the methods provided in Chinese Patent Application Publication No. CN 85107182 A, published on Apr. 8, 1987, and German Patent Application Publication No. DE 3530046 A1, published on Mar. 13, 1986, the entire contents of each of which are incorporated herein by reference.

5.3 Method of Treatment and Prevention

In certain embodiments, provided herein is a method for treating and/or preventing anemia, such as anemia secondary to chronic kidney disease, comprising administering to a patient having anemia an effective amount of a HIF prolyl hydroxylase inhibitor or a HIF-alpha stabilizer, such as a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2, or a pharmaceutically acceptable salt, solvate, or hydrate thereof, wherein a daily dose comprises about 100 mg, about 110 mg, about 120 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, about 260 mg, about 270 mg, about 280 mg, about 290 mg, about 300 mg, about 310 mg, about 320 mg, about 330 mg, about 340 mg, about 350 mg, about 360 mg, about 370 mg, about 380 mg, about 390 mg, about 400 mg, about 410 mg, about 420 mg, about 430 mg, about 440 mg, about 450 mg, about 600 mg, or about 750 mg of the compound, pharmaceutically acceptable salt, solvate, or hydrate thereof. In certain such embodiments, the daily dose is about 150 mg, about 300 mg, about 450 mg, or about 600 mg. Such daily doses may be administered orally, once daily, twice daily, or three times daily, preferably once daily. In certain embodiments, the daily dose is 2 mg/kg, 2 mg/kg, 2.2 mg/kg, 2.3 mg/kg, 2.4 mg/kg, 2.5 mg/kg, 2.6 mg/kg, 2.7 mg/kg, 2.8 mg/kg, 2.9 mg/kg, 3 mg/kg, 3.1 mg/kg, 3.2 mg/kg, 3.3 mg/kg, 3.4 mg/kg, 3.5 mg/kg, 3.6 mg/kg, 3.7 mg/kg, 3.8 mg/kg, 3.9 mg/kg, or 4 mg/kg. In certain embodiments, provided herein is a HIF prolyl hydroxylase inhibitor or a HIF-alpha stabilizer, such as a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2, or a pharmaceutically acceptable salt, solvate, or hydrate thereof, for use in a method of treating anemia, such as anemia secondary to chronic kidney disease, comprising administering the HIF prolyl hydroxylase inhibitor of HIF-alpha stabilizer at a daily dose of about 100 mg, about 110 mg, about 120 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, about 260 mg, about 270 mg, about 280 mg, about 290 mg, about 300 mg, about 310 mg, about 320 mg, about 330 mg, about 340 mg, about 350 mg, about 360 mg, about 370 mg, about 380 mg, about 390 mg, about 400 mg, about 410 mg, about 420 mg, about 430 mg, about 440 mg, about 450 mg, about 600 mg, or about 750 mg of the compound, pharmaceutically acceptable salt, solvate, or hydrate thereof. In certain such embodiments, the daily dose is about 150 mg, about 300 mg, about 450 mg, or about 600 mg. Such daily doses may be administered orally, once daily, twice daily, or three times daily, preferably once daily. In certain embodiments, the daily dose is 2 mg/kg, 2.1 mg/kg, 2.2 mg/kg, 2.3 mg/kg, 2.4 mg/kg, 2.5 mg/kg, 2.6 mg/kg, 2.7 mg/kg, 2.8 mg/kg, 2.9 mg/kg, 3 mg/kg, 3.1 mg/kg, 3.2 mg/kg, 3.3 mg/kg, 3.4 mg/kg, 3.5 mg/kg, 3.6 mg/kg, 3.7 mg/kg, 3.8 mg/kg, 3.9 mg/kg, or 4 mg/kg. In certain embodiments, the compound is {[5-(3-chlorophenyl)-3-hydroxypyridine-2-carbonyl]amino}acetic acid. In certain embodiments, the compound is a pharmaceutically acceptable salt of {[5-(5-(3-chlorophenyl)-3-hydroxypyridine-2-carbonyl]amino}acetic acid. In certain embodiments, the compound is a solvate of {[5-(3-chlorophenyl)-3-hydroxypyridine-2-carbonyl]amino}acetic acid. In certain embodiments, the compound is a hydrate of {[5-(3-chlorophenyl)-3-hydroxypyridine-2-carbonyl]amino}acetic acid. In certain embodiments, the compound is 2-(5-(3-fluorophenyl)-3-hydroxypicolinamido)acetic acid. In certain embodiments, the compound is a pharmaceutically acceptable salt of 2-(5-(3-fluorophenyl)-3-hydroxypicolinamido)acetic acid. In certain embodiments, the compound is a solvate of 2-(5-(3-fluorophenyl)-3-hydroxypicolinamido)acetic acid. In certain embodiments, the compound is a hydrate of 2-(5-(3-fluorophenyl)-3-hydroxypicolinamido)acetic acid.

In certain such embodiments, the daily dose comprises about 150 mg, about 300 mg, about 450 mg, or about 600 mg of the compound, pharmaceutically acceptable salt, solvate, or hydrate thereof. In certain embodiments, the daily dose comprises about 150 mg. In certain embodiments, the daily dose comprises about 300 mg. In certain embodiments, the daily dose comprises about 450 mg. In certain embodiments, the daily dose comprises about 600 mg.

In certain embodiments, the chronic kidney disease is stage 3, 4, or 5 chronic kidney disease. In certain such embodiments, the chronic kidney disease is pre-dialysis chronic kidney disease. In certain embodiments, the patient has not been previously treated for anemia, such as anemia secondary to chronic kidney disease. In certain alternative embodiments, the patient has been previously treated for anemia, such as anemia secondary to chronic kidney disease. In certain embodiments, the patient is refractory to treatment with recombinant erythropoietin.

In certain embodiments, the daily dose is administered continuously. In certain embodiments, the daily dose is administered indefinitely, such as for more than 42 consecutive days, or even more than 90 consecutive days. In certain alternative embodiments, the daily dose is administered for at least one week and up to 30 consecutive days, up to 35 consecutive days, or even up to 40 consecutive days. In certain embodiments, the daily dose is administered orally, once daily. In certain embodiments, the daily dose is administered orally as a divided dose administered twice daily. In certain embodiments, the daily dose is administered at a specific time of day. In even more specific embodiments, the daily dose is administered in the early afternoon. In a specific embodiment, the patient has chronic kidney disease and the compound (see Section 5.2) is administered at the same time of day, specifically in the late morning, early afternoon, more specifically just before lunch, just after lunch, between lunch and 2 pm, between 10 am and 2 pm, at 10 am, 11 am, at 12 pm, at 1 pm, or at 2 pm.

In certain embodiments, the hemoglobin levels of the patient are maintained at a level of 8.0 g/dL and at or below about 13.0 g/dL, at least about 8.5 g/dL and at or below 13.0 g/dL, at least about 9.0 g/dL and at or below 13.0 g/dL, at least about 9.5 g/dL and at or below 13.0 g/dL, or at least about 10.0 g/dL and at or below about 13.0 g/dL. In certain such embodiments, hemoglobin levels are maintained at a level of at least about 11.0 g/dL and at or below about 13.0 g/dL. In certain such embodiments, hemoglobin levels are maintained at a level of at least about 11.0 g/dL and at or below about 12.0 g/dL. In certain embodiments, these values are adjusted for altitude, gender, and age of the patient.

In certain embodiments, administration of a compound provided herein (see Section 5.2) results in an increase of the level of hemoglobin increases by at least about 0.1 g/dL, by at least about 0.2 g/dL, by at least about 0.3 g/dL, by at least about 0.4 g/dL, by at least about 0.5 g/dL, by at least about 0.6 g/dL, by at least about 0.7 g/dL, by at least about 0.8 g/dL, by at least about 0.9 g/dL, by at least about 1.0 g/dL, by at least about 1.1 g/dL, by at least about 1.2 g/dL, by at least about 1.3 g/dL, by at least about 1.4 g/dL, or by at least about 1.5 g/dL relative to a baseline hemoglobin level.

In certain embodiments, the compound is optionally administered in combination with another medicament. In certain such embodiments, the other medicament is an iron supplement, such as ferrous sulfate, ferrous gluconate, or ferrous fumarate, which may be administered at least two hours following administration of the compound. In certain embodiments, the iron supplement is administered in an amount such that ferritin is maintained at a level of between about 50 ng/mL and about 300 ng/mL. In certain embodiments, the iron supplement is administered orally at a daily dose about 50 mg of elemental iron. In certain embodiments, the iron supplement is administered on an as needed basis, whereas in certain alternative embodiments, the iron supplement is administered continuously and/or indefinitely.

In certain embodiments, the other medicament is an erythropoiesis stimulating agent (ESA), such as an erythropoietin mimetic. In certain embodiments, the other medicament is an rhEPO product, such as epoetin alfa, epoetin beta, darbepoetin, or peginesatide. In certain embodiments, the ESA is administered as a rescue therapy, whereas in certain alternative embodiments, the ESA is administered continuously and/or indefinitely.

In certain such embodiments, the daily dose of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof is adjusted during the course of treatment. Specifically, the treatment is monitored using routine tests such as for example blood pressure, hematocrit, hemoglobin levels, and/or red blood cell count. Depending on the result of these tests, the daily dose is adjusted, i.e., increased or decreased. In more specific embodiments, the treatment is started using a daily dose of about 50 mg, 60 mg, 70 mg, 80 mg, 90 mg, 100 mg, 110 mg, 120 mg, 130 mg, 140 mg, 150 mg, 160 mg, 170 mg, 180 mg, 190 mg, 200 mg, 210 mg, 220 mg, 230 mg, 240 mg, 250 mg, 260 mg, 270 mg, 280 mg, 290 mg, 300 mg, 310 mg, 320 mg, 330 mg, 340 mg, 350 mg, 360 mg, 370 mg, 380 mg, 390 mg, 400 mg, 410 mg, 420 mg, 430 mg, 440 mg, or at a daily dose of about 450 mg of the compound, pharmaceutically acceptable salt, solvate, or hydrate thereof. In certain embodiments, the daily dose is increased subsequently by about 50 mg, 100 mg, 150 mg, or 200 mg. In certain embodiments, the daily dose is decreased subsequently by about 50 mg, 100 mg, 150 mg, or 200 mg. In certain embodiments, the compound is Compound 1 or a pharmaceutically acceptable salt, solvate, or hydrate thereof. In certain embodiments, the compound is Compound 7 or a pharmaceutically acceptable salt, solvate, or hydrate thereof.

In certain embodiments, provided herein are methods of treating anemia, such as anemia secondary to chronic kidney disease, comprising administering to a patient having anemia a daily dose of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof; measuring the hemoglobin level in the patient after an administration of the daily dose of the compound and then again a period of time later, wherein when the hemoglobin level in the patient is less than about 10.0 g/dL and the level of hemoglobin has decreased by less than about 0.5 g/dL as compared to the level measured the period of time earlier; or when the hemoglobin level in the patient is less than about 10.0 g/dL and the level of hemoglobin has changed by up to about 0.4 g/dL as compared to the level measured the period of time earlier, or when the hemoglobin level in the patient is between about 10.0 and about 10.9 g/dL and the level of hemoglobin has decreased by less than about 0.5 g/dL as compared to the level measured the period of time earlier; administering an adjusted daily dose of the compound that is 150 mg greater than the daily dose. In certain embodiments, the period of time is from about one week to about eight weeks, such as from about two weeks to about seven weeks, about three weeks to about six weeks, or about four weeks. In a specific embodiment, the compound is Compound 1 or a pharmaceutically acceptable salt, solvate, or hydrate thereof. In a specific embodiment, the compound is Compound 7 or a pharmaceutically acceptable salt, solvate, or hydrate thereof.

In certain embodiments, provided herein are methods of treating anemia, such as anemia secondary to chronic kidney disease, comprising administering to a patient having anemia a daily dose of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof; measuring the hemoglobin level in the patient after an administration of the daily dose of the compound and then again a period of time later, wherein when the hemoglobin level in the patient is less than about 10.0 g/dL and the level of hemoglobin has increased by greater than about 1.5 g/dL as compared to the level measured the period of time earlier; or when the hemoglobin level in the patient is between about 10.0 and about 10.9 g/dL and the level of hemoglobin has increased by greater than about 1.5 g/dL as compared to the level measured the period of time earlier, or when the hemoglobin level is between about 11.0 and about 12.2 g/dL and the level of hemoglobin has increased by between about 1.0 and about 1.4 g/dL as compared to the level measured the period of time earlier; or when the hemoglobin level is between about 12.3 and about 12.9 g/dL and the level of hemoglobin has decreased by up to about 0.4 g/dL or increased by up to about 0.4 g/dL as compared to the level measured the period of time earlier; or when the hemoglobin level in the patient is between about 12.3 and about 12.9 g/dL and the level of hemoglobin has increased by about 0.5 to about 0.9 g/dL as compared to the level measured the period of time earlier; administering an adjusted daily dose of the compound that is 150 mg less than the daily dose. In certain embodiments, the daily dose of the compound is about 450 mg. In certain embodiments, the compound is {[5-(3-chlorophenyl)-3-hydroxypyridine-2-carbonyl]amino}acetic acid. In certain embodiments, the compound is a pharmaceutically acceptable salt of {[5-(3-chlorophenyl)-3-hydroxypyridine-2-carbonyl]amino}acetic acid. In certain embodiments, the compound is a solvate of {[5-(3-chlorophenyl)-3-hydroxypyridine-2-carbonyl]amino}acetic acid. In certain embodiments, the compound is a hydrate of {[5-(3-chlorophenyl)-3-hydroxypyridine-2-carbonyl]amino}acetic acid. In certain embodiments, the compound is 2-(5-(3-fluorophenyl)-3-hydroxypicolinamido)acetic acid. In certain embodiments, the compound is a pharmaceutically acceptable salt of 2-(5-(3-fluorophenyl)-3-hydroxypicolinamido)acetic acid. In certain embodiments, the compound is a solvate of 2-(5-(3-fluorophenyl)-3-hydroxypicolinamido)acetic acid. In certain embodiments, the compound is a hydrate of 2-(5-(3-fluorophenyl)-3-hydroxypicolinamido)acetic acid. In certain embodiments, the period of time is from about one week to about eight weeks, such as from about two weeks to about seven weeks, about three weeks to about six weeks, or about four weeks.

In certain embodiments, provided herein are a method of treating anemia, such as anemia secondary to chronic kidney disease, comprising administering to a patient having anemia a daily dose of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof; measuring the hemoglobin level in the patient after an administration of the daily dose of the compound and then again a period of time later, wherein when the hemoglobin level in the patient is between about 11.0 and about 12.2 g/dL and the level of hemoglobin has increased by greater than about 1.5 g dL as compared to the level measured the period of time earlier; or when the hemoglobin level in the patient is between about 12.3 and about 12.9 g/dL and the level of hemoglobin has increased by between about 1.0 and about 1.4 g/dL as compared to the level measured the period of time earlier; or when the hemoglobin level in the patient is between about 12.3 and about 12.9 g/dL and the level of hemoglobin has increased by greater than about 1.5 g/dL as compared to the level measured the period of time earlier; or administering an adjusted daily dose of the compound that is 300 mg less than the daily dose. In certain embodiments, the daily dose of the compound is about 450 mg. In certain embodiments, the compound is {[5-(3-chlorophenyl)-3-hydroxypyridine-2-carbonyl]amino}acetic acid. In certain embodiments, the compound is a pharmaceutically acceptable salt of {[5-(3-chlorophenyl)-3-hydroxypyridine-2-carbonyl]amino}acetic acid. In certain embodiments, the compound is a solvate of {[5-(3-chlorophenyl)-3-hydroxypyridine-2-carbonyl]amino}acetic acid. In certain embodiments, the compound is a hydrate of {[5-(3-chlorophenyl)-3-hydroxypyridine-2-carbonyl]amino}acetic acid. In certain embodiments, the daily dose of the compound is about 450 mg. In certain embodiments, the compound is 2-(5-(3-fluorophenyl)-3-hydroxypicolinamido)acetic acid. In certain embodiments, the compound is a pharmaceutically acceptable salt of 2-(5-(3-fluorophenyl)-3-hydroxypicolinamido)acetic acid. In certain embodiments, the compound is a solvate of 2-(5-(3-fluorophenyl)-3-hydroxypicolinamido)acetic acid. In certain embodiments, the compound is a hydrate of 2-(5-(3-fluorophenyl)-3-hydroxypicolinamido)acetic acid. In certain embodiments, the period of time is from about one week to about eight weeks, such as from about two weeks to about seven weeks, about three weeks to about six weeks, or about four weeks.

In certain embodiments, the invention relates to a method for treating anemia, such as anemia secondary to chronic kidney disease, comprising administering to a patient having anemia a daily dose of a compound which is {[5-(3-chlorophenyl)-3-hydroxypyridine-2-carbonyl]amino}acetic acid or a pharmaceutically acceptable salt, solvate, or hydrate thereof, wherein the daily dose is about 450 mg.

In certain such embodiments, the daily dose is increased by about 150 mg such that the daily dose of the compound is about 600 mg. In certain embodiments, the daily dose is decreased by about 150 mg, such that the daily dose of the compound is about 300 mg. In certain embodiments, the daily dose is decreased by about 300 mg, such that the daily dose of the compound is about 150 mg.

In certain embodiments, the compound is {[5-(3-chlorophenyl)-3-hydroxypyridine-2-carbonyl]amino}acetic acid. In certain embodiments, the compound is a pharmaceutically acceptable salt of {[5-(3-chlorophenyl)-3-hydroxypyridine-2-carbonyl]amino}acetic acid. In certain embodiments, the compound is a solvate of {[5-(3-chlorophenyl)-3-hydroxypyridine-2-carbonyl]amino}acetic acid. In certain embodiments, the compound is a hydrate of {[5-(3-chlorophenyl)-3-hydroxypyridine-2-carbonyl]amino}acetic acid.

In certain embodiments, the chronic kidney disease is stage 3, 4, or 5 chronic kidney disease. In certain such embodiments, the chronic kidney disease is pre-dialysis chronic kidney disease. In certain embodiments, the patient has not been previously treated for anemia, such as anemia secondary to chronic kidney disease. In certain alternative embodiments, the patient has been previously treated for anemia, such as anemia secondary to chronic kidney disease.

In certain embodiments, the invention relates to a method of treating anemia, such as anemia secondary to chronic kidney disease, comprising administering to a patient having anemia a daily dose of a compound which is {[5-(3-chlorophenyl)-3-hydroxypyridine-2-carbonyl]amino}acetic acid or a pharmaceutically acceptable salt, solvate, or hydrate thereof; measuring the hemoglobin level in the patient after an administration of the daily dose of the compound and then again a period of time later, wherein when the hemoglobin level in the patient is between about 11.0 and about 12.2 g/dL and the level of hemoglobin has increased by greater than about 1.5 g/dL as compared to the level measured the period of time earlier; or when the hemoglobin level in the patient is between about 12.3 and about 12.9 g/dL and the level of hemoglobin has increased by between about 1.0 and about 1.4 g/dL as compared to the level measured the period of time earlier; or when the hemoglobin level in the patient is between about 12.3 and about 12.9 g/dL and the level of hemoglobin has increased by greater than about 1.5 g/dL as compared to the level measured the period of time earlier; or administering an adjusted daily dose of the compound that is 300 mg less than the daily dose In certain embodiments, the daily dose of the compound is about 450 mg.

5.3.1 Diurnal Variation Of Serum Erythropoietin

Phase I clinical trials in healthy adult males showed that Compound 1, a HIF prolyl hydroxylase inhibitor, was able to increase serum hemoglobin levels while serum EPO levels returned to approximately baseline levels within twenty-four hours after administration. Unexpectedly, it was subsequently discovered that, in patients having a disease or condition related to diminished endogenous production of erythropoietin (EPO) or a disease or condition related to deficiencies in endogenous hemoglobin production, such as anemia or anemia secondary to chronic kidney disease, through administration of successive doses of a HIF prolyl hydroxylase inhibitor compound of the type disclosed herein, it is possible to increase serum hemoglobin levels in said patients while mimicking the diurnal variation of serum EPO levels in healthy individuals and without significantly raising the patients' baseline serum EPO levels. This was a surprising result for a number of reasons. For example, this result was surprising due to the fact that the half-life of the compound in such unhealthy patients was approximately twice as long as compared to the half-life in healthy adult males. Accordingly, one of skill in the art would have expected that a return to baseline EPO levels would take significantly longer in the kidney impaired patients, potentially leading to prolonged, supraphysiologic EPO levels and unwanted side-effects typically associated with administration of exogenous EPO. In addition, this result was surprising because the kidney is the primary source of erythropoietin production in humans. Thus, particularly with regard to patients having a disease or condition associated with kidney impairment, a person of skill in the art would not expect that administration of a compound provided herein could cause an increase in a patient's serum hemoglobin levels while also mimicking the diurnal variation of serum EPO levels in healthy individuals and without raising the patients' baseline serum EPO levels. Such a surprising result allows the administration to patients having a disease or condition related to diminished endogenous production of erythropoietin (EPO) or a disease or condition related to endogenous hemoglobin production, such as anemia or anemia secondary to chronic kidney disease, of a sufficient number of successive doses of a compound as disclosed herein, such as Compound 1, so as to raise the level of hemoglobin relative to a baseline hemoglobin level in a patient, while simultaneously mimicking the diurnal variation of serum EPO) levels in healthy individuals, and without significantly increasing the baseline level of serum erythropoietin (EPO).

In certain embodiments, provided herein are methods for treating and/or preventing anemia in a subject, the method comprises administering to the subject a pharmaceutically effective amount of a HIF prolyl hydroxylase inhibitor or a HIF-alpha stabilizer, wherein the pharmaceutically effective amount is suitable to mimic the diurnal variation of scrum erythropoietin. More specifically, administration of a pharmaceutically effective amount of a compound provided herein increases the trough levels of EPO mRNA and/or EPO protein by about 0%, by at most 5%, 10%, 15%, 20%, 25%, 30%, 35%, 40%, 45%, or by at most 50% relative to the trough levels of EPO mRNA and/or EPO protein prior to the treatment and/or relative to trough levels of EPO mRNA and/or EPO protein in a subject without anemia, while at the same time increasing the peak levels of serum EPO during the circadian cycle by at least 10%, 15%, 20%, 25%, 30%, 35%, 40%, 45%, 50%, 55%, 60%, 65%, 70%, 75%, 80%, 85%, 90%, 95%, 100%, 110%, 120%, 130%, 140%, or at least 150% relative to the peak levels of serum EPO prior to treatment (or compared to a healthy, non-anemic subject). In certain embodiments, the HIF prolyl hydroxylase inhibitor or the HIF-alpha stabilizer is a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof More specifically, the pharmaceutically effective amount is suitable to mimic the diurnal variation of serum erythropoietin without increasing serum erythropoietin above baseline levels, wherein the baseline levels is the diurnal baseline of EPO in a healthy volunteer without anemia.

In certain embodiments, the pharmaceutically effective amount is suitable to increase EPO levels as measured by area under the curve by plotting EPO protein levels over a 24 hour time period. The 12 hour period during which EPO protein levels are at their diurnal lowest level (trough) is the "trough period;" the 12 hour period during which EPO protein levels are at their diurnal highest level (peak) is the "peak period." In certain embodiments, at least 50%, 55%, 60%, 65%, 70%, 75%, 80%, 85%, 90%, or at least 95%, or 100% of the increase in EPO levels occur during the peak period.

In certain embodiments, provided herein are methods for treating a disease or condition related to diminished endogenous production of erythropoietin (EPO), comprising administering to a patient having a disease or condition related to diminished endogenous production of EPO a sufficient number of successive doses of a HIF prolyl hydroxylase inhibitor or a HIF-alpha stabilizer, so as to raise the level of hemoglobin relative to a baseline hemoglobin level in a patient, while mimicking the diurnal variation of serum EPO levels in healthy individuals. In certain embodiments, the HIF prolyl hydroxylase inhibitor or HIF-alpha stabilizer is a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11 Compound 12, Compound 13, Metabolite 1, or Metabolite 2 or a pharmaceutically acceptable salt, solvate, or hydrate thereof. In a specific embodiment, the HIF prolyl hydroxylase inhibitor or HIF-alpha stabilizer is Compound 1 or a pharmaceutically acceptable salt, solvate, or hydrate thereof. In a specific embodiment, the HIF prolyl hydroxylase inhibitor or HIF-alpha stabilizer is Compound 7 or a pharmaceutically acceptable salt, solvate, or hydrate thereof. In certain such embodiments, the cardiovascular side-effects and risk of thromboembolic events associated with administration of exogenous EPO are minimized.

More specifically, administration of a compound provided herein to a subject with a disease or condition related to diminished endogenous production of erythropoietin (EPO) is performed at a dose that increases the trough levels of EPO mRNA and/or EPO protein by about 0%, by at most 5%, 10%, 15%, 20%, 25%, 30%, 35%, 40%, 45%, or by at most 50% relative to the trough levels of EPO mRNA and/or EPO protein levels prior to the treatment and/or relative to trough levels of EPO mRNA and/or EPO protein in a subject without anemia, while at the same time increasing the peak levels of EPO mRNA and/or EPO protein during the circadian cycle be at least 10%, 15%, 20%, 25%, 30%, 35%, 40%, 45%, 50%, 55%, 60%, 65%, 70%, 75%, 80%, 85%, 90%, 95%, or at least 100% relative to the peak levels of EPO mRNA and/or EPO protein prior to the treatment and/or relative to trough levels of EPO mRNA and/or EPO protein in a subject without anemia.

More specifically, the pharmaceutically effective amount is suitable to mimic in a subject with a disease or condition related to diminished endogenous production of erythropoietin (EPO) the diurnal variation of serum erythropoietin without increasing scrum erythropoietin above baseline levels, wherein the baseline levels is the diurnal baseline of EPO in a healthy volunteer without anemia. In certain such embodiments, the diurnal cycle is mimicked but the amplitude of the daily variation of serum EPO levels is increased. For example, EPO levels are increased by at least 50%, 55%, 60%, 65%, 70%, 75%, 80%, 85%, 90%, or at least 95%, or 100% during the peak period but the trough levels are not significantly increased.

In certain such embodiments, the level of serum EPO returns to about baseline level within about one week, about six days, about five days, about four days, about three days, about two days, about twenty four hours, about eighteen hours, or about twelve hours of administering a dose of the HIF prolyl hydroxylase inhibitor or HIF-alpha stabilizer.

In certain embodiments, the level of serum EPO returns to within about 5 mIU/mL, about 4 mIU/mL, about 3 mIU/mL, about 2 mIU/mL, or about 1 mIU/mL of the baseline level of EPO.

In certain embodiments, the level of hemoglobin is raised by between about 0.1 and about 1.0 g/dL over a period of one week relative to the baseline hemoglobin level. In certain such embodiments, the level of hemoglobin is raised by about 0.1 g/dL over a period of one week relative to the baseline hemoglobin level.

In certain embodiments, the level of hemoglobin is raised by between about 0.1 and about 1.0 g/dL over a period of two weeks relative to the baseline hemoglobin level. In certain such embodiments, the level of hemoglobin is raised by about 0.1 g/dL over a period of two weeks relative to the baseline hemoglobin level.

In certain embodiments, the level of hemoglobin is raised by between about 0.1 and about 1.0 g/dL over a period of three weeks relative to the baseline hemoglobin level. In certain such embodiments, the level of hemoglobin is raised by about 0.5 g/dL over a period of three weeks relative to the baseline hemoglobin level.

In certain embodiments, the level of hemoglobin is raised by between about 0.1 and about 1.0 g/dL over a period of four weeks relative to the baseline hemoglobin level. In certain such embodiments, the level of hemoglobin is raised by about 0.6 g/dL over a period of four weeks relative to the baseline hemoglobin level.

In certain embodiments, the disease or condition is anemia. In certain such embodiments, the anemia is anemia secondary to chronic kidney disease (CKD). In certain such embodiments, the chronic kidney disease is stage 3, 4, or 5 chronic kidney disease. In certain such embodiments, the chronic kidney disease is pre-dialysis chronic kidney disease.

In certain embodiments, the HIF prolyl hydroxylase inhibitor or HIF-alpha stabilizer is administered once daily. In certain embodiments, the HIF prolyl hydroxylase inhibitor or HIF-alpha stabilizer is administered orally.

In certain embodiments, provided herein are methods for treating a disease or condition related to diminished endogenous production of erythropoietin (EPO), comprising administering to a patient having a disease or condition related to diminished endogenous production of EPO a sufficient number of successive doses of a HIF prolyl hydroxylase inhibitor or a HIF-alpha stabilizer so as to raise the level of hemoglobin relative to a baseline hemoglobin level in a patient, wherein the time period between the administration of at least one of said successive doses and the administration of the immediately preceding dose is a sufficient time period to permit the level of serum EPO in a patient to return to about baseline serum EPO level. In certain, more specific embodiments, the HIF prolyl hydroxylase inhibitor or the HIF-alpha stabilizer is a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof. In even more specific embodiments, the HIF prolyl hydroxylase inhibitor or a HIF-alpha stabilizer is Compound 1 or a pharmaceutically acceptable salt, solvate, or hydrate thereof. In even more specific embodiments, the HIF prolyl hydroxylase inhibitor or a HIF-alpha stabilizer is Compound 7 or a pharmaceutically acceptable salt, solvate, or hydrate thereof. In certain such embodiments, the cardiovascular side-effects and risk of thromboembolic events associated with administration of exogenous EPO are minimized.

In certain such embodiments, the level of serum EPO returns to about baseline level within about one week, about six days, about five days, about four days, about three days, about two days, about twenty four hours, about eighteen hours, or about twelve hours of administering a dose of the HIF prolyl hydroxylase inhibitor or HIF-alpha stabilizer.

In certain embodiments, the level of serum EPO returns to within about 5 mIU/mL, about 4 mIU/mL, about 3 mIU/mL, about 2 mIU/mL, or about 1 mIU/mL of the baseline level of EPO.

In certain embodiments, the level of hemoglobin is raised by between about 0.1 and about 1.0 g/dL over a period of one week relative to the baseline hemoglobin level. In certain such embodiments, the level of hemoglobin is raised by about 0.1 g/dL over a period of one week relative to the baseline hemoglobin level.

In certain embodiments, the level of hemoglobin is raised by between about 0.1 and about 1.0 g/dL over a period of two weeks relative to the baseline hemoglobin level. In certain such embodiments, the level of hemoglobin is raised by about 0.1 g/dL over a period of two weeks relative to the baseline hemoglobin level.

In certain embodiments, the level of hemoglobin is raised by between about 0.1 and about 1.0 g/dL over a period of three weeks relative to the baseline hemoglobin level. In certain such embodiments, the level of hemoglobin is raised by about 0.5 g/dL over a period of three weeks relative to the baseline hemoglobin level.

In certain embodiments, the level of hemoglobin is raised by between about 0.1 and about 1.0 g/dL over a period of four weeks relative to the baseline hemoglobin level. In certain such embodiments, the level of hemoglobin is raised by about 0.6 g/dL over a period of four weeks relative to the baseline hemoglobin level.

In certain embodiments, the disease or condition is anemia. In certain such embodiments, the anemia is anemia secondary to chronic kidney disease (CKD). In certain such embodiments, the chronic kidney disease is stage 3, 4, or 5 chronic kidney disease. In certain such embodiments, the chronic kidney disease is pre-dialysis chronic kidney disease.

In certain embodiments, the HIF prolyl hydroxylase inhibitor or HIF-alpha stabilizer is administered once daily. In certain embodiments, the HIF prolyl hydroxylase inhibitor or HIF-alpha stabilizer is administered orally.

In certain embodiments, provided herein are methods for treating a disease or condition related to diminished endogenous production of erythropoietin (EPO), comprising administering to a patient having a disease or condition related to diminished endogenous production of EPO a sufficient number of successive doses of a HIF prolyl hydroxylase inhibitor or a HIF-alpha stabilizer so as to raise the level of hemoglobin relative to a baseline hemoglobin level in a patient, wherein prior to the addition of one or more doses following the initial dose the level of serum EPO returns to about a baseline level. In certain more specific embodiments, the HIF prolyl hydroxylase inhibitor or the HIF-alpha stabilizer is a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof. In certain specific embodiments, the compound is Compound 1. In certain specific embodiments, the compound is Compound 7. In certain such embodiments, the cardiovascular side-effects and risk of thromboembolic events associated with administration of exogenous EPO are minimized.

In certain such embodiments, the level of serum EPO returns to about baseline level within about one week, about six days, about five days, about four days, about three days, about two days, about twenty four hours, about eighteen hours, or about twelve hours of administering a dose of the HIF prolyl hydroxylase inhibitor or HIF-alpha stabilizer.

In certain embodiments, the level of serum EPO returns to within about 5 mIU/mL, about 4 mIU/mL, about 3 mIU/mL, about 2 mIU/mL, or about 1 mIU/mL of the baseline level of EPO.

In certain embodiments, the level of hemoglobin is raised by between about 0.1 and about 1.0 g/dL over a period of one week relative to the baseline hemoglobin level. In certain such embodiments, the level of hemoglobin is raised by about 0.1 g/dL over a period of one week relative to the baseline hemoglobin level.

In certain embodiments, the level of hemoglobin is raised by between about 0.1 and about 1.0 g/dL over a period of two weeks relative to the baseline hemoglobin level. In certain such embodiments, the level of hemoglobin is raised by about 0.1 g/dL over a period of two weeks relative to the baseline hemoglobin level.

In certain embodiments, the level of hemoglobin is raised by between about 0.1 and about 1.0 g/dL over a period of three weeks relative to the baseline hemoglobin level. In certain such embodiments, the level of hemoglobin is raised by about 0.5 g/dL over a period of three weeks relative to the baseline hemoglobin level.

In certain embodiments, the level of hemoglobin is raised by between about 0.1 and about 1.0 g/dL over a period of four weeks relative to the baseline hemoglobin level. In certain such embodiments, the level of hemoglobin is raised by about 0.6 g/dL over a period of four weeks relative to the baseline hemoglobin level.

In certain embodiments, the disease or condition is anemia. In certain such embodiments, the anemia is anemia secondary to chronic kidney disease (CKD). In certain such embodiments, the chronic kidney disease is stage 3, 4, or 5 chronic kidney disease. In certain such embodiments, the chronic kidney disease is pre-dialysis chronic kidney disease.

In certain embodiments, the HIF prolyl hydroxylase inhibitor or HIF-alpha stabilizer is administered once daily. In certain embodiments, the HIF prolyl hydroxylase inhibitor or HIF-alpha stabilizer is administered orally.

In certain embodiments, provided herein are methods for treating a disease or condition related to diminished endogenous production of erythropoietin (EPO), comprising administering to a patient having a disease or condition related to diminished endogenous production of EPO a sufficient number of successive doses of a HIF prolyl hydroxylase inhibitor or a HIF-alpha stabilizer so as to raise the level of hemoglobin relative to a baseline hemoglobin level in a patient without significantly increasing the level of serum EPO relative to the baseline level of serum EPO, wherein the HIF prolyl hydroxylase inhibitor or a HIF-alpha stabilizer is a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof. In a specific embodiment, the compound is Compound 1 or a pharmaceutically acceptable salt, solvate, or hydrate thereof. In a specific embodiment, the compound is Compound 7 or a pharmaceutically acceptable salt, solvate, or hydrate thereof. In certain such embodiments, the cardiovascular side-effects and risk of thromboembolic events associated with administration of exogenous EPO are minimized.

In certain such embodiments, the level of serum EPO returns to about baseline level within about one week, about six days, about five days, about four days, about three days, about two days, about twenty four hours, about eighteen hours, or about twelve hours of administering a dose of the HIF prolyl hydroxylase inhibitor or HIF-alpha stabilizer.

In certain embodiments, the level of serum EPO returns to within about 5 mIU/mL, about 4 mIU/mL, about 3 mIU/mL, about 2 mIU/mL, or about 1 mIU/mL of the baseline level of EPO.

In certain embodiments, the level of hemoglobin is raised by between about 0.1 and about 1.0 g/dL over a period of one week relative to the baseline hemoglobin level. In certain such embodiments, the level of hemoglobin is raised by about 0.1 g/dL over a period of one week relative to the baseline hemoglobin level.

In certain embodiments, the level of hemoglobin is raised by between about 0.1 and about 1.0 g/dL over a period of two weeks relative to the baseline hemoglobin level. In certain such embodiments, the level of hemoglobin is raised by about 0.1 g/dL over a period of two weeks relative to the baseline hemoglobin level.

In certain embodiments, the level of hemoglobin is raised by between about 0.1 and about 1.0 g/dL over a period of three weeks relative to the baseline hemoglobin level. In certain such embodiments, the level of hemoglobin is raised by about 0.5 g/dL over a period of three weeks relative to the baseline hemoglobin level.

In certain embodiments, the level of hemoglobin is raised by between about 0.1 and about 1.0 g/dL over a period of four weeks relative to the baseline hemoglobin level. In certain such embodiments, the level of hemoglobin is raised by about 0.6 g/dL over a period of four weeks relative to the baseline hemoglobin level.

In certain embodiments, the disease or condition is anemia. In certain such embodiments, the anemia is anemia secondary to chronic kidney disease (CKD). In certain such embodiments, the chronic kidney disease is stage 3, 4, or 5 chronic kidney disease. In certain such embodiments, the chronic kidney disease is pre-dialysis chronic kidney disease.

In certain embodiments, the HIF prolyl hydroxylase inhibitor or HIF-alpha stabilizer is administered once daily. In certain embodiments, the HIF prolyl hydroxylase inhibitor or HIF-alpha stabilizer is administered orally.

In normal, healthy adults, there is a normal diurnal variation in the serum levels of erythropoietin (EPO) where there is a rise in the levels of serum followed by a return to baseline serum EPO levels. That is, EPO is detectable in the serum and shows fluctuations during the 24-hr period, with a well-marked rhythm with maximum levels in the afternoon, thereafter returning to a baseline level which varies between individuals.

Serum EPO levels may be determined, for example using in vivo bioassays, in vitro bioassays and immunological assays. In certain embodiments, the serum EPO levels described herein are determined using an immunological assay, such as an ELISA assay.

Serum hemoglobin levels may be determined, for example using standard approach CBC where red blood cells are lysed and potassium ferricyanide oxidizes hemoglobin to methemoglobin, which combines with potassium cyanide forming cyanmethemoglobin. The brown color is measured spectrophotometrically and the corresponding hemoglobin reported.

In certain embodiments, the provided herein is a method of treating a disease or condition related to diminished endogenous production of erythropoietin (EPO) or a disease or condition related to diminished production of hemoglobin, comprising administering to a patient having a disease or condition related to diminished endogenous production of EPO a sufficient number of successive doses of a HIF prolyl hydroxylase inhibitor or a HIF-alpha stabilizer so as to raise the level of hemoglobin relative to a baseline hemoglobin level in a patient, while mimicking the diurnal variation of serum EPO levels in healthy individuals. In certain such embodiments, provided herein is a method of treating a disease or condition related to diminished endogenous production of erythropoietin (EPO) or a disease or condition related to diminished production of hemoglobin while minimizing the cardiovascular side-effects and risk of thromboembolic events associated with administration of exogenous EPO. In a specific embodiment, the compound is Compound 1 or a pharmaceutically acceptable salt, solvate, or hydrate thereof. In a specific embodiment, the compound is Compound 7 or a pharmaceutically acceptable salt, solvate, or hydrate thereof.

In certain embodiments, provided herein are methods of treating a disease or condition related to diminished endogenous production of erythropoietin (EPO) or a disease or condition related to diminished production of hemoglobin, comprising administering to a patient having a disease or condition related to diminished endogenous production of EPO a sufficient number of successive doses of a HIF prolyl hydroxylase inhibitor or a HIF-alpha stabilizer so as to raise the level of hemoglobin relative to a baseline hemoglobin level in a patient, wherein the time period between the administration of at least one of said successive doses and the administration of the immediately preceding dose is a sufficient time period to permit the level of serum EPO in a patient to return to about baseline serum EPO level. In certain such embodiments, provided herein are methods of treating a disease or condition related to diminished endogenous production of erythropoietin (EPO) or a disease or condition related to diminished production of hemoglobin while minimizing the cardiovascular side-effects and risk of thromboembolic events associated with administration of exogenous EPO. In a specific embodiment, the compound is Compound 1 or a pharmaceutically acceptable salt, solvate, or hydrate thereof. In a specific embodiment, the compound is Compound 7 or a pharmaceutically acceptable salt, solvate, or hydrate thereof.

In certain embodiments, provided herein are methods of treating a disease or condition related to diminished endogenous production of erythropoietin (EPO) or a disease or condition related to diminished production of hemoglobin, comprising administering to a patient having a disease or condition related to diminished endogenous production of EPO a sufficient number of successive doses of a HIF prolyl hydroxylase inhibitor or a HIF-alpha stabilizer so as to raise the level of hemoglobin relative to a baseline hemoglobin level in a patient, wherein prior to the addition of one or more doses following the initial dose the level of serum EPO returns to about a baseline level. In certain such embodiments, provided herein are methods of treating a disease or condition related to diminished endogenous production of erythropoietin (EPO) or a disease or condition related to diminished production of hemoglobin while minimizing the cardiovascular side-effects and risk of thromboembolic events associated with administration of exogenous EPO. In a specific embodiment, the compound is Compound 1 or a pharmaceutically acceptable salt, solvate, or hydrate thereof. In a specific embodiment, the compound is Compound 7 or a pharmaceutically acceptable salt, solvate, or hydrate thereof.

In certain embodiments, provided herein are methods of treating a disease or condition related to diminished endogenous production of erythropoietin (EPO) or a disease or condition related to diminished production of hemoglobin, comprising administering to a patient having a disease or condition related to diminished endogenous production of EPO a sufficient number of successive doses of a HIF prolyl hydroxylase inhibitor or a HIF-alpha stabilizer so as to raise the level of hemoglobin relative to a baseline hemoglobin level in a patient without significantly increasing the level of serum EPO relative to the baseline level of serum EPO. In certain such embodiments, provided herein are methods of treating a disease or condition related to diminished endogenous production of erythropoietin (EPO) or a disease or condition related to diminished production of hemoglobin while minimizing the cardiovascular side-effects and risk of thromboembolic events associated with administration of exogenous EPO. In a specific embodiment, the compound is Compound 1 or a pharmaceutically acceptable salt, solvate, or hydrate thereof. In a specific embodiment, the compound is Compound 7 or a pharmaceutically acceptable salt, solvate, or hydrate thereof.

In certain such embodiments, provided herein are methods of treating a disease or condition related to diminished endogenous production of erythropoietin (EPO) or a disease or condition related to diminished production of hemoglobin while minimizing the cardiovascular side-effects and risk of thromboembolic events associated with administration of exogenous EPO.

In certain embodiments, the level of serum EPO returns to about baseline level within one week, within six days, within five days, within four days within three days, within two days, within twenty four hours, within eighteen hours, or within twelve hours of administering a dose of the HIF prolyl hydroxylase inhibitor or HIF-alpha stabilizer.

In certain embodiments, the level of serum EPO returns to within about 5 mlU/mL, about 4 mlU/mL, about 3 mlU/mL, about 2 mlU/mL, or about 1 mlU/mL of the baseline level of EPO.

In certain embodiments, the level of hemoglobin is raised by between about 0.1 and 1.0 g/dL, between about 0.1 and about 0.9 g/dL, about 0.1 and about 0.8 g/dL, about 0.1 and about 0.7 g/dL, about 0.1 and about 0.6 g/dL, or about 0.1 and about 0.5 g/dL over a period of time, such as about one week, about two weeks, about three weeks, or about four weeks, relative to the baseline hemoglobin level. In certain embodiments, the level of hemoglobin is raised by at least about 0.1 g/dL, about 0.2 g/dL, about 0.3 g/dL, about 0.4 g/dL, about 0.5 g/dL, about 0.6 g/dL, about 0.7 g/dL, about 0.8 g/dL, about 0.9, or about 1.0 g/dL over a period of time, such as about one week, about two weeks, about three weeks, or about four weeks, relative to the baseline hemoglobin level.

In certain embodiments, the level of hemoglobin is raised by about 0.1 g/dL over a period of one week relative to the baseline hemoglobin level. In certain embodiments, the level of hemoglobin is raised by about 0.1 g/dL over a period of two weeks relative to the baseline hemoglobin level. In certain embodiments, the level of hemoglobin is raised by about 0.5 g/dL over a period of three weeks relative to the baseline hemoglobin level. In certain embodiments, the level of hemoglobin is raised by about 0.6 g/dL over a period of four weeks relative to the baseline hemoglobin level.

In certain embodiments, provided herein are methods of treating or preventing anemia (e.g., anemia secondary to or associated with chronic kidney disease, anemia secondary to chronic heart disease, idiopathic anemia of aging, anemia of chronic disease, myelodysplastic syndrome, bone marrow fibrosis, other aplastic or dysplastic anemias, chemotherapy induced anemia (including chemotherapy for treating cancer, hepatitis C, or other chronic drug therapy that reduces bone marrow production), anemia resulting from blood loss, anemia resulting from iron deficiency, anemia resulting from vitamin B12 deficiency, sickle cell disease, or thalassemia), comprising administering to a patient having anemia an effective amount of a compound disclosed herein, such as Compound 1, wherein the diurnal pattern of EPO expression is mimicked in the patient in response to said administration as described above. In certain embodiments, provided herein are methods of treating anemia, such as anemia secondary to chronic kidney disease, comprising administering to a patient having anemia an effective amount of a compound disclosed herein, such as Compound 1, wherein the diurnal pattern of EPO expression is mimicked in the patient in response to said administration as described above.

In certain embodiments, provided herein are treating or preventing anemia secondary to chronic kidney disease (CKD), comprising administering to a patient having anemia secondary to CKD an effective amount of a compound disclosed herein, such as Compound 1. Such daily doses may be administered orally, preferably once daily. In certain embodiments, the daily dose is administered once daily. In certain embodiments, the CKD is stage 1, 2, 3, 4, or 5 chronic kidney disease. In certain such embodiments, the CKD is stage 3, 4, or 5 chronic kidney disease. In certain embodiments, the CKD is stage 1 chronic kidney disease. In certain embodiments, the CKD is stage 2 chronic kidney disease. In certain embodiments, the CKD is stage 3 chronic kidney disease. In certain embodiments, the CKD is stage 4 chronic kidney disease. In certain embodiments, the CKD is stage 5 chronic kidney disease. In certain embodiments, the chronic kidney disease is pre-dialysis chronic kidney disease. In certain embodiments, the patient is a dialysis patient and these patients may be referred to as having end stage renal disease (ESRD). In certain such embodiments, the anemia, such as anemia secondary to CKD or ESRD may be refractory to treatment with an erythropoiesis stimulating agent, including a rhEPO product, such as, epoetin alfa, epoetin beta, darbepoetin, or peginesatide. In certain embodiments, the patient has been previously treated for anemia, while in certain alternative embodiments, the patient has not previously been treated for anemia.

In certain embodiments, the patient is a patient having chronic kidney disease. In certain more specific embodiments, the patient does not have endogenous EPO circadian circulation expression patterns. In certain embodiments, the compound (ie, a compound disclosed in Section 5.2) is administered to mimic the normal and endogenous circadian pattern of the EPO (ie., of a healthy person), such that the peak of the EPO expression occurs between 6 p.m. and midnight. In certain embodiments, the compound is administered at a time such that the EPO peak is earlier than the cortisol peak, specifically, such that the EPO peak precedes the cortisol peak by about 1 hour, by about 2 hours, by about 3 hours, by about 4 hours, by about 5 hours, by about 6 hours, by about 7 hours, or by about 8 hours. In certain embodiments, the cortisol peak is in the morning. In certain embodiments, the compound is administered at 8 a.m., 9 a.m., 10 a.m., 11 a.m., 12 p.m., 1 p.m., or 2 p.m. In certain embodiments, compound is administered after breakfast. In certain embodiments, the compound is administered between breakfast and 8 a.m., 9 a.m., 10 a.m., 11 a.m., 12 p.m., 1 p.m., or 2 p.m. In certain embodiments, the compound is administered before lunch. In certain embodiments, the compound is administered between breakfast and lunch. In certain embodiments the compound is administered after lunch. In certain embodiments, the compound is administered between lunch and 2 p.m. In certain embodiments, the compound is administered every day at the or at about the same time. In a specific embodiment, provided herein is a method for treating anemia in a subject with chronic kidney disease, wherein a daily dose of 100 mg, about 110 mg, about 120 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, about 260 mg, about 270 mg, about 280 mg, about 290 mg, about 300 mg, about 310 mg, about 320 mg, about 330 mg, about 340 mg, about 350 mg, about 360 mg, about 370 mg, about 380 mg, about 390 mg, about 400 mg, about 410 mg, about 420 mg, about 430 mg, about 440 mg, about 450 mg, about 600 mg, or about 750 mg is administered between morning and 2 pm at the same time every day.

5.3.2 Total Iron Binding Capacity

Phase 2a clinical trials showed that, in stage 3, 4, or 5 CKD patients. Compound 1, a HIF prolyl hydroxylase inhibitor, was able to increase TIBC levels, at 6 weeks post administration as compared to placebo treated patients. Unexpectedly, the increase in TIBC levels was not associated with an increase in serum iron levels. Further, it was also discovered that Compound 1 resulted in a dose-related increase in TIBC and a decrease in TSAT, suggesting administration of Compound 1 results in enhanced iron mobilization.

In certain embodiments, provided herein is a method of treating or preventing a disease or condition related to diminished endogenous production of erythropoietin (EPO), comprising administering to a patient having a disease or condition related to diminished endogenous production of EPO a pharmaceutically effective amount of a HIF prolyl hydroxylase inhibitor or a HIF-alpha stabilizer as disclosed herein, wherein the pharmaceutically effective amount of a HIF prolyl hydroxylase inhibitor or a HIF-alpha stabilizer is suitable to increase the total iron binding capacity in the patient by at least 5%, 10%, 15%, 20%, 25%, 30%, 35%, 40%, 45%, or at least 50%. In more specific embodiments, the pharmaceutically effective amount is suitable to increase the total iron binding capacity in the patient by at least 5%, 10%, 15%, 20%, 25%, 30%, 35%, 40%, 45%, or at least 50% while the total serum iron levels are not increased, or are increased by at most 1%, 2%, 3%, 4%, 5%, 6%, 7%, 8%, 9%, 10%, 15%, 20%, or at most 25%. In certain embodiments, the HIF prolyl hydroxylase inhibitor or the HIF-alpha stabilizer is a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof. Specifically, the HIF prolyl hydroxylase inhibitor or a HIF-alpha stabilizer is Compound 1 or a pharmaceutically acceptable salt, solvate, or hydrate thereof. Specifically, the HIF prolyl hydroxylase inhibitor or a HIF-alpha stabilizer is Compound 7 or a pharmaceutically acceptable salt, solvate, or hydrate thereof.

In certain embodiments, provided herein is a method of treating a disease or condition that is treatable by increasing endogenous erythropoietin (EPO) production, comprising administering to a patient having a disease or condition that is treatable by increasing endogenous production of EPO a pharmaceutically effective amount of a HIF prolyl hydroxylase inhibitor or a HIF-alpha stabilizer as disclosed herein, wherein the pharmaceutically effective amount of a HIF prolyl hydroxylase inhibitor or a HIF-alpha stabilizer is suitable to increase the total iron binding capacity in the patient by at least 5%, 10%, 15%, 20%, 25%, 30%, 35%, 40%, 45%, or at least 50%. In more specific embodiments, the pharmaceutically effective amount is suitable to increase the total iron binding capacity in the patient by at least 5%, 10%, 15%, 20%, 25%, 30%, 35%, 40%, 45%, or at least 50% while the total serum iron levels are not increased, or are increased by at most 1%, 2%, 3%, 4%, 5%, 6%, 7%, 8%, 9%, 10%, 15%, 20%, or at most 25%. In certain embodiments, the HIF prolyl hydroxylase inhibitor or the HIF-alpha stabilizer is a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof. Specifically, the HIF prolyl hydroxylase inhibitor or a HIF-alpha stabilizer is Compound 1 or a pharmaceutically acceptable salt, solvate, or hydrate thereof. Specifically, the HIF prolyl hydroxylase inhibitor or a HIF-alpha stabilizer is Compound 7 or a pharmaceutically acceptable salt, solvate, or hydrate thereof.

In certain embodiments, provided herein is a method of treating or preventing an anemia in a patient, comprising administering to the patient having anemia a pharmaceutically effective amount of a HIF prolyl hydroxylase inhibitor or a HIF-alpha stabilizer as disclosed herein, wherein the pharmaceutically effective amount of a HIF prolyl hydroxylase inhibitor or a HIF-alpha stabilizer is suitable to increase the total iron binding capacity in the patient by at least 5%, 10%, 15%, 20%, 25%, 30%, 35%, 40%, 45%, or at least 50%. In more specific embodiments, the pharmaceutically effective amount is suitable to increase the total iron binding capacity in the patient by at least 5%, 10%, 15%, 20%, 25%, 30%, 35%, 40%, 45%, or at least 50% while the total serum iron levels are not increased, or are increased by at most 1%, 2%, 3%, 4%, 5%, 6%, 7%, 8%, 9%, 10%, 15%, 20%, or at most 25%. In certain embodiments, the HIF prolyl hydroxylase inhibitor or the HIF-alpha stabilizer is a compound having a structure of Formula (I), Formula (I), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof. Specifically, the HIF prolyl hydroxylase inhibitor or a HIF-alpha stabilizer is Compound 1 or a pharmaceutically acceptable salt, solvate, or hydrate thereof. Specifically, the HIF prolyl hydroxylase inhibitor or a HIF-alpha stabilizer is Compound 7 or a pharmaceutically acceptable salt, solvate, or hydrate thereof.

In certain embodiments, the anemia is, e.g., anemia secondary to or associated with chronic kidney disease, anemia secondary to chronic heart disease, idiopathic anemia of aging, anemia of chronic disease, myelodysplastic syndrome, bone marrow fibrosis, other a plastic or dysplastic anemias, chemotherapy induced anemia (including chemotherapy for treating cancer, hepatitis C, or other chronic drug therapy that reduces bone marrow production), anemia resulting from blood loss, anemia resulting from iron deficiency, anemia resulting from vitamin B12 deficiency, sickle cell disease, or thalassemia.

In certain, more specific, embodiments, the anemia is anemia secondary to chronic kidney disease (CKD) and the daily dose of the HIF prolyl hydroxylase inhibitor or HIF-alpha stabilizer may be administered orally, preferably once daily. In certain embodiments, the daily dose is administered once daily. In certain embodiments, the CKD is stage 1, 2, 3, 4, or 5 chronic kidney disease. In certain such embodiments, the CKD is stage 3, 4, or 5 chronic kidney disease. In certain embodiments, the CKD is stage 1 chronic kidney disease. In certain embodiments, the CKD is stage 2 chronic kidney disease. In certain embodiments, the CKD is stage 3 chronic kidney disease. In certain embodiments, the CKD is stage 4 chronic kidney disease. In certain embodiments, the CKD is stage 5 chronic kidney disease. In certain embodiments, the chronic kidney disease is pre-dialysis chronic kidney disease. In certain embodiments, the patient is a dialysis patient and these patients may be referred to as having end stage renal disease (ESRD). In certain such embodiments, the anemia, such as anemia secondary to CKD or ESRD may be refractory to treatment with an erythropoiesis stimulating agent, including a rhEPO product, such as, epoetin alfa, epoctin beta, darbepoctin, or peginesatide. In certain embodiments, the patient has been previously treated for anemia, while in certain alternative embodiments, the patient has not previously been treated for anemia.

In certain embodiments, the disease or condition related to diminished endogenous EPO production is anemia, such as anemia secondary to chronic kidney disease. In certain embodiments, the disease or condition that is treatable by increasing endogenous EPO production is anemia, such as anemia secondary to chronic kidney disease.

In certain embodiments, provided herein is a method of treating or preventing a disease or condition related to diminished endogenous hemoglobin production in a patient, comprising administering to the patient having disease or condition related to diminished endogenous hemoglobin production a pharmaceutically effective amount of a HIF prolyl hydroxylase inhibitor or a HIF-alpha stabilizer as disclosed herein, wherein the pharmaceutically effective amount of a HIF prolyl hydroxylase inhibitor or a HIF-alpha stabilizer is suitable to increase the total iron binding capacity in the patient by at least 5%, 10%, 15%, 20%, 25%, 30%, 35%, 40%, 45%, or at least 50%. In more specific embodiments, the pharmaceutically effective amount is suitable to increase the total iron binding capacity in the patient by at least 5%, 10%, 15%, 20%, 25%, 30%, 35%, 40%, 45%, or at least 50% while the total serum iron levels are not increased, or are increased by at most 1%, 2%, 3%, 4%, 5%, 6%, 7%, 8%, 9%, 10%, 15%, 20%, or at most 25%. In certain embodiments, the HIF prolyl hydroxylase inhibitor or the HIF-alpha stabilizer is a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11 Compound 12, Compound 13, Metabolite 1, or Metabolite 2 or a pharmaceutically acceptable salt, solvate, or hydrate thereof. Specifically, the HIF prolyl hydroxylase inhibitor or a HIF-alpha stabilizer is Compound 1 or a pharmaceutically acceptable salt, solvate, or hydrate thereof. Specifically, the HIF prolyl hydroxylase inhibitor or a HIF-alpha stabilizer is Compound 7 or a pharmaceutically acceptable salt, solvate, or hydrate thereof.

In certain embodiments, provided herein is a method of treating a disease or condition that is treatable by increasing endogenous hemoglobin production, comprising administering to a patient having a disease or condition that is treatable by increasing endogenous hemoglobin production, a pharmaceutically effective amount of a HIF prolyl hydroxylase inhibitor or a HIF-alpha stabilizer as disclosed herein, wherein the pharmaceutically effective amount of a HIF prolyl hydroxylase inhibitor or a HIF-alpha stabilizer is suitable to increase the total iron binding capacity in the patient by at least 5%, 10%, 15%, 20%, 25%, 30%, 35%, 40%, 45%, or at least 50%. In more specific embodiments, the pharmaceutically effective amount is suitable to increase the total iron binding capacity in the patient by at least 5%, 10%, 15%, 20%, 25%, 30%, 35%, 40%, 45%, or at least 50% while the total serum iron levels are not increased, or are increased by at most 1%, 2%, 3%, 4%, 5%, 6%, 7%, 8%, 9%, 10%, 15%, 20%, or at most 25%. In certain embodiments, the HIF prolyl hydroxylase inhibitor or the HIF-alpha stabilizer is a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof. Specifically, the HIF prolyl hydroxylase inhibitor or a HIF-alpha stabilizer is Compound 1 or a pharmaceutically acceptable salt, solvate, or hydrate thereof. Specifically, the HIF prolyl hydroxylase inhibitor or a HIF-alpha stabilizer is Compound 7 or a pharmaceutically acceptable salt, solvate, or hydrate thereof.

In certain embodiments, the disease or condition related to diminished endogenous hemoglobin production is anemia, such as anemia secondary to chronic kidney disease. In certain embodiments, the disease or condition that may be treated by increasing endogenous hemoglobin production is anemia, such as anemia secondary to chronic kidney disease.

In certain embodiments, serum iron may be determined using a test based on the FerroZine method without deproteinization. Specimens are analyzed on the Roche Modular Instrument utilizing Roche Diagnostics Reagents. Under acidic conditions, iron is liberated from transferrin. The detergent clarifies lipemic samples. Ascorbate reduces the released Fe3+ ions to Fe2+ ions, which then react with FerroZine to form a colored complex. The color intensity is directly proportional to the iron concentration and can be measured photometrically.

In certain embodiments, unsaturated iron binding capacity (UIBC) may be determined by adding serum to an alkaline buffer/reductant solution containing a known concentration of iron to saturate the available binding sites on transferrin. The Ferrozine chromogen reacts only with the $Fe^{2+}$; therefore, an iron reductant is added to insure that all iron is present in the ferrous state. The excess unbound divalent iron reacts with Ferrozine chromogen to form a magenta complex, which is measure spectrophotometrically. The unsaturated iron binding capacity (UIBC) is equal to the difference measured in the concentrations of the added iron solution and the excess unbound iron. Serum TIBC is equal to total serum iron plus UIBC and may therefore be calculated using the results of the UIBC and serum iron determinations.

Total iron binding capacity (TIBC) is a measure of the blood's capacity to bind iron with transferrin and is performed by drawing blood and measuring the maximum amount of iron that the blood can carry. Accordingly, the TIBC is representative of the amount of circulating transferrin, which contains two binding sites for transporting iron from iron storage sites to erythroid progenitor cells.

Serum iron level measurements determine how much iron is in the plasma. The amount of iron that is found in serum is dependent on the ability to mobilize the iron that is stored in cells. This process of iron mobilization is controlled by ferroportin and hepcidin which work in concert to regulate the amount of iron that is exported to the plasma. Ferroportin moves iron in and out of cells, while hepcidin regulates the action of ferroportin, thereby determining whether iron is released into the plasma or retained in the cell. Accordingly, it is possible to have large amounts of iron stored in cells, but relatively low levels of serum iron depending on the activity of ferroportin and hepcidin.

In certain embodiments, provided herein is a method of treating a disease or condition related to diminished endogenous production of erythropoietin (EPO), comprising administering to a patient having a disease or condition related to diminished endogenous production of EPO, a sufficient number of successive doses of a HIF prolyl hydroxylase inhibitor or a HIF-alpha stabilizer so as to raise the TIBC relative to a baseline TIBC in a patient, without significantly increasing the serum iron level relative to a baseline. In certain such embodiments, provided herein are methods of treating a disease or condition related to diminished endogenous production of EPO while minimizing the cardiovascular side-effects and risk of thromboembolic events associated with increased serum iron levels. In certain such embodiments, the disease or condition is anemia, such as anemia secondary to chronic kidney disease.

In certain embodiments, provided herein is a method of treating a disease or condition that is treatable by increasing endogenous erythropoietin (EPO) production, comprising administering to a patient having a disease or condition related to diminished endogenous production of EPO that is treatable by increasing endogenous EPO production, a sufficient number of successive doses of a HIF prolyl hydroxylase inhibitor or a HIF-alpha stabilizer so as to raise the TIBC relative to a baseline TIBC in a patient, without significantly increasing the serum iron level relative to a baseline. In certain such embodiments, provided herein are methods of treating a disease or condition that is treatable by increasing endogenous production of EPO while minimizing the cardiovascular side-effects and risk of thromboembolic events associated with increased serum iron levels. In certain such embodiments, the disease or condition is anemia, such as anemia secondary to chronic kidney disease.

In certain embodiments, the TIBC increases by about 10 μg/dL, about 20 μg/dL, about 30 μg/dL, about 40 μg/dL, about 50 μg/dL about 60 μg/dL, about 70 μg/dL, about 80 μg/dL, about 90 μg/dL or about 100 μg/dL relative to a baseline TIBC. In certain embodiments, the TIBC increases by at least about 10 μg/dL, at least about 20 μg/dL, at least about 30 μg/dL, at least about 40 μg/dL, at least about 50 μg/dL, at least about 60 μg/dL, at least about 70 μg/dL, at least about 80 μg/dL, at least about 90 μg/dL or at least about 100 μg/dL. In certain embodiments, the TIBC increases by between about 10 μg/dL and about 60 μg/dL, between about 10 μg/dL and about 50 μg/dL, between about 10 μg/dL and about 40 μg/dL, between about 10 μg/dL and about 30 μg/dL, or between about 10 μg/dL and about 20 μg/dL. In certain embodiments, the TIBC increases by between 20 μg/dL and about 60 μg/dL, between about 30 μg/dL and about 60 μg/dL, between 40 μg/dL and about 60 μg/dL, or between about 50 μg/dL and about 60 μg/dL.

In certain such embodiments, the TIBC increase occurs over about 1 week, about 2 weeks, about 3 weeks, about 4 weeks, about 5 weeks, or about 6 weeks relative to a baseline TIBC.

In certain embodiments, the serum iron level increases by less than about 20 μg/dL, less than about 15 μg/dL, less than about 10 μg/dL, or less than about 5 μg/dL relative to a baseline serum iron level. In certain embodiments, the serum iron level increases by between about 0 µg/dL and about 20 µg/dL, between about 0 µg/dL and about 15 µg/dL, between about 0 µg/dL and about 10 µg/dL, or between about 0 µg/dL and about 5 µg/dL.

5.3.3 Hepcidin Levels

Phase 2a clinical trials showed that, in stage 3, 4, or 5 CKD patients, Compound 1, a HIF prolyl hydroxylase inhibitor, was able to increase serum hemoglobin levels, at 6 weeks post administration as compared to baseline and compared to placebo treated patients. Unexpectedly, the increase in hemoglobin levels was not associated with a decrease in hepcidin levels.

In certain embodiments, provided herein are methods of treating or preventing a disease or condition related to diminished endogenous production of erythropoietin (EPO), comprising administering to a patient having a disease or condition related to diminished endogenous production of EPO a pharmaceutically effective amount of a HIF prolyl hydroxylase inhibitor or a HIF-alpha stabilizer, wherein the pharmaceutically effective amount is suitable to increase the peak levels of serum EPO during the circadian cycle by at least 10%, 15%, 20%, 25%, 30%, 35%, 40%, 45%, 50%, 55%, 60%, 65%, 70%, 75%, 80%, 85%, 90%, 95%, 100%, 110%, 120%, 130%, 140%, or at least 150% relative to the trough levels of serum EPO without decreasing the serum levels of hepcidin by more than 1%, 2%, 3%, 4%, 5%, 6%, 7%, 8%, 9%, 10%, 11%, 12%, 13%, 14%, 15%, 16%, 17%, 18%, 19%, or by more than 20% relative to hepcidin levels prior to administration of the HIF prolyl hydroxylase inhibitor or HIF-alpha stabilizer. In certain embodiments, the HIF prolyl hydroxylase inhibitor or the HIF-alpha stabilizer is a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof. Specifically, the HIF prolyl hydroxylase inhibitor or HIF-alpha stabilizer is Compound 1 or a pharmaceutically acceptable salt, solvate, or hydrate thereof. Specifically, the HIF prolyl hydroxylase inhibitor or HIF-alpha stabilizer is Compound 7 or a pharmaceutically acceptable salt, solvate, or hydrate thereof. In certain embodiments, the disease or condition that relates to diminished endogenous EPO production is anemia, such as non-severe anemia secondary to chronic kidney disease, non-severe anemia secondary to congestive heart failure, and idiopathic anemia of aging.

In certain embodiments, provided herein are methods of treating or preventing a disease or condition that is treatable by increasing endogenous production of erythropoietin (EPO), comprising administering to a patient having a disease or condition that is treatable by increasing endogenous production of EPO a pharmaceutically effective amount of a HIF prolyl hydroxylase inhibitor or a HIF-alpha stabilizer, wherein the pharmaceutically effective amount is suitable to increase the peak levels of serum EPO during the circadian cycle by at least 10%, 15%, 20%, 25%, 30%, 35%, 40%, 45%, 50%, 55%, 60%, 60%, 65%, 70%, 75%, 80%, 85%, 90%, 95%, 100%, 110%, 120%, 130%, 140%, or at least 150% relative to the trough levels of serum EPO without decreasing the serum levels of hepcidin by more than 1%, 2%, 3%, 4%, 5%, 6%, 7%, 8%, 9%, 10%, 11%, 12%, 13%, 14%, 15%, 16%, 17%, 18%, 19%, or by more than 20% relative to hepcidin levels prior to administration of the HIF prolyl hydroxylase inhibitor or HIF-alpha stabilizer. In certain embodiments, the HIF prolyl hydroxylase inhibitor or the HIF-alpha stabilizer is a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof. Specifically, the HIF prolyl hydroxylase inhibitor or HIF-alpha stabilizer is Compound 1 or a pharmaceutically acceptable salt, solvate, or hydrate thereof. Specifically, the HIF prolyl hydroxylase inhibitor or HIF-alpha stabilizer is Compound 7 or a pharmaceutically acceptable salt, solvate, or hydrate thereof. In certain embodiments, the disease or condition that is treatable by increasing endogenous EPO production is anemia, such as non-severe anemia secondary to chronic kidney disease, non-severe anemia secondary to congestive heart failure, and idiopathic anemia of aging.

In certain embodiments, provided herein are methods of treating or preventing a disease or condition related to endogenous hemoglobin production, comprising administering to a patient having disease or condition related to endogenous hemoglobin production a pharmaceutically effective amount of a HIF prolyl hydroxylase inhibitor or a HIF-alpha stabilizer, wherein the pharmaceutically effective amount is suitable to increase the peak levels of hemoglobin levels by at least 2%, 3%, 4%, 5%, 6%, 7%, 8%%, 9%, 10%, 11%, 12%, 13%, 14%, 15%, 16%, 17%, 18%, or at least 20%, relative to hepcidin levels prior to the treatment without decreasing the serum levels of hepcidin by more than 1%, 2%, 3%, 4%, 5%, 6%, 7%, 8%, 9%, 10%, 11%, 12%, 13%, 14%, 15%, 16%, 17%, 18%, 19%, or by more than 20% relative to hepcidin levels prior to administration of the HIF prolyl hydroxylase inhibitor or HIF-alpha stabilizer. In certain embodiments, the HIF prolyl hydroxylase inhibitor or the HIF-alpha stabilizer is a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof. Specifically, the HIF prolyl hydroxylase inhibitor or HIF-alpha stabilizer is Compound 1 or a pharmaceutically acceptable salt, solvate, or hydrate thereof. Specifically, the HIF prolyl hydroxylase inhibitor or HIF-alpha stabilizer is Compound 7 or a pharmaceutically acceptable salt, solvate, or hydrate thereof. In certain embodiments, the disease or condition that relates to diminished endogenous hemoglobin production is anemia, such as non-severe anemia secondary to chronic kidney disease, non-severe anemia secondary to congestive heart failure, and idiopathic anemia of aging.

In certain embodiments, provided herein are methods of treating or preventing a disease or condition that is treatable by increasing endogenous hemoglobin production, comprising administering to a patient having disease or condition that is treatable by increasing endogenous hemoglobin production a pharmaceutically effective amount of a HIF prolyl hydroxylase inhibitor or a HIF-alpha stabilizer, wherein the pharmaceutically effective amount is suitable to increase the peak levels of hemoglobin levels by at least 2%, 3%, 4%, 5%, 6%, 7%, 8%, 9%, 10%, 11%, 12%, 13%, 14%, 15%, 16%, 17%, 18%, or at least 20%, relative to hepcidin levels prior to the treatment without decreasing the serum levels of hepcidin by more than 1%, 2%, 3%, 4%, 5%, 6%, 7%, 8%, 9%, 10%, 11%, 12%, 13%, 14%, 15%, 16%, 17%, 18%, 19%, or by more than 20% relative to hepcidin levels prior to administration of the HIF prolyl hydroxylase inhibitor or HIF-alpha stabilizer. In certain embodiments, the HIF prolyl hydroxylase inhibitor or the HIF-alpha stabilizer is a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof. Specifically, the HIF prolyl hydroxylase inhibitor or HIF-alpha stabilizer is Compound 1 or a pharmaceutically acceptable salt, solvate, or hydrate thereof. Specifically, the HIF prolyl hydroxylase inhibitor or HIF-alpha stabilizer is Compound 7 or a pharmaceutically acceptable salt, solvate, or hydrate thereof. In certain embodiments, the disease or condition that is treatable by increasing endogenous EPO production is anemia, such as non-severe anemia secondary to chronic kidney disease, non-severe anemia secondary to congestive heart failure, and idiopathic anemia of aging.

In certain embodiments, provided herein are methods of treating or preventing an anemia in a patient, comprising administering to the patient having the anemia a pharmaceutically effective amount of a HIF prolyl hydroxylase inhibitor or a HIF-alpha stabilizer, wherein the pharmaceutically effective amount is suitable to increase the peak levels of hemoglobin levels by at least 2%, 3%, 4%, 5%, 6%, 7%, 8%, 9%, 10%, 11%, 12%, 13%, 14%, 15%, 16%, 17%, 18%, or at least 20%, relative to hepcidin levels prior to the treatment without decreasing the serum levels of hepcidin by more than 1%, 2%, 3%, 4%, 5%, 6%, 7%, 8%, 9%, 10%, 11%, 12%, 13%, 14%, 15%, 16%, 17%, 18%, 19%, or by more than 20% relative to hepcidin levels prior to administration of the HIF prolyl hydroxylase inhibitor or HIF-alpha stabilizer. In certain embodiments, the HIF prolyl hydroxylase inhibitor or the HIF-alpha stabilizer is a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof. Specifically, the HIF prolyl hydroxylase inhibitor or HIF-alpha stabilizer is Compound 1 or a pharmaceutically acceptable salt, solvate, or hydrate thereof. Specifically, the HIF prolyl hydroxylase inhibitor or HIF-alpha stabilizer is Compound 7 or a pharmaceutically acceptable salt, solvate, or hydrate thereof. In certain embodiments, the disease or condition that is treatable by increasing endogenous EPO production is anemia, such as non-severe anemia secondary to chronic kidney disease (CKD), non-severe anemia secondary to congestive heart failure, and idiopathic anemia of aging. In certain embodiments, the anemia is, e.g., anemia secondary to or associated with chronic kidney disease, anemia secondary to chronic heart disease, idiopathic anemia of aging, anemia of chronic disease, myelodysplastic syndrome, bone marrow fibrosis, other aplastic or dysplastic anemias, chemotherapy induced anemia (including chemotherapy for treating cancer, hepatitis C, or other chronic drug therapy that reduces bone marrow production), anemia resulting from blood loss, anemia resulting from iron deficiency, anemia resulting from vitamin B12 deficiency, sickle cell disease, or thalassemia).

In certain embodiments, such daily doses may be administered orally, preferably once daily. In certain embodiments, the daily dose is administered once daily, in certain embodiments, the CKD is stage 1, 2, 3, 4, or 5 chronic kidney disease. In certain such embodiments, the CKD is stage 3, 4, or 5 chronic kidney disease. In certain embodiments, the CKD is stage 1 chronic kidney disease. In certain embodiments, the CKD is stage 2 chronic kidney disease. In certain embodiments, the CKD is stage 3 chronic kidney disease. In certain embodiments, the CKD is stage 4 chronic kidney disease. In certain embodiments, the CKD is stage 5 chronic kidney disease. In certain embodiments, the chronic kidney disease is pre-dialysis chronic kidney disease. In certain embodiments, the patient is a dialysis patient and these patients may be referred to as having end stage renal disease (ESRD). In certain such embodiments, the anemia, such as anemia secondary to CKD or ESRD may be refractory to treatment with an erythropoiesis stimulating agent, including a rhEPO product, such as, epoetin alfa, epoetin beta, darbepoetin, or peginesatide. In certain embodiments, the patient has been previously treated for anemia, while in certain alternative embodiments, the patient has not previously been treated for anemia.

In certain embodiments, hepcidin expression may be determined, as described in Ganz, T. et al., "Immunoassay for human serum hepcidin" Blood 112: 4292-4297 (2008). Briefly, the antibody to human hepcidin was purified on staphylococcal protein A columns according to the manufacturer's protocol; 96-well plates were coated with the antibody and incubated with 100 µL (standard samples) or 200 µL (samples with very low concentration of hepcidin) of 1:20 dilution of serum or 1:10 dilution of urine in Tris-buffered saline containing 0.05% Tween-20 (TBS-Tween 20), with 10 ng/mL of biotinylated hepcidin-25 added as the tracer. Standard curves were prepared by serial 2-fold dilution of synthetic hepcidin 4000 ng/mL in TBS-Tween 20 buffer containing the tracer. The integrity and bioactivity of synthetic hepcidin and biotinylated hepcidin were verified by mass spectrometry and by bioassay with ferroportin-green fluorescent protein expressing HEK-293 cells. After washing, the assay was developed with streptavidin-peroxidase and tetramethyl benzidine. The enzymatic reaction was stopped by sulfuric acid, and the plate was read at 450 nm on a DTX 880 microplate reader. Standard curves were fitted with 12-point fit using GraphPad Prism software. The fitted curve was then used to convert sample absorbance readings to hepcidin concentrations.

Serum hemoglobin levels may be determined, for example using standard approach CBC where red cells are lysed and potassium ferricyanide oxidizes hemoglobin to methemoglobin, which combines with potassium cyanide forming cyanmethemoglobin. The brown color is measured spectrophotometrically and the corresponding hemoglobin reported.

In certain embodiments, provided herein are methods of treating a disease or condition related to diminished endogenous production of erythropoietin (EPO), comprising administering to a patient having a disease or condition related to diminished endogenous production of EPO, a sufficient number of successive doses of a HIF prolyl hydroxylase inhibitor or a HIF-alpha stabilizer so as to raise the serum hemoglobin level relative to a baseline serum hemoglobin level, without significantly increasing hepcidin relative to a baseline level. In certain embodiments, the disease or condition related to diminished endogenous EPO production is selected from non-severe anemia secondary to chronic kidney disease, non-severe anemia secondary to congestive heart failure, and idiopathic anemia of aging.

In certain embodiments, provided herein are methods of treating a disease or condition that is treatable by increasing endogenous production of erythropoietin (EPO), comprising administering to a patient having a disease or condition that is treatable by increasing endogenous EPO production, a sufficient number of successive doses of a HIF prolyl hydroxylase inhibitor or a HIF-alpha stabilizer so as to raise the serum hemoglobin level relative to a baseline serum hemoglobin level, without significantly increasing hepcidin relative to a baseline level. In certain such embodiments, the disease or condition is anemia, such as non-severe anemia secondary to chronic kidney disease, non-severe anemia secondary to congestive heart failure, or idiopathic anemia of aging. In certain embodiments, the disease or condition that is treatable by increasing endogenous EPO production is selected from non-severe anemia secondary to chronic kidney disease, non-severe anemia secondary to congestive heart failure, and idiopathic anemia of aging.

In certain embodiments, the level of serum hemoglobin is raised by between about 0.1 and about 1.0 g/dL, between about 0.1 and about 0.9 g/dL, about 0.1 and about 0.8 g/dL, about 0.1 and about 0.7 g/dL, about 0.1 and about 0.6 g/dL, or about 0.1 and about 0.5 g/dL over a period of time, such as about one week, about two weeks, about three weeks, about four weeks, about five weeks, or about six weeks relative to the baseline hemoglobin level, in certain embodiments, the level of hemoglobin is raised by at least about 0.1 g/dL, about 0.2 g/dL, about 0.3 g/dL, about 0.4 g/dL, about 0.5 g/dL, about 0.6 g/dL, about 0.7 g/dL, about 0.8 g/dL, about 0.9, or about 1.0 g/dL over a period of time, such as about one week, about two weeks, about three weeks, about four weeks, about five weeks, or about six weeks relative to the baseline hemoglobin level.

In certain embodiments, the level of hemoglobin is raised by about 0.1 g/dL over a period of one week relative to the baseline hemoglobin level. In certain embodiments, the level of hemoglobin is raised by about 0.1 g/dL over a period of two weeks relative to the baseline hemoglobin level. In certain embodiments, the level of hemoglobin is raised by about 0.5 g/dL over a period of three weeks relative to the baseline hemoglobin level. In certain embodiments, the level of hemoglobin is raised by about 0.6 g/dL over a period of four weeks relative to the baseline hemoglobin level. In certain embodiments, the level of hemoglobin is raised by about 0.6 g/dL over a period of five weeks relative to the baseline hemoglobin level. In certain embodiments, the level of hemoglobin is raised by about 0.6 g/dL over a period of six weeks relative to the baseline hemoglobin level.

In certain embodiments, hepcidin expression decreases less than about 20%, less than about 15%, less than about 10%, less than about 5%, less than about 4%, less than about 3%, less than about 2%, or less than about 1% relative to the baseline hepcidin expression level. In certain embodiments, hepcidin expression decreases by between about 0% and about 20%, between about 0% and about 15%, between about 0% and about 10%, or between about 0% and about 5%, between about 0% and about 4%, between about 0% and about 3%, between about 0% and about 2%, or between about 0% and about 1% relative to the baseline hepcidin expression level. In certain embodiments, hepcidin expression decreases by about 20%, about 15%, about 10%, about 5%, about 4%, about 3%, about 2%, or about 1% relative to the baseline hepcidin expression level.

5.3.4 Erythroferrone Levels

In certain embodiments, provided herein is a method of treating a disease or condition selected from non-severe anemia secondary to chronic kidney disease, non-severe anemia secondary to congestive heart failure, and idiopathic anemia of aging, comprising administering to a patient having non-severe anemia secondary to chronic kidney disease, non-severe anemia secondary to congestive heart failure, or idiopathic anemia of aging a sufficient number of successive doses of a HIF prolyl hydroxylase inhibitor or a HIF-alpha stabilizer so as to raise the serum hemoglobin levels relative to a baseline serum hemoglobin level in a patient, without significantly increasing erythroferrone expression relative to a baseline erythroferrone expression level.

In certain embodiments, the serum hemoglobin level is raised by between about 0.1 and about 1.0 g/dL over a period of one week relative to the baseline hemoglobin level. In certain such embodiments, the serum hemoglobin level is raised by about 0.1 g/dL over a period of one week relative to the baseline hemoglobin level.

In certain embodiments, the serum hemoglobin level is raised by between about 0.1 and about 1.0 g/dL over a period of two weeks relative to the baseline hemoglobin level. In certain such embodiments, the serum hemoglobin level is raised by about 0.1 g/dL over a period of two weeks relative to the baseline hemoglobin level.

In certain embodiments, the serum hemoglobin level is raised by between about 0.1 and about 1.0 g/dL over a period of three weeks relative to the baseline hemoglobin level. In certain such embodiments, the serum hemoglobin level is raised by about 0.5 g/dL over a period of three weeks relative to the baseline hemoglobin level.

In certain embodiments, the serum hemoglobin level is raised by between about 0.1 and about 1.0 g/dL over a period of four weeks relative to the baseline hemoglobin level. In certain such embodiments, the serum hemoglobin level is raised by about 0.6 g/dL over a period of four weeks relative to the baseline hemoglobin level.

In certain embodiments, the serum hemoglobin level is raised by between about 0.1 and about 1.0 g/dL over a period of five weeks relative to the baseline hemoglobin level. In certain such embodiments, the serum hemoglobin level is raised by about 0.6 g/dL over a period of five weeks relative to the baseline hemoglobin level.

In certain embodiments, the serum hemoglobin level is raised by between about 0.1 and about 1.0 g/dL over a period of six weeks relative to the baseline hemoglobin level. In certain such embodiments, the serum hemoglobin level is raised by about 0.6 g/dL over a period of six weeks relative to the baseline hemoglobin level.

In certain embodiments, erythroferrone transcription increases less than about 20%, less than about 15%, less than about 10% relative to the baseline erythroferrone transcription level, less than about 5%, less than about 4%, less than about 3%, less than about 2%, or less than about 1% relative to the baseline erythroferrone transcription level, as measured by, for example, qRT-PCR of RNA (see SEQ ID NO: 3).

In certain embodiments, erythroferrone protein expression increases less than about 20%, less than about 15%, less than about 10% relative to the baseline erythroferrone expression level, less than about 5%, less than about 4%, less than about 3%, less than about 2%, or less than about 1% relative to the baseline erythroferrone expression level, as measured by, for example, western blot of erythroferrone protein (see SEQ ID NO: 2).

In certain embodiments, the disease or condition is non-severe anemia secondary to chronic kidney disease. In certain embodiments, the disease or condition is non-severe congestive heart failure. In certain embodiments, the disease or condition is idiopathic anemia of aging.

In certain embodiments, the HIF prolyl hydroxylase inhibitor or HIF-alpha stabilizer is administered once daily. In certain embodiments, the HIF prolyl hydroxylase inhibitor or HIF-alpha stabilizer is administered orally.

In certain embodiments, the HIF prolyl hydroxylase inhibitor or HIF-alpha stabilizer is a heterocyclic carboxamide. In certain such embodiments, the HIF prolyl hydroxylase inhibitor or HIF-alpha stabilizer is selected from a pyridine carboxamide, a quinoline carboxamide, and an isoquinoline carboxamide.

In certain embodiments, the HIF prolyl hydroxylase inhibitor or HIF-alpha stabilizer is a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, and Metabolite 2 or a pharmaceutically acceptable salt, solvate, or hydrate thereof. In a specific embodiment, the HIF prolyl hydroxylase inhibitor or HIF-alpha stabilizer is Compound 1 or a pharmaceutically acceptable salt, solvate, or hydrate thereof. In a specific embodiment, the HIF prolyl hydroxylase inhibitor or HIF-alpha stabilizer is Compound 7 or a pharmaceutically acceptable salt, solvate, or hydrate thereof.

5.4 Diseases Associated With Hif Prolyl Hydroxylase Modulation

The present disclosures also relate to methods for treating and/or preventing and/or controlling, inter alia, Peripheral Vascular Disease (PVD); Coronary Artery Disease (CAD); heart failure; ischemia; anemia; wound healing; ulcers; ischemic ulcers; inadequate blood supply; poor capillary circulation; small artery atherosclerosis; venous stasis; atherosclerotic lesions (e.g., in coronary arteries); angina; myocardial infarction; diabetes; hypertension Burgers disease; diseases associated with abnormal levels of VEGF, GAPDH, and/or EPO; Crohn's disease; ulcerative colitis; psoriasis; sarcoidosis; rheumatoid arthritis; hemangiomas; Osler-Weber-Rendu disease; hereditary hemorrhagic telangiectasia; solid or blood borne tumors and acquired immune deficiency syndrome; atrial arrhythmias; ischemic tissue damage in tissues such as: cardiac tissue, such as myocardium and cardiac ventricles, skeletal muscle, neurological tissue, such as from the cerebellum, internal organs, such as the stomach, intestine, pancreas, liver, spleen, and lung; and distal appendages such as fingers and toes. Specifically, provided herein are methods for treating and/or preventing and/or controlling, inter alia. Peripheral Vascular Disease (PVD); Coronary Artery Disease (CAD); heart failure; ischemia; anemia; wound healing; ulcers; ischemic ulcers; inadequate blood supply; poor capillary circulation; small artery atherosclerosis; venous stasis; atherosclerotic lesions (e.g., in coronary arteries); angina; myocardial infarction; diabetes; hypertension; Burgers disease; diseases associated with abnormal levels of VEGF, GAPDH, and/or EPO; Crohn's disease; ulcerative colitis; psoriasis; sarcoidosis; rheumatoid arthritis; hemangiomas; Osler-Weber-Rendu disease; hereditary hemorrhagic telangiectasia; solid or blood borne tumors and acquired immune deficiency syndrome; atrial arrhythmias; ischemic tissue damage in tissues such as: cardiac tissue, such as myocardium and cardiac ventricles, skeletal muscle, neurological tissue, such as from the cerebellum, internal organs, such as the stomach, intestine, pancreas, liver, spleen, and lung; and distal appendages such as fingers and toes, wherein the method comprises administering a pharmaceutically effective amount of a HIF prolyl hydroxylase inhibitor or a HIF-alpha stabilizer, wherein the pharmaceutically effective amount is suitable to reduce the severity or frequency of at least one symptom of these diseases while:
a) restoring or maintaining the diurnal pattern of EPO serum levels;
b) increasing the total iron binding capacity;
c) increasing the total iron binding capacity without increasing significantly the total iron levels; and/or
d) not significantly decreasing hepcidin levels.

Atherosclerotic PVD can present in three ways:
1) Asymptomatic PVD diagnosed on the basis of noninvasive testing (usually physical exam);
2) Intermittent claudication with symptoms of leg pain with exercise; and
3) Critical limb ischemia with leg pain at rest and limb-threatening ischemic changes (usually non-healing or infected cutaneous ulcerations).

The present disclosures also relate to methods for regulating blood flow, oxygen delivery and/or energy utilization in ischemic tissues, wherein the methods can comprise administering to a human an effective amount of one or more compounds or pharmaceutically acceptable salts or tautomers thereof disclosed herein.

The compounds and compositions recited herein can have a number of utilities, and address several unmet medical needs, inter alia:
1) Providing compositions effective as inhibitors of HIF prolyl hydroxylase, thereby stimulating an angiogenic response in human tissue, thereby providing a method for increasing blood flow, oxygen delivery and energy utilization in ischemic tissues;
2) Providing compositions effective as human protein HIF prolyl hydroxylase inhibitors, and thereby increasing the concentration of HIF-1 alpha leading to greater activation and sustaining the of various biological pathways that are the normal response to cellular hypoxia;
3) Providing compositions effective in stimulating an EPO response in cells and thereby enhancing the maintenance of red blood cells by controlling the proliferation and differentiation of erythroid progenitor cells into red blood cells;
4) Providing compositions effective in stimulating an angiogenic response and thereby increasing the number and density of blood vessels and thus alleviating the adverse consequences of hypertension and diabetes, inter alia, claudication, ischemic ulcers, accelerated hypertension, and renal failure;
5) Providing compositions that activate Vascular Endothelial Growth Factor (VEGF) gene transcription in hypoxic cells thus increasing stimulus of important biological responses, inter alia, vasodilation, vascular permeability, and endothelial cell migration and proliferation.
6) Providing compositions that induce the production of soluble VEGF, an inhibitor of VEGF, in hypoxic cells thus increasing stimulus of important biological responses, inter alia, anti-angiogenic activities;

Therefore, these and other unmet medical needs are resolved by the HIF prolyl hydroxylase inhibitors of the present disclosure, which are capable of regulating blood flow, oxygen delivery and energy utilization in ischemic tissues that are caused by insufficient regulation of HIF prolyl hydroxylase. Those of skill in the art will also recognize that inhibition of HIF-1-alpha prolyl hydroxylase enzymes will have other positive medical effects on human tissue and the alleviation of symptoms and disease states other than those symptoms or diseases states that are specifically pointed out in the present disclosure. However, as greater details arise concerning disease states and conditions related to the angiogenic process, these yet undisclosed or yet unknown conditions will be positively affected by compositions which stimulate the body own response to hypoxia and other low blood oxygen conditions.

In certain embodiments, provided herein are methods for treating or preventing a disease or disorder ameliorated by modulation of HIF prolyl hydroxylase comprising administering to a patient having a disease ameliorated by modulation of HIF prolyl hydroxylase an effective amount of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, {[5-(3-chlorophenyl)-3-hydroxypyridine-2-carbonyl]amino}acetic acid or 2-(5-(3-fluorophenyl)-3-hydroxypicolinamido)acetic acid) according to the dose and/or dosing regimen described herein. In certain such embodiments, the compound is administered from one to three, such as one, two or three times in the course of a 24 hour period. In certain such embodiments, provided herein are methods for treating or preventing a disease ameliorated by modulation of HIF prolyl hydroxylase comprising administering to a patient having a disease or disorder ameliorated by modulation of HIF prolyl hydroxylase an effective amount of {[5-(3-chlorophenyl)-3-hydroxypyridine-2-carbonyl]amino}acetic acid once daily. In certain such embodiments, the daily dose is about 150 mg, about 300 mg, about 450 mg, about 600 mg, or about 750 mg of {[5-(3-chlorophenyl)-3-hydroxypyridine-2-carbonyl]amino}acetic acid. In certain such embodiments, provided herein are methods for treating or preventing a disease ameliorated by modulation of HIF prolyl hydroxylase comprising administering to a patient having a disease or disorder ameliorated by modulation of HIF prolyl hydroxylase an effective amount of 2-(5-(3-fluorophenyl)-3-hydroxypicolinamido)acetic acid once daily. In certain such embodiments, the daily dose is about 150 mg, about 300 mg, about 450 mg, about 600 mg, or about 750 mg of 2-(5-(3-fluorophenyl)-3-hydroxypicolinamido)acetic acid. In certain such embodiments, the daily dose is about 150 mg, about 300 mg, about 450 mg, or about 600 mg. Such daily doses may be administered orally, once daily, twice daily, or three times daily, preferably once daily.

In certain embodiments, provided herein are methods of treating or preventing a disease or disorder ameliorated by inhibiting HIF prolyl hydroxylase (e.g., PHD1, PHD2, and/or PHD3), comprising administering to a patient having a disease or disorder ameliorated by inhibiting HIF prolyl hydroxylase an effective amount of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, 5-(3-chlorophenyl)-3-hydroxypyridine-2-carbonyl]amino}acetic acid or 2-(5-(3-fluorophenyl)-3-hydroxypicolinamido)acetic acid) according to the dose and/or dosing regimen described herein. In certain such embodiments, the daily dose is about 150 mg, about 300 mg, about 450 mg, about 600 mg, or about 750 mg of {[5-(3-chlorophenyl)-3-hydroxypyridine-2-carbonyl]amino}acetic acid. In certain such embodiments, the daily dose is about 150 mg, about 300 mg, about 450 mg, about 600 mg, or about 750 mg of 2-(5-(3-fluorophenyl)-3-hydroxypicolinamido)acetic acid. In certain such embodiments, the daily dose is about 150 mg, about 300 mg, about 450 mg, or about 600 mg. Such daily doses may be administered orally, once daily, twice daily, or three times daily, preferably once daily. In certain such embodiments, provided herein are methods of treating or preventing a disease or disorder ameliorated by inhibiting PHD1, comprising administering to a patient having a disease or disorder ameliorated by inhibiting PHD1 an effective amount of 5-(3-chlorophenyl)-3-hydroxypyridine-2-carbonyl]amino}acetic acid according to the dose and/or dosing regimen described herein. In certain such embodiments, provided herein are methods of treating or preventing a disease or disorder ameliorated by inhibiting PHD1, comprising administering to a patient having a disease or disorder ameliorated by inhibiting PHD1 an effective amount of 2-(5-(3-fluorophenyl)-3-hydroxypicolinamido)acetic acid according to the dose and/or dosing regimen described herein. In certain such embodiments, provided herein are methods of treating or preventing a disease or disorder ameliorated by inhibiting PHD2, comprising administering to a patient having a disease or disorder ameliorated by inhibiting PHD2 an effective amount of 5-(3-chlorophenyl)-3-hydroxypyridine-2-carbonyl]amino}acetic acid according to the dose and/or dosing regimen described herein. In certain such embodiments, provided herein are methods of treating or preventing a disease or disorder ameliorated by inhibiting PHD2, comprising administering to a patient having a disease or disorder ameliorated by inhibiting PHD2 an effective amount of 2-(5-(3-fluorophenyl)-3-hydroxypicolinamido)acetic acid according to the dose and/or dosing regimen described herein. In certain such embodiments, provided herein are methods of treating or preventing a disease or disorder ameliorated by inhibiting PHD3, comprising administering to a patient having a disease or disorder ameliorated by inhibiting PHD3 an effective amount of 5-(3-chlorophenyl)-3-hydroxypyridine-2-carbonyl]amino}acetic acid according to the dose and/or dosing regimen described herein. In certain such embodiments, provided herein are methods of treating or preventing a disease or disorder ameliorated by inhibiting PHD3, comprising administering to a patient having a disease or disorder ameliorated by inhibiting PHD3 an effective amount of 2-(5-(3-fluorophenyl)-3-hydroxypicolinamido)acetic acid according to the dose and/or dosing regimen described herein.

In certain embodiments, provided herein are methods of treating or preventing a disease or disorder ameliorated by stabilizing HIF-alpha (e.g., HIF-1-alpha, HIF-2-alpha, and/or HIF-3-alpha), comprising administering to a patient having a disease or disorder ameliorated by stabilizing HIF-alpha an effective amount of a compound having a structure of Formula (I), Formula (II), Formula (I), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, 5-(3-chlorophenyl)-3-hydroxypyridine-2-carbonyl]amino}acetic acid or 2-(5-(3-fluorophenyl)-3-hydroxypicolinamido)acetic acid) according to the dose and/or dosing regimen described herein. In certain such embodiments, the daily dose is about 150 mg, about 300 mg, about 450 mg, about 600 mg, or about 750 mg of {[5-(3-chlorophenyl)-3-hydroxypyridine-2-carbonyl]amino}acetic acid. In certain such embodiments, the daily dose is about 150 mg, about 300 mg, about 450 mg, or about 600 mg. In certain such embodiments, the daily dose is about 150 mg, about 300 mg, about 450 mg, about 600 mg, or about 750 mg of 2-(5-(3-fluorophenyl)-3-hydroxypicolinamido)acetic acid. In certain such embodiments, the daily dose is about 150 mg, about 300 mg, about 450 mg, or about 600 mg. Such daily doses may be administered orally, once daily, twice daily, or three times daily, preferably once daily. In certain such embodiments, provided herein are methods of treating or preventing a disease or disorder ameliorated by stabilizing HIF-1α, comprising administering to a patient having a disease or disorder ameliorated by stabilizing HIF-1-alpha an effective amount of 5-(3-chlorophenyl)-3-hydroxypyridine-2-carbonyl]amino}acetic acid according to the dose and/or dosing regimen described herein. In certain such embodiments, provided herein are methods of treating or preventing a disease or disorder ameliorated by stabilizing HIF-1α, comprising administering to a patient having a disease or disorder ameliorated by stabilizing HIF-1-alpha an effective amount of 2-(5-(3-fluorophenyl)-3-hydroxypicolinamido)acetic acid according to the dose and/or dosing regimen described herein. In certain such embodiments, provided herein are methods of treating or preventing a disease or disorder ameliorated by stabilizing HIF-2-alpha, comprising administering to a patient having a disease or disorder ameliorated by inhibiting HIF-2-alpha an effective amount of 5-(3-chlorophenyl)-3-hydroxypyridine-2-carbonyl]amino}acetic acid according to the dose and/or dosing regimen described herein. In certain such embodiments, provided herein are methods of treating or preventing a disease or disorder ameliorated by stabilizing HIF-2-alpha, comprising administering to a patient having a disease or disorder ameliorated by inhibiting HIF-2-alpha an effective amount of 2-(5-(3-fluorophenyl)-3-hydroxypicolinamido)acetic acid according to the dose and/or dosing regimen described herein.

In certain such embodiments, provided herein are methods of treating or preventing a disease or disorder ameliorated by stabilizing HIF-3-alpha, comprising administering to a patient having a disease or disorder ameliorated by stabilizing HIF-3-alpha an effective amount of 5-(3-chlorophenyl)-3-hydroxypyridine-2-carbonyl]amino}acetic acid according to the dose and/or dosing regimen described herein. In certain such embodiments, provided herein are treating or preventing a disease or disorder ameliorated by stabilizing HIF-3-alpha, comprising administering to a patient having a disease or disorder ameliorated by stabilizing HIF-3-alpha an effective amount of 2-(5-(3-fluorophenyl)-3-hydroxypicolinamido)acetic acid according to the dose and/or dosing regimen described herein.

In certain embodiments, provided herein are methods of treating or preventing a disease or condition related to diminished endogenous production of erythropoietin (EPO), comprising administering to a patient having a disease or disorder related to diminished endogenous production of EPO an effective amount of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, 5-(3-chlorophenyl)-3-hydroxypyridine-2-carbonyl]amino}acetic acid or 2-(5-(3-fluorophenyl)-3-hydroxypicolinamido)acetic acid) according to the dose and/or dosing regimens described herein. In certain such embodiments, the daily dose is about 150 mg, about 300 mg, about 450 mg, about 600 mg, or about 750 mg of {[5-(3-chlorophenyl)-3-hydroxypyridine-2-carbonyl]amino}acetic acid. In certain such embodiments, the daily dose is about 150 mg, about 300 mg, about 450 mg, about 600 mg, or about 750 mg of 2-(5-(3-fluorophenyl)-3-hydroxypicolinamido)acetic acid. In certain such embodiments, the daily dose is about 150 mg, about 300 mg, about 450 mg, or about 600 mg. Such daily doses may be administered orally, once daily, twice daily, or three times daily, preferably once daily.

In certain embodiments, provided herein are methods of treating or preventing anemia (e.g., anemia secondary to or associated with chronic kidney disease, anemia secondary to chronic heart disease, idiopathic anemia of aging, anemia of chronic disease, myelodysplastic syndrome, bone marrow fibrosis, other aplastic or dysplastic anemias, chemotherapy induced anemia (including chemotherapy for treating cancer, hepatitis C, or other chronic drug therapy that reduces bone marrow production), anemia resulting from blood loss, anemia resulting from iron deficiency, anemia resulting from vitamin B12 deficiency, sickle cell disease, or thalassemia), comprising administering to a patient having anemia an effective amount of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11 Compound 12, Compound 13, Metabolite 1, or Metabolite 2 or a pharmaceutically acceptable salt, solvate, or hydrate thereof (specifically, 5-(3-chlorophenyl)-3-hydroxypyridine-2-carbonyl]amino}acetic acid or 2-(5-(3-fluorophenyl)-3-hydroxypicolinamido)acetic acid) according to the dose and/or dosing regimen described herein. In certain embodiments, provided herein are methods of treating anemia, such as anemia secondary to chronic kidney disease, comprising administering to a patient having anemia an effective amount of 5-(3-chlorophenyl)-3-hydroxypyridine-2-carbonyl]amino}acetic acid. In certain embodiments, provided herein are methods of treating anemia, such as anemia secondary to chronic kidney disease, comprising administering to a patient having anemia an effective amount of 2-(5-(3-fluorophenyl)-3-hydroxypicolinamido)acetic acid. In certain such embodiments, the daily dose is about 150 mg, about 300 mg, about 450 mg, about 600 mg, or about 750 mg of {[5-(3-chlorophenyl)-3-hydroxypyridine-2-carbonyl]amino}acetic acid. In certain such embodiments, the daily dose is about 150 mg, about 300 mg, about 450 mg, about 600 mg, or about 750 mg of 2-(5-(3-fluorophenyl)-3-hydroxypicolinamido)acetic acid. In certain such embodiments, the daily dose is about 150 mg, about 300 mg, about 450 mg, or about 600 mg. Such daily doses may be administered orally, once daily, twice daily, or three times daily, preferably once daily.

In certain embodiments, provided herein are treating or preventing anemia secondary to chronic kidney disease (CKD), comprising administering to a patient having anemia secondary to CKD an effective amount of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, 5-(3-chlorophenyl)-3-hydroxypyridine-2-carbonyl]amino}acetic acid or 2-(5-(3-fluorophenyl)-3-hydroxypicolinamido)acetic acid) according to the dose and/or dosing regimen described herein. In certain such embodiments, the daily dose is about 150 mg, about 300 mg, about 450 mg, about 600 mg, or about 750 mg of {[5-(3-chlorophenyl)-3-hydroxypyridine-2-carbonyl]amino}acetic acid. In certain such embodiments, the daily dose is about 150 mg, about 300 mg, about 450 mg, about 600 mg, or about 750 mg of 2-(5-(3-fluorophenyl)-3-hydroxypicolinamido)acetic acid. In certain such embodiments, the daily dose is about 150 mg, about 300 mg, about 450 mg, or about 600 mg. Such daily doses may be administered orally, once daily, twice daily, or three times daily, preferably once daily. In certain embodiments, the daily dose is administered once daily. In certain embodiments, the CKD is stage 1, 2, 3, 4, or 5 chronic kidney disease. In certain such embodiments, the CKD is stage 3, 4, or 5 chronic kidney disease. In certain embodiments, the CKD is stage 1 chronic kidney disease. In certain embodiments, the CKD is stage 2 chronic kidney disease. In certain embodiments, the CKD is stage 3 chronic kidney disease. In certain embodiments, the CKD is stage 4 chronic kidney disease. In certain embodiments, the CKD is stage 5 chronic kidney disease. In certain embodiments, the chronic kidney disease is pre-dialysis chronic kidney disease. In certain embodiments, the patient is a dialysis patient and these patients may be referred to as having end stage renal disease (ESRD). In certain such embodiments, the anemia, such as anemia secondary to CKD or ESRD may be refractory to treatment with an erythropoiesis stimulating agent, including a rhEPO product, such as, epoetin alfa, epoetin beta, darbepoetin, or peginesatide. In certain embodiments, the patient has been previously treated for anemia, while in certain alternative embodiments, the patient has not previously been treated for anemia.

In certain embodiments, provided herein are methods of treating or preventing an angiogenesis-related disease or disorder, comprising administering to a patient having angiogenesis-related disease or disorder an effective amount of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, 5-(3-chlorophenyl)-3-hydroxypyridine-2-carbonyl]amino}acetic acid or 2-(5-(3-fluorophenyl)-3-hydroxypicolinamido)acetic acid) according to the dose and/or dosing regimen described herein. In certain embodiments, provided herein are methods of regulating angiogenesis, comprising administering to a patient an effective amount of 5-(3-chlorophenyl)-3-hydroxypyridine-2-carbonyl]amino}acetic acid according to the dose and/or dosing regimen described herein. In certain embodiments, provided herein are methods of regulating angiogenesis, comprising administering to a patient an effective amount of 2-(5-(3-fluorophenyl)-3-hydroxypicolinamido)acetic acid according to the dose and/or dosing regimen described herein. In certain such embodiments, the daily dose is about 150 mg, about 300 mg, about 450 mg, about 600 mg, or about 750 mg of {[5-(3-chlorophenyl)-3-hydroxypyridine-2-carbonyl]amino}acetic acid. In certain such embodiments, the daily dose is about 150 mg, about 300 mg, about 450 mg, about 600 mg, or about 750 mg of 2-(5-(3-fluorophenyl)-3-hydroxypicolinamido)acetic acid. In certain such embodiments, the daily dose is about 150 mg, about 300 mg, about 450 mg, or about 600 mg. Such daily doses may be administered orally, once daily, twice daily, or three times daily, preferably once daily.

In certain embodiments, provided herein are methods of treating or preventing disease or disorder affected by the level of VEGF or GAPDH, comprising administering to a patient having a disease or disorder affected by the level of VEGF or GADPH an effective amount of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, 5-(3-chlorophenyl)-3-hydroxypyridine-2-carbonyl]amino}acetic acid or 2-(5-(3-fluorophenyl)-3-hydroxypicolinamido)acetic acid) according to the dose and/or dosing regimen described herein. In certain such embodiments, the daily dose is about 150 mg, about 300 mg, about 450 mg, about 600 mg, or about 750 mg of {[5-(3-chlorophenyl)-3-hydroxypyridine-2-carbonyl]amino}acetic acid. In certain such embodiments, the daily dose is about 150 mg, about 300 mg, about 450 mg, about 600 mg, or about 750 mg of 2-(5-(3-fluorophenyl)-3-hydroxypicolinamido)acetic acid. In certain such embodiments, the daily dose is about 150 mg, about 300 mg, about 450 mg, or about 600 mg. Such daily doses may be administered orally, once daily, twice daily, or three times daily, preferably once daily.

In certain embodiments, provided herein are methods of promoting wound healing, comprising administering to a patient having a wound an effective amount of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, 5-(3-chlorophenyl)-3-hydroxypyridine-2-carbonyl]amino}acetic acid or 2-(5-(3-fluorophenyl)-3-hydroxypicolinamido)acetic acid) according to the dose and/or dosing regimen described herein. In certain such embodiments, the daily dose is about 150 mg, about 300 mg, about 450 mg, about 600 mg, or about 750 mg of {[5-(3-chlorophenyl)-3-hydroxypyridine-2-carbonyl]amino}acetic acid. In certain such embodiments, the daily dose is about 150 rag, about 300 mg, about 450 mg, about 600 mg, or about 750 mg of 2-(5-(3-fluorophenyl)-3-hydroxypicolinamido)acetic acid. In certain such embodiments, the daily dose is about 150 mg, about 300 mg, about 450 mg, or about 600 mg. Such daily doses may be administered orally, once daily, twice daily, or three times daily, preferably once daily.

In certain embodiments, provided herein are methods of enhancing the revascularization of damaged tissue or increasing vasculature, comprising administering to a patient having damaged tissue an effective amount of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, 5-(3-chlorophenyl)-3-hydroxypyridine-2-carbonyl]amino}acetic acid or 2-(5-(3-fluorophenyl)-3-hydroxypicolinamido)acetic acid) according to the dose and/or dosing regimen described herein. In certain embodiments, provided herein are methods of vascularizing ischemic tissue, comprising administering to a patient having ischemic tissue an effective amount of 5-(3-chlorophenyl)-3-hydroxypyridine-2-carbonyl]amino}acetic acid according to the dose and/or dosing regimen described herein. In certain embodiments, provided herein are methods of vascularizing ischemic tissue, comprising administering to a patient having ischemic tissue an effective amount of 2-(5-(3-fluorophenyl)-3-hydroxypicolinamido)acetic acid according to the dose and/or dosing regimen described herein. In certain such embodiments, the daily dose is about 150 mg, about 300 mg, about 450 mg, about 600 mg, or about 750 mg of {[5-(3-chlorophenyl)-3-hydroxypyridine-2-carbonyl]amino}acetic acid. In certain such embodiments, the daily dose is about 150 mg, about 300 mg, about 450 mg, about 600 mg, or about 750 mg of 2-(5-(3-fluorophenyl)-3-hydroxypicolinamido)acetic acid. In certain such embodiments, the daily dose is about 150 mg, about 300 mg, about 450 mg, or about 600 mg. Such daily doses may be administered orally, once daily, twice daily, or three times daily, preferably once daily.

In certain embodiments, provided herein are methods of promoting the growth of skin graft replacements, comprising administering to a patient having a skin graft an effective amount of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, 5-(3-chlorophenyl)-3-hydroxypyridine-2-carbonyl]amino}acetic acid or 2-(5-(3-fluorophenyl)-3-hydroxypicolinamido)acetic acid) according to the dose and/or dosing regimen described herein. In certain such embodiments, the daily dose is about 150 mg, about 300 mg, about 450 mg, about 600 mg, or about 750 mg of {[5-(3-chlorophenyl)-3-hydroxypyridine-2-carbonyl]amino}acetic acid. In certain such embodiments, the daily dose is about 150 mg, about 300 mg, about 450 mg, about 600 mg, or about 750 mg of 2-(5-(3-fluorophenyl)-3-hydroxypicolinamido)acetic acid. In certain such embodiments, the daily dose is about 150 mg, about 300 mg, about 450 mg, or about 600 mg. Such daily doses may be administered orally, once daily, twice daily, or three times daily, preferably once daily.

In certain embodiments, provided herein are methods of promoting tissue repair in the context of guided tissue regeneration (GTR), comprising administering to a patient an effective amount of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, 5-(3-chlorophenyl)-3-hydroxypyridine-2-carbonyl] amino}acetic acid or 2-(5-(3-fluorophenyl)-3-hydroxypicolinamido)acetic acid) according to the dose and/or dosing regimen described herein. In certain such embodiments, the daily dose is about 150 mg, about 300 mg, about 450 mg, about 600 mg, or about 750 mg of {[5-(3-chlorophenyl)-3-hydroxypyridine-2-carbonyl]amino}acetic acid. In certain such embodiments, the daily dose is about 150 mg, about 300 mg, about 450 mg, about 600 mg, or about 750 mg of 2-(5-(3-fluorophenyl)-3-hydroxypicolinamido)acetic acid. In certain such embodiments, the daily dose is about 150 mg, about 300 mg, about 450 mg, or about 600 mg. Such daily doses may be administered orally, once daily, twice daily, or three times daily, preferably once daily.

In certain embodiments, provided herein are methods of treating or preventing a disease or disorder selected from diabetic retinopathy, macular degeneration, cancer, sickle cell anemia, sarcoid, syphilis, pseudoxanthoma elasticum, Paget's disease, vein occlusion, artery occlusion, carotid obstructive disease, chronic uveitis/vitritis, mycobacterial infections. Lyme's disease, systemic lupus erythematosis, retinopathy of prematurity, Eales' disease, Behcet's disease, infections causing a retinitis or choroiditis, presumed ocular histoplasmosis, Best's disease, myopia, optic pits, Stargardt's disease, pars planitis, chronic retinal detachment, hyperviscosity syndrome, toxoplasmosis, trauma post-laser complications, diseases associated with rubeosis, and proliferative vitreoretinopathy, Crohn's disease and ulcerative colitis, psoriasis, sarcoidosis, rheumatoid arthritis, hemangiomas, Osler-Weber-Rendu disease, or hereditary hemorrhagic telangiectasia, solid or blood borne tumors, acquired immune deficiency syndrome, skeletal muscle and myocardial ischemia, stroke, coronary artery disease, peripheral vascular disease, and coronary artery disease, comprising administering to a patient having such a disease or disorder an effective amount of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, 5-(3-chlorophenyl)-3-hydroxypyridine-2-carbonyl] amino}acetic acid or 2-(5-(3-fluorophenyl)-3-hydroxypicolinamido)acetic acid) according to the dosages and/or dose and/or dosing regimens described herein. In certain such embodiments, the daily dose is about 150 mg, about 300 mg, about 450 mg, about 600 mg, or about 750 mg of {[5-(3-chlorophenyl)-3-hydroxypyridine-2-carbonyl] amino}acetic acid. In certain such embodiments, the daily dose is about 150 mg, about 300 mg, about 450 mg, about 600 mg, or about 750 mg of 2-(5-(3-fluorophenyl)-3-hydroxypicolinamido)acetic acid. In certain such embodiments, the daily dose is about 150 mg, about 300 mg, about 450 mg, or about 600 mg. Such daily doses may be administered orally, once daily, twice daily, or three times daily, preferably once daily.

5.5 Doses and Dosing Regimens

Various parameters are described herein to guide the dosing regimen of a HIF prolyl hydroxylase inhibitor or a HIF-alpha stabilizer for the prevention and/or treatment of various diseases and disorders as described in Section 5.4, such as anemia (e.g., anemia secondary to chronic kidney disease). This section provides several specific doses for such uses of a HIF prolyl hydroxylase inhibitor or a HIF-alpha stabilizer. In certain embodiments, such a dose is the initial dose at the beginning of a treatment. In other embodiments, such a dose is the adjusted dose at a later time during the course of treatment. In certain embodiments, the HIF prolyl hydroxylase inhibitor or a HIF-alpha stabilizer is a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof. In a specific embodiment, the compound is Compound 1 or a pharmaceutically acceptable salt, solvate, or hydrate thereof. In a specific embodiment, the compound is Compound 7 or a pharmaceutically acceptable salt, solvate, or hydrate thereof.

In certain embodiments, provided herein are methods for treating anemia, such as anemia secondary to chronic kidney disease, comprising administering to a patient having anemia, a daily dose of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, {[5-(3-chlorophenyl)-3-hydroxypyridine-2-carbonyl]amino}acetic acid or 2-(5-(3-fluorophenyl)-3-hydroxypicolinamido)acetic acid) which is between about 100 mg and about 1,200 mg, about 200 mg and about 1,000 mg, about 400 mg and about 800 mg, or about 450 mg and about 600 mg, or about 300 mg and about 600 mg. In certain embodiments, the daily dose of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, {[5-(3-chlorophenyl)-3-hydroxypyridine-2-carbonyl]amino}acetic acid or 2-(5-(3-fluorophenyl)-3-hydroxypicolinamido)acetic acid) is between about 150 mg and about 600 mg. In certain embodiments, the daily dose of the compound is between about 150 mg and about 300 mg, about 300 and about 600 mg, or between about 600 mg and about 750 mg. In certain embodiments, the daily dose is about 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, 1,000 mg, 1,050 mg, 1,100 mg, 1,150 mg, or even about 1,200 mg of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, {[5-(3-chlorophenyl)-3-hydroxypyridine-2-carbonyl]amino}acetic acid or 2-(5-(3-fluorophenyl)-3-hydroxypicolinamido)acetic acid). In certain embodiments, the daily dose is at least about 300 mg, at least about 450 mg, or even at least about 600 mg.

In certain embodiments, the daily dose is about 150 mg, about 300 mg, about 450 mg, about 600 mg, or about 750 mg of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, {[5-(3-chlorophenyl)-3-hydroxypyridine-2-carbonyl]amino}acetic acid or 2-(5-(3-fluorophenyl)-3-hydroxypicolinamido)acetic acid). In certain embodiments, the daily dose is about 150 mg, about 300 mg, about 450 mg, or about 600 mg. In certain embodiments, the daily dose is not 240 mg, 370 mg, 500 mg or 630 mg of Compound 1. In certain embodiments, the daily dose is about 240 mg, 370 mg, 500 mg or about 630 mg of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, {[5-(3-chlorophenyl)-3-hydroxypyridine-2-carbonyl]amino}acetic acid or 2-(5-(3-fluorophenyl)-3-hydroxypicolinamido)acetic acid).

In certain embodiments, provided herein are methods for treating anemia, such as anemia secondary to chronic kidney disease, comprising administering to a patient having anemia daily dose of a compound which is a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, {[5-(3-chlorophenyl)-3-hydroxypyridine-2-carbonyl]amino}acetic acid or 2-(5-(3-fluorophenyl)-3-hydroxypicolinamido)acetic acid), wherein the compound is administered continuously and/or indefinitely.

In certain embodiments, provided herein are methods for treating anemia, such as anemia secondary to chronic kidney disease, comprising administering to a patient having anemia a daily dose of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, {[5-(3-chlorophenyl)-3-hydroxypyridine-2-carbonyl]amino}acetic acid or 2-(5-(3-fluorophenyl)-3-hydroxypicolinamido)acetic acid), wherein the daily dose is about 450 mg. In certain such embodiments, a daily dose of about 450 mg comprises three unit dosage forms, such as three tablets, each comprising about 150 mg of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, {[5-(3-chlorophenyl)-3-hydroxypyridine-2-carbonyl]amino}acetic acid or 2-(5-(3-fluorophenyl)-3-hydroxypicolinamido)acetic acid). In certain embodiments, a daily dose of about 450 mg of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, {[5-(3-chlorophenyl)-3-hydroxypyridine-2-carbonyl]amino}acetic acid or 2-(5-(3-fluorophenyl)-3-hydroxypicolinamido)acetic acid) may be increased by about 150 mg such that the daily dose of the compound is about 600 mg. In certain embodiments, a daily dose of 450 mg of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, {[5-(3-chlorophenyl)-3-hydroxypyridine-2-carbonyl]amino}acetic acid or 2-(5-(3-fluorophenyl)-3-hydroxypicolinamido)acetic acid) may be decreased by about 150 mg, such that the daily dose of the compound is about 300 mg. In certain embodiments, a daily dose of a compound having a structure of Formula (I), Formula (II), Formula (I), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, {[5-(3-chlorophenyl)-3-hydroxypyridine-2-carbonyl]amino}acetic acid or 2-(5-(3-fluorophenyl)-3-hydroxypicolinamido)acetic acid) may be decreased by about 300 mg, such that the daily dose of the compound is about 150 mg. In certain embodiments, the daily dose may be increased or decreased by about 75 mg, about 100 mg, about 125 mg, about 150 mg, about 175 mg, about 200 mg, about 225 mg, about 250 mg, about 275 mg, or about 300 mg. In certain embodiments, the daily dose may be increased or decreased by an amount between about 75 mg and 300 mg, about 100 mg and about 300 mg, about 125 mg and about 300 mg, about 150 mg and about 300 mg, about 175 mg and about 300 mg, about 200 mg and about 300 mg, about 225 mg and about 300 mg, about 250 mg and about 300 mg, or about 275 mg and about 300 mg. In certain embodiments, the daily dose may be increased or decreased by an amount between about 75 mg and about 250 mg, about 100 mg and about 225 mg, or about 125 mg and about 200 mg. In certain such embodiments, the daily dose does not exceed about 600 mg or about 750 mg.

In certain embodiments, provided herein are methods for treating anemia, such as anemia secondary to chronic kidney disease, comprising administering to a patient having anemia an effective amount of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, {[5-(3-chlorophenyl)-3-hydroxypyridine-2-carbonyl]amino}acetic acid or 2-(5-(3-fluorophenyl)-3-hydroxypicolinamido)acetic acid), wherein the compound may be administered continuously and/or indefinitely, such as for more than 42 consecutive days. In certain such embodiments, a daily dose of the compound is about 150 mg, about 300 mg, about 450 mg, about 600 mg, or about 750 mg of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, {[5-(3-chlorophenyl)-3-hydroxypyridine-2-carbonyl]amino}acetic acid or 2-(5-(3-fluorophenyl)-3-hydroxypicolinamido)acetic acid). In certain such embodiments, the daily dose is about 150 mg, about 300 mg, about 450 mg, or about 600 mg.

In certain embodiments, provided herein are methods for treating anemia, such as anemia secondary to chronic kidney disease, comprising administering to a patient having anemia an effective amount of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, {[5-(3-chlorophenyl)-3-hydroxypyridine-2-carbonyl] amino}acetic acid or 2-(5-(3-fluorophenyl)-3-hydroxypicolinamido)acetic acid), wherein hemoglobin levels of a patient are maintained at a level of at least about 10.0 g/dL and at or below about 13.0 g/dL. In certain such embodiments, the hemoglobin levels are maintained at a level of at least about 11.0 g/dL and at or below about 13.0 g/dL. In certain such embodiments, the hemoglobin levels are maintained at a level of at least about 11.0 g/dL and at or below about 12.0 g/dL. In certain such embodiments, a daily dose of the compound is about 150 mg, about 300 mg, about 450 mg, about 600 mg, or about 750 mg of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, {[5-(3-chlorophenyl)-3-hydroxypyridine-2-carbonyl]amino}acetic acid or 2-(5-(3-fluorophenyl)-3-hydroxypicolinamido)acetic acid). In certain such embodiments, the daily dose is about 150 mg, about 300 mg, about 450 mg, or about 600 mg.

In certain embodiments, provided herein are methods for treating anemia, such as anemia secondary to chronic kidney disease, comprising administering to a patient having anemia an effective amount of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11 Compound 12, Compound 13, Metabolite 1, or Metabolite 2 or a pharmaceutically acceptable salt, solvate, or hydrate thereof (specifically, {[5-(3-chlorophenyl)-3-hydroxypyridine-2-carbonyl]amino}acetic acid or 2-(5-(3-fluorophenyl)-3-hydroxypicolinamido)acetic acid), wherein level of hemoglobin of a patient are increased at least about 1.2 g/dL relative to a baseline hemoglobin level. In certain such embodiments, a daily dose of the compound is about 150 mg, about 300 mg, about 450 mg, about 600 mg, or about 750 mg of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, {[5-(3-chlorophenyl)-3-hydroxypyridine-2-carbonyl]amino}acetic acid or 2-(5-(3-fluorophenyl)-3-hydroxypicolinamido)acetic acid). In certain such embodiments, the daily dose is about 150 mg, about 300 mg, about 450 mg, or about 600 mg.

In certain embodiments, administration of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, {[5-(3-chlorophenyl)-3-hydroxypyridine-2-carbonyl]amino}acetic acid or 2-(5-(3-fluorophenyl)-3-hydroxypicolinamido)acetic acid) may be suspended if the level of hemoglobin is at or above 13.0 g/dL. In certain such embodiments, administration of the compound may be resumed once the level of hemoglobin is at or below 12.5 g/dL.

In certain embodiments, hemoglobin levels are monitored and the dose of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, {[5-(3-chlorophenyl)-3-hydroxypyridine-2-carbonyl]amino}acetic acid or 2-(5-(3-fluorphenyl)-3-hydroxypicolinamido)acetic acid) may be adjusted based on the level of hemoglobin and/or the change in level of hemoglobin. In certain embodiments, the dose may be adjusted by either increasing or reducing the amount of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, {[5-(3-chlorophenyl)-3-hydroxypyridine-2-carbonyl]amino}acetic acid or 2-(5-(3-fluorophenyl)-3-hydroxypicolinamido)acetic acid) by 150 mg or even by 300 mg.

In certain embodiments, the daily dose of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, {[5-(3-chlorophenyl)-3-hydroxypyridine-2-carbonyl]amino}acetic acid or 2-(5-(3-fluorophenyl)-3-hydroxypicolinamido)acetic acid) may be increased after a period of time, beginning on the day a patient is given a daily dose of the compound. In certain embodiments, the period of time is from about one week to about eight weeks, such as from about two weeks to about seven weeks, about three weeks to about six weeks, or about four weeks.

In certain embodiments, the daily dose of a compound having a structure of Formula (I), Formula (II), Formula (I), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, {[5-(3-chlorophenyl)-3-hydroxypyridine-2-carbonyl]amino}acetic acid or 2-(5-(3-fluorophenyl)-3-hydroxypicolinamido)acetic acid) may be adjusted once in a period of time. In certain embodiments, the period of time is from about one week to about eight weeks, such as from about two weeks to about seven weeks, about three weeks to about six weeks, or about four weeks In certain embodiments, the daily dose of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, {[5-(3-chlorophenyl)-3-hydroxypyridine-2-carbonyl]amino}acetic acid or 2-(5-(3-fluorophenyl)-3-hydroxypicolinamido)acetic acid) is not increased if the level of hemoglobin has increased by more than 1.2 g/dL relative to a baseline hemoglobin level.

In certain embodiments, provided herein are methods for treating anemia, such as anemia secondary to chronic kidney disease, comprising administering to a patient having anemia a daily dose of a compound which is a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, {[5-(3-chlorophenyl)-3-hydroxypyridine-2-carbonyl]amino}acetic acid or 2-(5-(3-fluorophenyl)-3-hydroxypicolinamido)acetic acid); measuring the hemoglobin level in the patient after an administration of the daily dose of the compound and then again a period of time later, wherein when the hemoglobin level in the patient is less than about 10.0 g/dL and the level of hemoglobin has decreased by less than about 0.5 g/dL as compared to the level measured the period of time earlier; or when the hemoglobin level in the patient is less than about 10.0 g/dL and the level of hemoglobin has changed by up to about 0.4 g/dL as compared to the level measured the period of time earlier; or when the hemoglobin level in the patient is between about 10.0 and about 10.9 g/dL and the level of hemoglobin has decreased by less than about 0.5 g/dL as compared to the level measured the period of time earlier; administering an adjusted daily dose of the compound that is about 150 mg greater than the daily dose. In certain such embodiments, the compound is administered once daily and may be administered orally. In certain embodiments, the daily dose is about 450 mg, such that when the daily dose is increased by about 150 mg, the adjusted daily dose is about 600 mg. In certain embodiments, the period of time is from about one week to about eight weeks, such as from about two weeks to about seven weeks, about three weeks to about six weeks, or about four weeks. In certain embodiments, the daily dose may be increased or decreased by about 75 mg, about 100 mg, about 125 mg, about 150 mg, about 175 mg, about 200 mg, about 225 mg, about 250 mg, about 275 mg, or about 300 mg. In certain embodiments, the daily dose may be increased or decreased by an amount between about 75 mg and 300 mg, about 100 mg and about 300 mg, about 125 mg and about 300 mg, about 150 mg and about 300 mg, about 175 mg and about 300 mg, about 200 mg and about 300 mg, about 225 mg and about 300 mg, about 250 mg and about 300 mg, or about 275 mg and about 300 mg. In certain embodiments, the daily dose may be increased or decreased by an amount between about 75 mg and about 250 mg, about 100 mg and about 225 mg, or about 125 mg and about 200 mg. In certain embodiments, the adjusted daily dose does not exceed 600 mg or 750 mg.

In certain embodiments, provided herein are methods for treating anemia, such as anemia secondary to chronic kidney disease, comprising administering to a patient having anemia a daily dose of a compound which is a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, {[5-(3-chlorophenyl)-3-hydroxypyridine-2-carbonyl]amino}acetic acid); measuring the hemoglobin level in the patient after an administration of the daily dose of the compound and then again a period of time later, wherein when the hemoglobin level in the patient is less than about 10.0 g/dL and the level of hemoglobin has increased by greater than about 1.5 g/dL as compared to the level measured the period of time earlier; or when the hemoglobin level in the patient is between about 10.0 and about 10.9 g/dL and the level of hemoglobin has increased by greater than about 1.5 g/dL as compared to the level measured the period of time earlier; or when the hemoglobin level in the patient is between about 11.0 and about 12.2 g/dL and the level of hemoglobin has increased by between about 1.0 and about 1.4 g/dL as compared to the level measured the period of time earlier, or when the hemoglobin level in the patient is between about 12.3 and about 12.9 g/dL and the level of hemoglobin has decreased by up to about 0.4 g/dL or increased by up to about 0.4 g/dL as compared to the level measured the period of time earlier; or when the hemoglobin level in the patient is between about 12.3 and about 12.9 g/dL and the level of hemoglobin has increased by about 0.5 to about 0.9 g/dL as compared to the level measured the period of time earlier administering an adjusted daily dose of the compound that is 150 mg less than the daily dose. In certain such embodiments, the compound is administered once daily and may be administered orally. In certain embodiments, the daily dose is about 450 mg, such that when the daily dose is decreased by about 150 mg, the adjusted daily dose is about 300 mg. In certain embodiments, the period of time is from about one week to about eight weeks, such as from about two weeks to about seven weeks, about three weeks to about six weeks, or about four weeks. In certain embodiments, the daily dose may be increased or decreased by about 75 mg, about 100 mg, about 125 mg, about 150 mg, about 175 mg, about 200 mg, about 225 mg, about 250 mg, about 275 mg, or about 300 mg. In certain embodiments, the daily dose may be increased or decreased by an amount between about 75 mg and 300 mg, about 100 mg and about 300 mg, about 125 mg and about 300 mg, about 150 mg and about 300 mg, about 175 mg and about 300 mg, about 200 mg and about 300 mg, about 225 mg and about 300 mg, about 250 mg and about 300 mg, or about 275 mg and about 300 mg. In certain embodiments, the daily dose may be increased or decreased by an amount between about 75 mg and about 250 mg, about 100 mg and about 225 mg, or about 125 mg and about 200 mg. In certain embodiments, the adjusted daily dose does not exceed 600 mg or 750 mg.

In certain embodiments, provided herein are methods of treating anemia, such as anemia secondary to chronic kidney disease, comprising administering to a patient having anemia a daily dose of a compound which is a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, {[5-(3-chlorophenyl)-3-hydroxypyridine-2-carbonyl]amino}acetic acid or 2-(5-(3-fluorophenyl)-3-hydroxypicolinamido)acetic acid); measuring the hemoglobin level in the patient after an administration of the daily dose of the compound and then again a period of time later, wherein when the hemoglobin level in the patient is between about 11.0 and about 12.2 g/dL and the level of hemoglobin has increased by greater than about 1.5 g/dL as compared to the level measured the period of time earlier, or when the hemoglobin level in the patient is between about 12.3 and about 12.9 g/dL and the level of hemoglobin has increased by between about 1.0 and about 1.4 g/dL as compared to the level measured the period of time earlier; or when the hemoglobin level in the patient is between about 12.3 and about 12.9 g/dL and the level of hemoglobin has increased by greater than about 1.5 g/dL as compared to the level measured the period of time earlier administering an adjusted daily dose of the compound that is about 300 mg less than the daily dose. In certain embodiments, the compound is administered once daily and may be administered orally. In certain embodiments, the daily dose is 450 mg, such that when the initial daily dose is decreased by about 300 mg, the adjusted daily dose is about 150 mg. In certain embodiments, the period of time is from about one week to about eight weeks, such as from about two weeks to about seven weeks, about three weeks to about six weeks, or about four weeks. In certain embodiments, the daily dose may be increased or decreased by about 75 mg, about 100 mg, about 125 mg, about 150 mg, about 175 mg, about 200 mg, about 225 mg, about 250 mg, about 275 mg, or about 300 mg. In certain embodiments, the daily dose may be increased or decreased by an amount between about 75 mg and 300 mg, about 100 mg and about 300 mg, about 125 mg and about 300 mg, about 150 mg and about 300 mg, about 175 mg and about 300 mg, about 200 mg and about 300 mg, about 225 mg and about 300 mg, about 250 mg and about 300 mg, or about 275 mg and about 300 mg. In certain embodiments, the daily dose may be increased or decreased by an amount between about 75 mg and about 250 mg, about 100 mg and about 225 mg, or about 125 mg and about 200 mg. In certain embodiments, the adjusted daily dose does not exceed 600 mg or 750 mg.

In certain embodiments, provided herein are methods for treating anemia related to CKD in a patient undergoing hemodialysis, wherein said method comprises administering to the patient a pharmaceutically effective amount of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 at about 8 hours, 7 hours, 6 hours, 5 hours, 4 hours, 3 hours, 2 hours, or 1 hour, or at about between 7 hours to 8 hours, 6 hours to 7 hours, 5 hours to 6 hours, 4 hours to 5 hours, 3 hours to 4 hours, 2 hours to 3 hours, 1 hour to 2 hours, or up to about 1 hour prior to starting a hemodialysis session.

In certain embodiments, provided herein are methods for treating anemia related to CKD in a patient undergoing hemodialysis, wherein said method comprises administering to the patient a pharmaceutically effective amount of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 at about 8 hours, 7 hours, 6 hours, 5 hours, 4 hours, 3 hours, 2 hours, or 1 hour, or at about between 7 hours to 8 hours, 6 hours to 7 hours, 5 hours to 6 hours, 4 hours to 5 hours, 3 hours to 4 hours, 2 hours to 3 hours, 1 hour to 2 hours, or up to about 1 hour after completing a hemodialysis session.

In certain embodiments, a method provided herein further comprises a monitoring step wherein the serum concentration of a metabolite of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 is determined. In more specific embodiments, the serum concentration of the phenolic-glucuronide and/or the acyl-glucuronide of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 is determined. In even more specific embodiments, the serum concentration of the phenolic-glucuronide and/or the acyl-glucuronide of Compound 1, i.e., Metabolite 1 or Metabolite 2 (see Section 5.2) is determined. In certain even more specific embodiments, the daily dose is adjusted in accordance with the scrum concentration of the metabolite.

5.6 Combination Therapy

In certain embodiments, provided herein are methods for treating anemia, such as anemia secondary to chronic kidney disease, comprising administering a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, {[5-(3-chlorophenyl)-3-hydroxypyridine-2-carbonyl]amino}acetic acid or 2-(5-(3-fluorophenyl)-3-hydroxypicolinamido)acetic acid) in combination with another medicament. Such combination therapy may be achieved by way of the simultaneous, sequential, or separate dosing of the individual components of the treatment. Additionally, when administered as a component of such combination therapy, the compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, {[5-(3-chlorophenyl)-3-hydroxypyridine-2-carbonyl]amino}acetic acid or 2-(5-(3-fluorphenyl)-3-hydroxypicolinamido)acetic acid) and the other medicament may be synergistic, such that the daily dose of either or both of the components may be reduced as compared to the dose of either component that would normally be given as a monotherapy. Alternatively, when administered as a component of such combination therapy, the compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, {[5-(3-chlorophenyl)-3-hydroxypyridine-2-carbonyl]amino}acetic acid or 2-(5-(3-fluorophenyl)-3-hydroxypicolinamido)acetic acid) and the other medicament may be additive, such that the daily dose of each of the components is similar or the same as the dose of either component that would normally be given as a monotherapy.

In certain embodiments, provided herein are methods for treating non-severe anemia secondary to chronic kidney disease, non-severe anemia secondary to congestive heart failure, and idiopathic anemia of aging, comprising administering to a patient having anemia daily dose a HIF prolyl hydroxylase inhibitor or a HIF-alpha stabilizer, such as a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, compound disclosed herein, such as Compound 1), wherein the compound is administered continuously and/or indefinitely, and wherein the compound is administered with another medicament.

In certain embodiments, provided herein are methods for treating anemia, such as anemia secondary to chronic kidney disease, comprising administering a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, {[5-(3-chlorophenyl)-3-hydroxypyridine-2-carbonyl]amino}acetic acid or 2-(5-(3-fluorophenyl)-3-hydroxypicolinamido)acetic acid) to a patient having anemia, wherein the compound is optionally administered in combination with an iron supplement, such as ferrous sulfate, ferrous gluconate, or ferrous fumarate. In certain such embodiments, the iron supplement is administered at least one hour, at least two hours, at least three hours, at least four hours, or even at least six hours following administration of the compound. In certain embodiments, the iron supplement is administered in an amount such that ferritin is maintained at a level of between about 50 ng/mL and about 300 ng/mL. In certain embodiments, the iron supplement is administered orally at a daily dose of at least about 50 mg of elemental iron. In certain embodiments, the iron supplement is administered orally at a dose of about 50 mg of elemental iron. In certain embodiments, the iron supplement is administered intravenously. In certain embodiments, the iron supplement is administered continuously and/or indefinitely, such as for more than 42 consecutive days. In certain alternative embodiments, the iron supplement is administered on an as needed basis such that ferritin is maintained at a level of between about 50 ng/mL and about 300 ng/mL. In certain such embodiments, the daily dose of the compound is about 150 mg, about 300 mg, about 450 mg, about 600 mg, or about 750 mg of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, {[5-(3-chlorophenyl)-3-hydroxypyridine-2-carbonyl]amino}acetic acid or 2-(5-(3-fluorophenyl)-3-hydroxypicolinamido)acetic acid). In certain such embodiments, the daily dose is about 150 mg, about 300 mg, about 450 mg, or about 600 mg. Such daily doses may be administered orally, once daily, twice daily, or three times daily, preferably once daily.

In certain embodiments, provided herein are methods for treating anemia, such as anemia secondary to chronic kidney disease, comprising administering a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, {[5-(3-chlorophenyl)-3-hydroxypyridine-2-carbonyl]amino}acetic acid or 2-(5-(3-fluorophenyl)-3-hydroxypicolinamido)acetic acid) to a patient having anemia, wherein the compound is optionally administered in combination with an erythropoiesis stimulating agent (ESA), such as an erythropoietin mimetic. In certain such embodiments, the ESA is an rhEPO product, including, but not limited to, epoetin alfa, epoetin beta, darbepoetin, or peginesatide. In certain such embodiments, the ESA is administered as a rescue therapy. In certain alternative embodiments, the ESA is administered continuously and/or indefinitely, such as for more than 42 consecutive days. In certain such embodiments, the daily dose is of the compound is about 150 mg, about 300 mg, about 450 mg, about 600 mg, or about 750 mg of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, {[5-(3-chlorophenyl)-3-hydroxypyridine-2-carbonyl]amino}acetic acid or 2-(5-(3-fluorophenyl)-3-hydroxypicolinamido)acetic acid). In certain such embodiments, the daily dose is about 150 mg, about 300 mg, about 450 mg, or about 600 mg. Such daily doses may be administered orally, once daily, twice daily, or three times daily, preferably once daily.

5.7 Patient Populations

In certain embodiments, provided herein are methods for treating anemia, such as anemia secondary to chronic kidney disease (CKD), comprising administering to a patient having anemia an effective amount of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, 5-(3-chlorophenyl)-3-hydroxypyridine-2-carbonyl]amino}acetic acid or 2-(5-(3-fluorophenyl)-3-hydroxypicolinamido)acetic acid) according to the dose and/or dosing regimen described herein, wherein, the patient is at least 50 years old, at least 60 years old, at least 65 years old, at least 70 years old, or even at least 80 years old. In certain embodiments, the patient is a geriatric patient. In certain embodiments, the patient is less than 18 years old. In certain embodiments, the patient is a pediatric patient. In certain embodiment, the patient is at least 18 years old. In certain such embodiments, the daily dose is about 150 mg, about 300 mg, about 450 mg, about 600 mg, or about 750 mg of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, {[5-(3-chlorophenyl)-3-hydroxypyridine-2-carbonyl]amino}acetic acid or 2-(5-(3-fluorophenyl)-3-hydroxypicolinamido)acetic acid). In certain such embodiments, the daily dose is about 150 mg, about 300 mg, about 450 mg, or about 600 mg. Such daily doses may be administered orally, once daily, twice daily, or three times daily, preferably once daily.

In certain embodiments, provided herein are methods for treating anemia, such as anemia secondary to chronic kidney disease (CKD), comprising administering to a patient having anemia an effective amount of a compound having a structure of Formula (I), Formula (II), Formula (II), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, 5-(3-chlorophenyl)-3-hydroxypyridine-2-carbonyl]amino}acetic acid or 2-(5-(3-fluorophenyl)-3-hydroxypicolinamido)acetic acid) according to the dose and/or dosing regimen described herein, wherein, the patient is a member of a subpopulation selected from White, Hispanic, Black, and Asian. In certain embodiments, the patient is a member of a subpopulation selected from male and female. In certain such embodiments, the daily dose is about 150 mg, about 300 mg, about 450 mg, about 600 mg, or about 750 mg of a compound having a structure of Formula (I), Formula (I), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, {[5-(3-chlorophenyl)-3-hydroxypyridine-2-carbonyl]amino}acetic acid or 2-(5-(3-fluorophenyl)-3-hydroxypicolinamido)acetic acid). In certain such embodiments, the daily dose is about 150 mg, about 300 mg, about 450 mg, or about 600 mg. Such daily doses may be administered orally, once daily, twice daily, or three times daily, preferably once daily.

In certain embodiments, provided herein are methods for treating anemia, such as anemia secondary to chronic kidney disease (CKD), comprising administering to a patient having anemia an effective amount of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, 5-(3-chlorophenyl)-3-hydroxypyridine-2-carbonyl]amino}acetic acid or 2-(5-(3-fluorophenyl)-3-hydroxypicolinamido)acetic acid) according to the dose and/or dosing regimen described herein, wherein the patient has an additional disease or condition selected from cancer, AIDS, congestive heart failure, left ventricular hypertrophy, diabetes, hypertension, dyslipidemia, chronic heart failure, stroke, fatigue, depression, and cognitive impairment, or any combination thereof. In certain such embodiments, the daily dose is about 150 mg, about 300 mg, about 450 mg, about 600 mg, or about 750 mg of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, {[5-(3-chlorophenyl)-3-hydroxypyridine-2-carbonyl]amino}acetic acid or 2-(5-(3-fluorophenyl)-3-hydroxypicolinamido)acetic acid). In certain such embodiments, the daily dose is about 150 ng, about 300 mg, about 450 mg, or about 600 mg. Such daily doses may be administered orally, once daily, twice daily, or three times daily, preferably once daily.

In certain embodiments, provided herein are methods for treating anemia, such as anemia secondary to CKD, comprising administering to a patient having anemia an effective amount of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, 5-(3-chlorophenyl)-3-hydroxypyridine-2-carbonyl]amino}acetic acid or 2-(5-(3-fluorophenyl)-3-hydroxypicolinamido)acetic acid) according to the dose and/or dosing regimen described herein, wherein the patient is refractory to treatment with an ESA, such as an erythropoietin mimetic. In certain embodiments the ESA is an rhEPO product, including, but not limited to, epoetin alfa, epoetin beta, darbepoetin, or peginesatide. In certain such embodiments, the daily dose is about 150 mg, about 300 mg, about 450 mg, about 600 mg, or about 750 mg of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, {[5-(3-chlorophenyl)-3-hydroxypyridine-2-carbonyl] amino}acetic acid or 2-(5-(3-fluorophenyl)-3-hydroxypicolinamido)acetic acid). In certain such embodiments, the daily dose is about 150 mg, about 300 mg, about 450 mg, or about 600 mg. Such daily doses may be administered orally, once daily, twice daily, or three times daily, preferably once daily.

In certain embodiments, provided herein are methods for treating anemia, such as anemia secondary to CKD, comprising administering to a patient having anemia an effective amount of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, 5-(3-chlorophenyl)-3-hydroxypyridine-2-carbonyl]amino}acetic acid or 2-(5-(3-fluorophenyl)-3-hydroxypicolinamido)acetic acid) according to the dose and/or dosing regimen described herein, wherein the patient has a transferrin saturation (TSAT) of at least 15%, at least 18% or even at least 20%. In certain such embodiments, the daily dose is about 150 mg, about 300 mg, about 450 mg, about 600 mg, or about 750 mg of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, {[5-(3-chlorophenyl)-3-hydroxypyridine-2-carbonyl]amino}acetic acid or 2-(5-(3-fluorophenyl)-3-hydroxypicolinamido)acetic acid). In certain such embodiments, the daily dose is about 150 mg, about 300 mg, about 450 mg, or about 600 mg. Such daily doses may be administered orally, once daily, twice daily, or three times daily, preferably once daily.

In certain embodiments, provided herein are methods for treating anemia, such as anemia secondary to CKD, comprising administering to a patient having anemia an effective amount of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, 5-(3-chlorophenyl)-3-hydroxypyridine-2-carbonyl]amino}acetic acid or 2-(5-(3-fluorophenyl)-3-hydroxypicolinamido)acetic acid) according to the dose and/or dosing regimen described herein, wherein the patient has a ferritin level of at least 50 ng/mL or even at least 100 ng/mL. In certain such embodiments, the daily dose is about 150 mg, about 300 mg, about 450 mg, about 600 mg, or about 750 mg of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, {[5-(3-chlorophenyl)-3-hydroxypyridine-2-carbonyl]amino}acetic acid or 2-(5-(3-fluorophenyl)-3-hydroxypicolinamido)acetic acid). In certain such embodiments, the daily dose is about 150 mg, about 300 mg, about 450 mg, or about 600 mg. Such daily doses may be administered orally, once daily, twice daily, or three times daily, preferably once daily.

In certain embodiments, provided herein are methods for treating anemia, such as anemia secondary to CKD, comprising administering to a patient having anemia an effective amount of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, 5-(3-chlorophenyl)-3-hydroxypyridine-2-carbonyl]amino}acetic acid or 2-(5-(3-fluorophenyl)-3-hydroxypicolinamido)acetic acid) according to the dose and/or dosing regimen described herein, wherein the patient has a ferritin level of at least 50 ng/mL with transferrin saturation of at least 18%, or a ferritin level of at least 100 ng/mL with a transferrin saturation of at least 15%. In certain such embodiments, the daily dose is about 150 mg, about 300 mg, about 450 mg, about 600 mg, or about 750 mg of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, {[5-(3-chlorophenyl)-3-hydroxypyridine-2-carbonyl]amino}acetic acid or 2-(5-(3-fluorophenyl)-3-hydroxypicolinamido)acectic acid). In certain such embodiments, the daily dose is about 150 mg, about 300 mg, about 450 mg, or about 600 mg. Such daily doses may be administered orally, once daily, twice daily, or three times daily, preferably once daily.

In certain embodiments, provided herein are methods for treating anemia, such as anemia secondary to CKD, comprising administering to a patient having anemia an effective amount of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, 5-(3-chlorophenyl)-3-hydroxypyridine-2-carbonyl]amino}acetic acid or 2-(5-(3-fluorophenyl)-3-hydroxypicolinamido)acetic acid) according to the dose and/or dosing regimen described herein, wherein the patient has a body mass index (BMI) of less than 42 or less than 44 k/m$^2$. In certain such embodiments, the daily dose is about 150 mg, about 300 mg, about 450 mg, about 600 mg, or about 750 mg of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, {[5-(3-chlorophenyl)-3-hydroxypyridine-2-carbonyl]amino}acetic acid or 2-(5-(3-fluorophenyl)-3-hydroxypicolinamido)acetic acid). In certain such embodiments, the daily dose is about 150 mg, about 300 mg, about 450 mg, or about 600 mg. Such daily doses may be administered orally, once daily, twice daily, or three times daily, preferably once daily.

In certain embodiments, provided herein are methods for treating anemia, such as anemia secondary to CKD, comprising administering to a patient having anemia an effective amount of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, 5-(3-chlorophenyl)-3-hydroxypyridine-2-carbonyl]amino}acetic acid or 2-(5-(3-fluorophenyl)-3-hydroxypicolinamido)acetic acid) according to the dose and/or dosing regimen described herein, wherein the patient has had a red blood cell transfusion within 11 weeks or 12 weeks of initiation of treatment with the compound. In certain alternative embodiments, the patient has not had a red blood cell transfusion within 11 weeks or 12 weeks of initiation of treatment with the compound. In certain such embodiments, the daily dose is about 150 mg, about 300 mg, about 450 mg, about 600 mg, or about 750 mg of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, {[5-(3-chlorophenyl)-3-hydroxypyridine-2-carbonyl] amino}acetic acid or 2-(5-(3-fluorophenyl)-3-hydroxypicolinamido)acetic acid). In certain embodiments, the daily dose is about 150 mg, about 300 mg, about 450 mg, or about 600 mg. Such daily doses may be administered orally, once daily, twice daily, or three times daily, preferably once daily.

In certain embodiments, provided herein are methods for treating non-severe anemia secondary to chronic kidney disease, non-severe anemia secondary to congestive heart failure, and idiopathic anemia of aging, comprising administering to a patient having anemia daily dose a compound disclosed herein, such as Compound 1, wherein the compound is administered continuously and/or indefinitely.

In certain embodiments, provided herein are methods for treating and/or preventing iron overload in a patient, said method comprising administering to the patient an effective amount of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, 5-(3-chlorophenyl)-3-hydroxypyridine-2-carbonyl]amino}acetic acid or 2-(5-(3-fluorophenyl)-3-hydroxypicolinamido)acetic acid). In

5.8 Pharmaceutical Compositions

Pharmaceutical compositions may be used in the preparation of individual, single unit dosage forms. Pharmaceutical compositions and dosage forms provided herein comprise a compound as provided herein, or a pharmaceutically acceptable salt, solvate, or hydrate thereof (e.g., the parent compound). Pharmaceutical compositions and dosage forms can further comprise one or more excipients.

In certain embodiments, pharmaceutical compositions and dosage forms comprise one or more excipients. Suitable excipients are well known to those skilled in the art of pharmacy, and non-limiting examples of suitable excipients are provided herein. Whether a particular excipient is suitable for incorporation into a pharmaceutical composition or dosage form depends on a variety of factors well known in the art including, but not limited to, the way in which the dosage form will be administered to a patient. For example, oral dosage forms such as tablets may contain excipients not suited for use in parenteral dosage forms. The suitability of a particular excipient may also depend on the specific active ingredients in the dosage form. For example, the decomposition of some active ingredients may be accelerated by some excipients such as lactose, or when exposed to water. Active ingredients that comprise primary or secondary amines are particularly susceptible to such accelerated decomposition. Consequently, provided are pharmaceutical compositions and dosage forms that contain little, if any, lactose other mono- or disaccharides. As used herein, the term "lactose-free" means that the amount of lactose present, if any, is insufficient to substantially increase the degradation rate of an active ingredient.

Lactose-free compositions can comprise excipients that are well known in the art and are listed, for example, in the U.S. Pharmacopcia (USP) 25 NF20 (2002). In general, lactose-free compositions comprise active ingredients, a binder/filler, and a lubricant in pharmaceutically compatible and pharmaceutically acceptable amounts. In one embodiment, lactose-free dosage forms comprise active ingredients, microcrystalline cellulose, pre-gelatinized starch, and magnesium stearate.

Also provided are anhydrous pharmaceutical compositions and dosage forms since water can facilitate the degradation of some compounds. For example, the addition of water (e.g., 5%) is widely accepted in the pharmaceutical arts as a means of simulating long-term storage in order to determine characteristics such as shelf-life or the stability of formulations over time. See, e.g., Jens T. Carstensen, Drug Stability: Principles & Practice, 2d. Ed., Marcel Dekker, NY, NY, 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

An anhydrous pharmaceutical composition should be prepared and stored such that its anhydrous nature is maintained. Accordingly, anhydrous compositions are, in one embodiment, packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

Also provided are pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

Like the amounts and types of excipients, the amounts and specific types of active ingredients in a dosage form may differ depending on factors such as, but not limited to, the route by which it is to be administered to patients.

5.8.1 Oral Dosage Forms

Pharmaceutical compositions that are suitable for oral administration can be provided as discrete dosage forms, such as, but not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, Remington's The Science and Practice of Pharmacy, 21st Ed., Lippincott Williams & Wilkins (2005).

Oral dosage forms provided herein are prepared by combining the active ingredients in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro-crystalline cellulose, diluents, granulating agents, lubricants, binders, and disintegrating agents.

In one embodiment, oral dosage forms are tablets or capsules, in which case solid excipients are employed. In another embodiment, tablets can be coated by standard aqueous or non-aqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free-flowing form such as powder or granules, optionally mixed with an excipient. Molded tablets can be made by molding in a suitable machine a mixture of the powdered compound moistened with an inert liquid diluent.

Examples of excipients that can be used in oral dosage forms provided herein include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Suitable forms of microcrystalline cellulose include, but are not limited to, the materials sold as AVICEL-PH-101, AVICEL-PH-103 AVICEL RC-581, AVICEL-PH-105 (available from FMC Corporation, American Viscose Division, Avicel Sales. Marcus Hook, PA), and mixtures thereof. A specific binder is a mixture of microcrystalline cellulose and sodium carboxymethyl cellulose sold as AVICEL RC-581. Suitable anhydrous or low moisture excipients or additives include AVICEL-PH-103™ and Starch 1500 LM. Other suitable forms of microcrystalline cellulose include, but are not limited to, silicified microcrystalline cellulose, such as the materials sold as PROSOLV 50, PROSOLV 90, PROSOLV HD90, PROSOLV 90 LM, and mixtures thereof.

Examples of fillers suitable for use in the pharmaceutical compositions and dosage forms provided herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions is, in one embodiment, present in from about 50 to about 99 weight percent of the pharmaceutical composition or dosage form.

In certain embodiments, fillers may include, but are not limited to block copolymers of ethylene oxide and propylene oxide. Such block copolymers may be sold as POLOXAMER or PLURONIC, and include, but are not limited to POLOXAMER 188 NF, POLOXAMER 237 NF, POLOXAMER 338 NF, POLOXAMER 437 NF, and mixtures thereof.

In certain embodiments, fillers may include, but are not limited to isomalt, lactose, lactitol, mannitol, sorbitol xytitol, crythritol, and mixtures thereof.

Disintegrants may be used in the compositions to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients may be used to form solid oral dosage forms. The amount of disintegrant used varies based upon the type of formulation, and is readily discernible to those of ordinary skill in the art. In one embodiment, pharmaceutical compositions comprise from about 0.5 to about 15 weight percent of disintegrant, or from about 1 to about 5 weight percent of disintegrant.

Disintegrants that can be used in pharmaceutical compositions and dosage forms include, but are not limited to, agar-agar, alginic acid, calcium carbonate, microcrystalline cellulose, croscarmellose sodium, povidone, crospovidone, polacrilin potassium, sodium starch glycolate, potato or tapioca starch, other starches, pre-gelatinized starch, other starches, clays, other algins, other celluloses, gums, and mixtures thereof.

Lubricants that can be used in pharmaceutical compositions and dosage forms include, but are not limited to, calcium stearate, magnesium stearate, mineral oil, light mineral oil, glycerin, sorbitol, mannitol, polyethylene glycol, other glycols, stearic acid, sodium stearyl fumarate, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL200, manufactured by W.R. Grace Co. of Baltimore, MD), a coagulated aerosol of synthetic silica (marketed by Degussa Co. of Plano, TX), CAB-O-SIL (a pyrogenic colloidal silicon dioxide product sold by Cabot Co. of Boston, MA), and mixtures thereof. If used at all, lubricants may be used in an amount of less than about 1 weight percent of the pharmaceutical compositions or dosage forms into which they are incorporated.

In certain embodiments, an oral dosage form comprises the compound, silicified microcrystalline cellulose, sodium starch glycolate, a block copolymer of ethylene oxide and propylene oxide, sodium stearyl fumarate and colloidal silicon dioxide. In certain embodiments, an oral dosage form comprises the compound in an amount of about 5% to about 75% by weight, silicified microcrystalline cellulose in an amount of about 15% to about 85%, sodium starch glycolate in an amount of about 2% to about 10%, block copolymer of ethylene oxide and propylene oxide in an amount of about 2% to about 10%, sodium stearyl fumarate in an amount of 0.2% to about 2%, and colloidal silicon dioxide in an amount of about 0.2% to about 2% by weight of the oral dosage form.

In certain embodiments, an oral dosage form comprises the compound, microcrystalline cellulose, isomalt, sodium starch glycolate, sodium lauryl sulfate, povidone, colloidal silicon dioxide, and magnesium stearate. In certain embodiments, an oral dosage form comprises the compound in an amount of about 40% to about 50%, microcrystalline cellulose in an amount of about 40% to about 50%, isomalt in an amount of 0% to about 5%, sodium starch glycolate in an amount of about 5% to about 10%, sodium lauryl sulfate in an amount of 0.2% to about 2%, povidone in an amount of about 2% to about 10%, colloidal silicon dioxide in an amount of 0.1% to about 1%, and magnesium stearate in an amount of about 0.1% to about 1% by weight of the oral dosage form.

In certain embodiments, provided herein are unit dosage forms that comprise between about 100 mg and about 1,200 mg, about 200 mg and about 1,000 mg, about 400 mg and about 800 mg, or about 450 mg and about 600 mg of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, {[5-(3-chlorophenyl)-3-hydroxypyridine-2-carbonyl]amino}acetic acid or 2-(5-(3-fluorophenyl)-3-hydroxypicolinamido)acetic acid).

In certain embodiments, provided herein are unit dosage forms that comprise about 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, 1,000 mg, 1,050 mg, 1,100 mg, 1,150, or even about 1,200 mg of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, {[5-(3-chlorophenyl)-3-hydroxypyridine-2-carbonyl]amino}acetic acid or 2-(5-(3-fluorophenyl)-3-hydroxypicolinamido)acetic acid). In certain embodiments, the unit dosage form comprises about 40 mg, about 120 mg, about 150 mg, about 185 mg, about 200 mg, about 250 mg, about 300 mg, or even about 315 mg of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, {[5-(3-chlorophenyl)-3-hydroxypyridine-2-carbonyl]amino}acetic acid or 2-(5-(3-fluorophenyl)-3-hydroxypicolinamido)acetic acid). In certain such embodiments, the unit dosage form is a capsule comprising about 40 mg, about 120 mg, about 185 mg, about 200 mg, about 200, about 250 mg, or even about 300 mg of the compound. In certain such embodiments, the unit dosage form is a tablet comprising about 150 mg of the compound. In certain such embodiments, the unit dosage form is a tablet comprising about 315 mg of the compound.

Liquid dosage forms for oral administration include pharmaceutically acceptable emulsions, microemulsions, solutions, suspensions, syrups, and elixirs. In addition to the active ingredient, the liquid dosage forms may contain inert diluents commonly used in the art, such as, for example, water or other solvents, solubilizing agents, and emulsifiers such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols, and fatty acid esters of sorbitan, and mixtures thereof.

Besides inert diluents, the oral compositions can also include adjuvants such as wetting agents, emulsifying and suspending agents, sweetening, flavoring, coloring, perfuming, and preservative agents.

Suspensions, in addition to the active inhibitor(s) may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Certain embodiments are illustrated by the following non-limiting examples.

6 EXAMPLES

6.1 Study Design

A phase 2b, randomized, double-blind, placebo-controlled study was developed to assess the hematologic pharmacodynamic response, safety, and tolerability of orally administered 5-(3-chlorophenyl)-3-hydroxypyridine-2-carbonyl]amino}acetic acid during dosing for 20 weeks in subjects with anemia secondary to CKD, Glomerular Filtration Rate (GFR) categories G3a-G5 (pre-dialysis). Only G5 patients not yet on dialysis are included in the study.

Subjects are assigned to a Study Group based on their ESA (erythropoiesis stimulating agent) status at Screening (Naïve, Previously Treated, or Actively Treated). Using a central randomization system, subjects are assigned in a double-blind fashion in a 2:1 ratio within each Study Group to either 5-(3-chlorophenyl)-3-hydroxypyridine-2-carbonyl] amino}acetic acid or placebo and initiate dosing at three (3) tablets of 150 mg each, once daily for a total dose of 450 mg administered orally once daily. Subjects will be randomized to maintain balance between placebo and 5-(3-chlorophenyl)-3-hydroxypyridine-2-carbonyl]amino}acetic acid treated subjects with respect to: 1) CKD status (GFR categories G3a/b, G4, or G5); and 2) whether or not they have diabetes mellitus.

Study medication is taken once daily on an outpatient basis for 20 consecutive weeks. Hemoglobin (HGB) is monitored at each study visit during dosing and is used to determine if the dose of study medication should be adjusted. Hemoglobin concentration (Hb) is reported as grams of hemoglobin per deciliter of blood (g/dL). Since red blood cells are approximately 33% hemoglobin, the hemoglobin concentration of whole blood normally is about one third of the hematocrit (HCT). Traditionally, hemoglobin is measured using the cyanmethemoglobin method, wherein a lysing agent is added to a sample of diluted blood. The lysing agent disrupts all the red cells in the sample and releases the hemoglobin into the fluid so that the sample is then a solution of hemoglobin. The hemoglobin is converted to a form called cyanomethemoglobin and the concentration is read by a spectrophotometer with the wavelength set at the peak absorbance of cyanomethemoglobin. The concentration of hemoglobin is then calculated from the optical density of the solution.

Alternatively, hemoglobin concentration may be determined using a HemoCue® device which can measure hemoglobin concentration in capillary, venous or arterial whole blood. The reaction in the HemoCue® cuvette is a modified azidemethemoglobin reaction. The erythrocyte membranes are disintegrated by sodium deoxycholate, releasing the hemoglobin. Sodium nitrite converts the hemoglobin iron from the ferrous to the ferric state to form methemoglobin, which then combines with azide to form azidmethemoglobin. The photometer uses a double wavelength measuring method, 570 nm and 880 nm, for compensation of turbidity.

Finally, hemoglobin concentration may be determined using a non-invasive method such as the Masimo Total Hemoglobin (SpHb®) which allows non-invasive and continuous monitoring of hemoglobin.

The dose is adjusted in accordance with the Dose Adjustment Guidelines (see below). Iron supplementation is prescribed as needed during the study to maintain ferritin levels of between 50 ng/mL and 300 ng/mL.

While the primary outcome of this study is HGB response, this study will also evaluate specified neurocognitive functioning and patient reported outcome (PRO) measures to assess the impact on cognition, depressed mood, and fatigue.

6.2 Evaluation of Neurocognitive and Patient Reported Outcome Measures

This study will include evaluations of specified neurocognitive and PRO measures to assess for the impact on cognition, depressed mood, and fatigue. Patients with anemia secondary to CKD experience a number of adverse symptoms that may be minimized and/or alleviated with efficacious treatment. These include symptoms of cognitive impairment, depressed mood, fatigue, and others.

6.3 Selection and Withdrawal of Subjects

Subjects are selected for the study based on the following inclusion and exclusion criteria.

Inclusion Criteria.

Subjects must meet all of the following inclusion criteria to be eligible;
1. 18 to 82 years of age, inclusive;
2. Diagnosis of Chronic Kidney Disease (per the Kidney Disease: Improving Global Outcomes 2012 Clinical Practice Guideline for the Evaluation and Management of Chronic Kidney Disease) with a GFR category of G3a-G5 that are not yet on dialysis and not expected to start dialysis within the study period;

3. Calculated estimated glomerular filtration rate (eGFR)≥10 and ≤65 mL/minute/1.73 m² at the Screening visit, (eGFR is calculated using the 2009 CKD-EPI creatinine equation);
4. Anemia secondary to CKD with an ESA status and a screening HGB that meet the criteria for one of the following groups
   Naïve (never received an ESA [Group 1]) with a HGB≤10.5 g/dL at Screening; OR
   Previously Treated (previously received ≥1 dose of ESA and have been off ESA therapy for ≥11 weeks at the time of Screening [Group 2]) with a HGB≤10.5 g/dL at Screening; OR
   Actively Treated (actively and consistently treated with an ESA for a minimum of 3 months prior to Screening, where the dose of ESA has not changed during the last two dose administrations and the prescribed ESA dosing interval is ≤4 weeks during the previous 3 months [Group 3]) with a HGB≥9.5 and ≤12 g/dL at Screening.). Subjects who do not fall into one of these three groups cannot be enrolled;
5. Ferritin ≥50 ng/mL with transferrin saturation (TSAT) ≥18%, or Ferritin ≥100 ng/mL with TSAT≥15%.
6. Understands the procedures and requirements of the study and provides written informed consent and authorization for protected health information disclosure.

Exclusion Criteria.

Subjects presenting with any of the following do not qualify for entry into the study:
1. Females who are pregnant or breast-feeding and women of child-bearing potential who are unable or unwilling to use an acceptable method of contraception;
2. Non-vasectomized male subjects who are unable or unwilling to use an acceptable method of contraception;
3. BMI>44.0 kg/m²;
4. Anemia due primarily to hemolysis (hemolytic anemia), active bleeding, or recent blood loss;
5. Red blood cell transfusion within 11 weeks prior to the Screening Visit, or anticipated need for transfusion during the study;
6. Androgen therapy within the previous 21 days prior to the Screening visit;
7. Intravenous iron within the past 4 weeks prior to the Screening visit;
8. Evidence of active infection, unless the medial monitor and Investigator agree that the subject is appropriate for this study;
9. History of chronic liver disease or evidence of liver dysfunction (aspartate transaminase (AST) or alanine transaminase (ALT)>1.8× upper limit of normal (ULN), alkaline phosphatase >2×ULN, or total bilirubin >1.5×ULN);
10. Screening electrocardiogram with QTc>500 msec (using Bazett's formula for the heart rate correction method);
11. Uncontrolled hypertension (diastolic blood pressure >110 mmHg or systolic blood pressure >190 mmHg at Screening;
12. New York Heart Association Class III or IV congestive heart failure;
13. Myocardial infarction, acute coronary syndrome, or stroke within 6 months prior to the Screening visit;
14. History of myelodysplastic syndrome or bone marrow fibrosis;
15. Subjects known to have diabetic gastroparesis that is either symptomatic on therapy or is refractory to therapy (diabetes itself does not exclude subjects from eligibility in the study);
16. Any history of active malignancy or treatment of malignancy in the previous 2 years except for curative resected basal cell carcinoma of skin, squamous cell carcinoma of skin, cervical carcinoma in situ, or resected benign colonic polyps;
17. History of systemic lupus erythematosus (SLE);
18. Age-related macular degeneration (AMD), diabetic macular edema, or active diabetic proliferative retinopathy that is likely to require treatment during the trial (disease itself is not exclusionary);
19. History of deep vein thrombosis (DVT) within previous 3 months requiring active treatment;
20. History of hemosiderosis;
21. History of prior or scheduled organ transplantation, or stem cell or bone marrow transplantation (corneal transplants are not excluded);
22. Use of an investigational medication or participation in an investigational study within 45 days or 5 half lives of the investigational medication, whichever is longer, preceding the Screening visit;
23. Previous participation in this study or previous receipt of 5-(3-chlorophenyl)-3-hydroxypyridine-2-carbonyl]amino}acetic acid in another clinical study or previous receipt of another HIF prolyl-hydroxylase inhibitor;
24. Other severe acute or chronic medical or psychiatric condition or laboratory abnormality that may increase the risk associated with study participation or study drug administration or may interfere with the interpretation of study results and in the Investigator's judgment, would make the subject inappropriate for study entry.

6.4 Treatment of Subjects

Subjects are assigned to a Study Group based on their ESA status at Screening (Naïve, Previously Treated, or Actively Treated). Subjects in Group 3 (Actively Treated) will have their ESA discontinued prior to randomization. Randomization and first dose of study medication should occur at approximately the same time that the subject would have otherwise received the next dose of their prior ESA therapy.

Subjects assigned to either 5-(3-chlorophenyl)-3-hydroxypyridine-2-carbonyl]amino}acetic acid or placebo will initiate dosing at three tablets (each 150 mg), once daily. Study medication will be taken once daily for 20 consecutive weeks.

HGB is monitored throughout the study to determine if the dose of study medication is adjusted or suspended. The dose is adjusted in accordance with the Dose Adjustment Guidelines. Dose changes are accomplished by changing the number of tablets to be taken per day, each tablet comprising 150 mg of Compound 1.

Investigators may prescribe iron supplementation as needed during the study to maintain Investigators should prescribe iron supplementation as needed during the study to maintain ferritin ≥50 ng/mL and ≤300 ng/mL. In general, only oral iron may be used for therapy and a minimum daily dose of 50 mg of elemental iron may be prescribed. Investigators are encouraged to prescribe iron supplementation when a subject's ferritin falls within the defined range (≥50 to ≤300 ng/mL) to prevent them from falling below the lower boundary of the range. Subjects with ferritin levels >300 ng/ml should not receive iron supplementation (oral or intravenous).

Subjects already receiving oral iron supplementation as part of their treatment plan may continue their current treatment regimen (as long as their ferritin is ≤300 ng/mL and they are receiving the therapeutic equivalent of a minimum daily dose of 50 mg elemental iron orally). Subjects already receiving oral iron supplementation as part of their treatment plan, but with a ferritin >300 ng/mL, should discontinue their current iron treatment regimen at the time of randomization.

Dosing of study medication should be suspended if HGB rises to ≥13.0 g/dL, and should not be restarted until HGB reduces to ≤12.5 g/dL. (Factors that may temporarily change the HGB level should be considered before suspending the dose.) HGB should be assessed every 2 weeks during this time period.

Once HGB has reduced to ≤12.5 g/dL, dosing of study medication is restarted as follows: 1) if subject had their dose reduced within the two week period prior to suspending the dosing, dosing will resume at the most recent dose level; or 2) if the subject had NOT had their dose reduced within the two week period prior to suspending the dosing, dosing will resume at a dose 150 mg lower than the last dose level taken by the subject.

Dose Adjustment Guidelines
1. Before any dose changes or dose suspensions are implemented, factors that may temporarily change the HGB level should be considered (e.g., fluid balance such as fluid overload or dehydration, infection, hospitalization, transfusion, missed doses, acute blood loss). Investigators have the option to delay dose adjustment by up to 7 days if it is suspected that temporary factors are the predominant cause of HGB change. The decision to defer or proceed with dose adjustment should be confirmed by a repeat HGB within 7 days (documented with a CBC performed through the central laboratory).
2. Dose should be adjusted based on the HGB measurement.
3. Decreases in dose are allowed at any time, for either tolerance or HGB.
4. Dose may be increased starting at Week 4 following the Dose Adjustment Guidelines (Table 1). The dose cannot be increased after the Week 12 visit. In general, only one dose adjustment should be made per four week period.
5. The dose of study medication should NOT be increased if the subject's HGB has increased by ≥1.2 g/dL from the pre-dose average.
6. Available dose levels include: 150 (1 tablet), 300 (2 tablets), 450 (3 tablets), and 600 (4 tablets) mg per day.
7. Dose adjustments will proceed based on the following criteria:

TABLE 1

Dose Adjustment Guidelines

| Change in HGB Since 4 Weeks Prior (g/dL) | HGB value (g/dL) at Present Visit | | | | |
|---|---|---|---|---|---|
| | <10.0 | 10.0 to 10.9 | 11.0 to 12.2 | 12.3 to 12.9 | ≥13.0 |
| ≤−0.5 | Increase 1 dose level* | Increase 1 dose level* | No change | No change | Stop drug and reevaluate†† |
| −0.4 to +0.4 | Increase 1 dose level* | No change ** | No change | Reduce 1 dose level† | Stop drug and reevaluate†† |
| +0.5 to +0.9 | No change | No change | No change | Reduce 1 dose level† | Stop drug and reevaluate†† |
| +1.0 to +1.4 | No change | No change | Reduce 1 dose level† | Reduce 2 dose levels† | Stop drug and reevaluate†† |
| ≥+1.5 | Reduce 1 dose level† | Reduce 1 dose level† | Reduce 2 dose levels† | Reduce 2 dose levels† | Stop drug and reevaluate†† |

*Dose of study medication should NOT be increased if the HGB has increased by ≥1.2 g/dL from the pre-dose average. The highest dose level is 600 mg per day. Subjects already on the highest dose level will continue on 600 mg per day. Dose cannot be increased after the Week 12 visit.
** For subjects with Baseline HGB ≥10.0 g/dL and their HGB hasn't increased by Week 8 or 12 by >0.4 g/dL compared to Baseline the investigator may increase the doses by one level.
†The lowest dose level is 150 mg per day. Subjects already on the lowest dose level will continue on 150 mg per day unless their HGB increases to ≥13.0 g/dL.
††Dosing will be suspended if HGB rises to ≥13.0 g/dL, and will not be restarted until HGB reduces to ≤12.5 g/dL. Factors that may temporarily change the HGB level should be considered before suspending the dose. HGB will be assessed every 2 weeks during this time period.

Optional ESA Rescue

Starting at Week 6, subjects will be allowed (although will not be required) to have their HGB rescued with ESA therapy. Subjects must meet the HGB criteria for ESA rescue in addition to having experienced a clinically significant worsening of their anemia or the symptoms of anemia. The criteria for initiating rescue therapy, and the target rescue HGB for the rescue therapy will be determined by the subjects' ESA status at Baseline. ESA rescue will be at the discretion of the investigator.

Investigators should use their local institution's ESA dosing guidelines for administering the rescue therapy. ESA therapy should be discontinued once the target rescue HGB is reached as listed in Table 2.

TABLE 2

HGB Criteria and Target Rescue HGB for Optional ESA Rescue Therapy

| ESA Status at Screening (HGB (g/dL)) | HGB (g/dL) Criteria for ESA Rescue* | Target Rescue HGB (g/dL) |
|---|---|---|
| Naïve | ≤9.0 | Baseline or 9.0, whichever is higher; maximum of 10.0 |
| Previously Treated | ≤9.0 | Baseline or 9.0, whichever is higher; maximum of 10.0 |
| Actively Treated | ≤9.4 | 10.0 |

Subjects receiving ESA rescue therapy should continue taking study medication. The dose of study medication should not be changed or adjusted at the start of or during ESA rescue therapy. The dose of study medication should be maintained throughout the ESA rescue therapy, unless the HGB rises to ≥13.0 g/dL. If the HGB rises to ≥13.0 g/dL, dosing of study medication and the ESA rescue therapy should be suspended. After completion of the ESA rescue, the study medication dose should continue to be adjusted as per the Dose Adjustment Guidelines.

6.5 Pharmaceutical Composition

6.5.1 40 mg, 200 mg, and 300 mg Capsule Formulations

Capsule formulations were prepared as follows:

| Material | Capsule, 40 mg | Capsule, 200 mg | Capsule 300 mg |
|---|---|---|---|
| Compound 1 (parent) | 40 mg | 200 mg | 300 mg |
| ProSolv® HD 90 | 464.5 mg | 224.8 mg | 124.8 mg |
| Explotab® sodium starch glycolate, NF | 28.5 mg | 24.0 mg | 24.0 mg |
| Poloxamer 188 NF | 28.5 mg | 24.0 mg | 24.0 mg |
| PRUV® | 5.7 mg | 4.8 mg | 4.8 mg |
| Cab-O-Sil M-5P | 2.85 mg | 2.40 mg | 2.40 mg |
| Total | 570 mg | 480.0 mg | 480.0 mg |

6.5.2 120 mg, 185 mg, 250 mg, and 315 Capsule Formulations

Capsule formulations were prepared as follows:

| Material | Capsule, 120 mg | Capsule, 185 mg | Capsule, 250 mg | Capsule, 315 mg |
|---|---|---|---|---|
| Compound 1 (parent) | 120.00 mg | 185.00 mg | 250.00 mg | 315.00 mg |
| ProSolv® HD 90 | 304.80 mg | 239.80 mg | 173.60 mg | 107.40 mg |
| Explotab® sodium starch glycolate, NF | 24.00 mg | 24.00 mg | 24.00 mg | 24.00 mg |
| Poloxamer 188 NF | 24.00 mg | 24.00 mg | 24.00 mg | 24.00 mg |
| PRUV® | 4.80 mg | 4.80 mg | 4.80 mg | 4.80 mg |
| Cab-O-Sil M-5P | 2.40 mg | 2.40 mg | 3.60 mg | 4.80 mg |
| Total | 480.00 mg | 480.00 mg | 480.00 mg | 480.00 mg |

6.5.3 150 mg Tablet Formulation

A tablet formulation was prepared as follows:

| Material | Excipient Grade | Quantity (mg) |
|---|---|---|
| Intra-granular Components | | |
| Compound 1 | — | 150.0 |
| Microcrystalline Cellulose, USP/NF | Avicel® PH105 | 158.4 |
| Isomalt, USP/NF | Galen IQ 801 | 9.53 |
| Explotab® sodium starch glycolate, NF | Explotab® | 10.70 |
| Sodium Lauryl Sulfate, NF | — | 3.57 |
| Povidone, USP/NF | Kollidon® 25 | 8.92 |
| Purified Water or Water for Injection, USP[1] | — | As required |
| Extra-granular Components | | |
| Explotab® sodium starch glycolate, NF | Explotab® | 14.28 |
| Colloidal Silicon Dioxide, NF | Cab-O-Sil | 0.89 |
| Magnesium Stearate, NF | Hyqual® 5712 | 0.71 |
| Total | | 357.0 |

Abbreviations: NF = National Formulary, USP = United States Pharmacopeia
[1]Removed during processing

6.5.4 315 mg Tablet Formulation

A 315 mg tablet formulation was prepared as follows using a wet granulation process:

| Material | Excipient Grade | Quantity (mg) |
|---|---|---|
| Intra-granular Components | | |
| Compound 1 (parent) | | 315.0 |
| Microcrystalline cellulose, USP/NF | Avicel® PH105 | 317.9 |
| Isomalt, USP/NF | Galen IQ 801 | 20.00 |
| Explotab® sodium starch glycolate, NF | Explotab® | 22.50 |
| Sodium lauryl sulfate, NF | | 7.500 |
| Povidone, USP/NF | Kollidon® 25 | 33.75 |
| Purified water for Injection, USP | | As required |
| Extra-granular Components | | |
| Explotab® sodium starch glycolate, NF | Explotab® | 30.00 |
| Colloidal Silicon Dioxide, NF | Cab-O-Sil | 1.875 |
| Magnesium Stearate, NF | Hyqual® 5712 | 1.5 |
| Total | | 750.0 |

6.5.5 Alternative 315 mg Tablet Formulation

A 315 mg tablet formulation may be prepared as follows using a wet granulation process:

| Material | Excipient Grade | Quantity (mg) |
|---|---|---|
| Intra-granular Components | | |
| Compound 1 (parent) | | 315.0 |
| Microcrystalline Cellulose, USP/NF | Avicel® PH105 | 317.9 |
| Explotab® sodium starch glycolate, NF | Explotab® | 22.50 |
| Sodium lauryl sulfate, NF | | 7.500 |
| Povidone, USP/NF | Kollidon® 25 | 33.75 |
| Purified water for Injection, USP | | As required |
| Extra-granular Components | | |
| Explotab® sodium starch glycolate, NF | Explotab® | 30.00 |
| Colloidal Silicon Dioxide, NF | Cab-O-Sil | 1.875 |
| Magnesium Stearate, NF | Hyqual® 5712 | 1.5 |
| Total | | 730.0 |

6.5.6 100 mg Tablet Formulation

A 100 mg tablet formulation may be prepared as follows using a wet granulation process:

| Material | Excipient Grade | Quantity (mg) |
|---|---|---|
| Intra-granular Components | | |
| Compound 1 | — | 100.0 |
| Microcrystalline Cellulose, USP/NF | Avicel® PH105 | 105 |
| Isomalt, USP/NF | Galen IQ 801 | 6.5 |
| Explotab® sodium starch glycolate, NF | Explotab® | 7.1 |

-continued

| Material | Excipient Grade | Quantity (mg) |
|---|---|---|
| Sodium Lauryl Sulfate, NF | — | 2.4 |
| Povidone, USP/NF | Kollidon® 25 | 5.9 |
| Purified Water or Water for Injection, USP[1] | — | As required |
| Extra-granular Components | | |
| Explotab® sodium starch glycolate, NF | Explotab® | 9.5 |
| Colloidal Silicon Dioxide, NF | Cab-O-Sil | 0.6 |
| Magnesium Stearate, NF | Hyqual® 5712 | 0.5 |
| Total | | 237.5 |

Abbreviations: NF = National Formulary, USP = United States Pharmacopeia
[1]Removed during processing

6.5.7 250 mg Tablet Formulation

A 250 mg tablet formulation may be prepared as follows using a wet granulation process:

| Material | Excipient Grade | Quantity (mg) |
|---|---|---|
| Intra-granular Components | | |
| Compound 1 | — | 250.0 |
| Microcrystalline Cellulose, USP/NF | Avicel® PH105 | 263 |
| Isomalt, USP/NF | Galen IQ 801 | 15.8 |
| Explotab® sodium starch glycolate, NF | Explotab® | 17.8 |
| Sodium Lauryl Sulfate, NF | — | 5.9 |
| Povidone, USP/NF | Kollidon® 25 | 16.0 |
| Purified Water or Water for Injection, USP[1] | — | As required |
| Extra-granular Components | | |
| Explotab® sodium starch glycolate, NF | Explotab® | 23.8 |
| Colloidal Silicon Dioxide, NF | Cab-O-Sil | 1.5 |
| Magnesium Stearate, NF | Hyqual® 5712 | 1.2 |
| Total | | 595.0 |

Abbreviations: NF = National Formulary, USP = United States Pharmacopeia
[1]Removed during processing

6.6 Diurnal Cycle of EPO

Clinical data obtained to date indicate that Compound 1 stimulates modest dose-proportional daily increases in EPO levels in a manner similar to the physiologic diurnal response, without increasing baseline EPO. Throughout these studies, Compound 1 has demonstrated a clear and consistent dose response pattern in both pharmacokinetics and pharmacodynamics with sequential increases in EPO, reticulocytes, and HGB. The hematologic response has been accompanied by dose responsive changes in iron-related parameters, with decreases in hepcidin and ferritin, and an increase in total iron binding capacity (TIBC). This combination of changes indicates that Compound 1 increases hematopoiesis through a coordinated response. Furthermore, this is achieved with a modest increase in the daily peak level of EPO, but with no increase in basal (pre-dose) levels (in a manner that mimics the physiologic diurnal response in healthy individuals).

6.6.1 Phase I Studies

In the Phase 1 studies, the rise in EPO was proportionate to the dose of Compound 1 administered. In the Phase 1a single ascending dose (SAD) study, significant, dose-dependent rises at 8, 12, 18, and 24 hours following dosing were observed (FIG. 1) in the 900 and 1200 mg groups when compared to placebo (p<0.01). In addition, the 600 mg cohort had a significant increase at 8 hours (p=0.034).

A similar response was observed in the Phase 1b multiple ascending dose (MAD) study. The peak EPO concentration demonstrated a dose responsive increase. Regardless of the dosing group, the EPO concentration essentially returned to baseline prior to the next morning dose, thus maintaining the diurnal response pattern. On Day 7, the placebo group had a similar EPO) response profile to the 500 mg group, again possibly driven by blood loss from phlebotomy during the study (approximately 230 mL from Day −1 through Day 8).

6.6.2 Phase IIa Studies

Figure 1B:
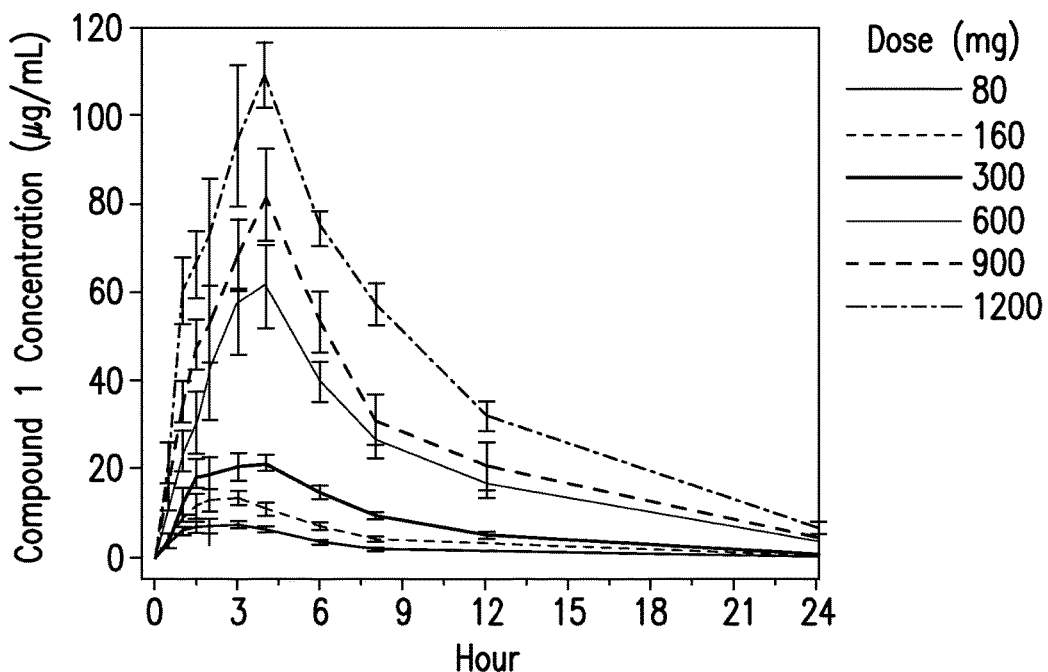
FIG. 1b shows the EPO response in healthy male adults over twenty-four hours after administration of Compound 1.
Figure 2:
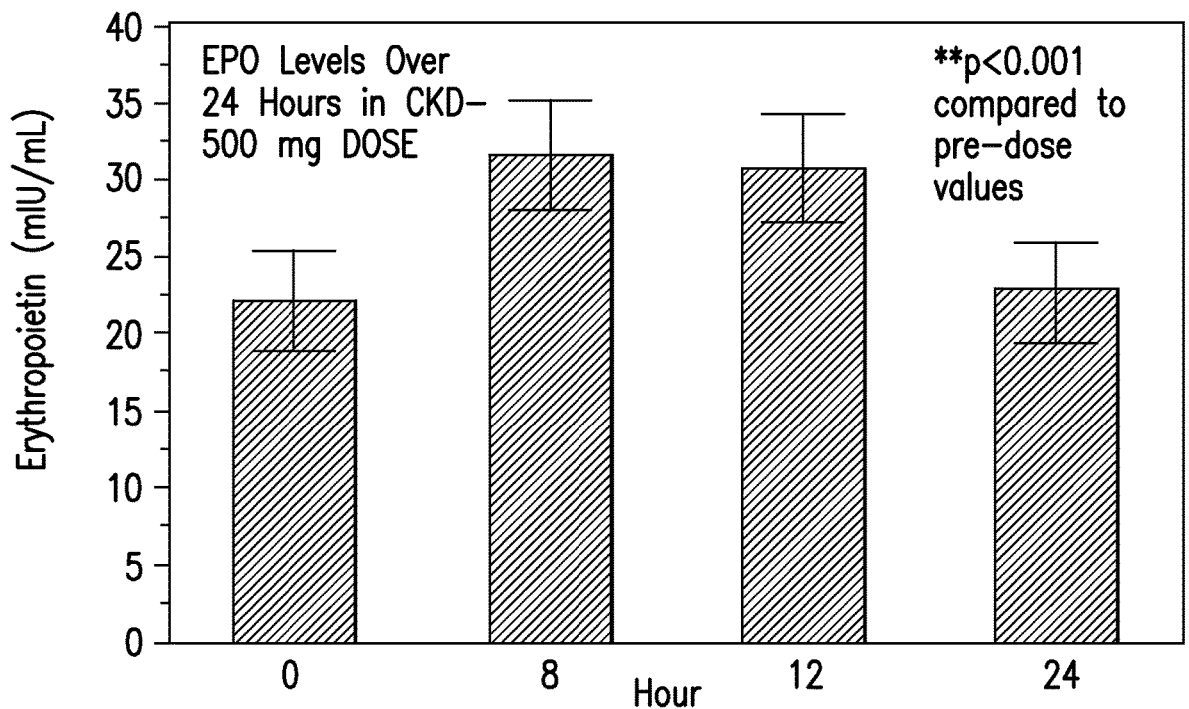
FIG. 2 shows the EPO levels over twenty four hours in patients with anemia secondary to chronic kidney disease after administration of Compound 1.
Figure 3:
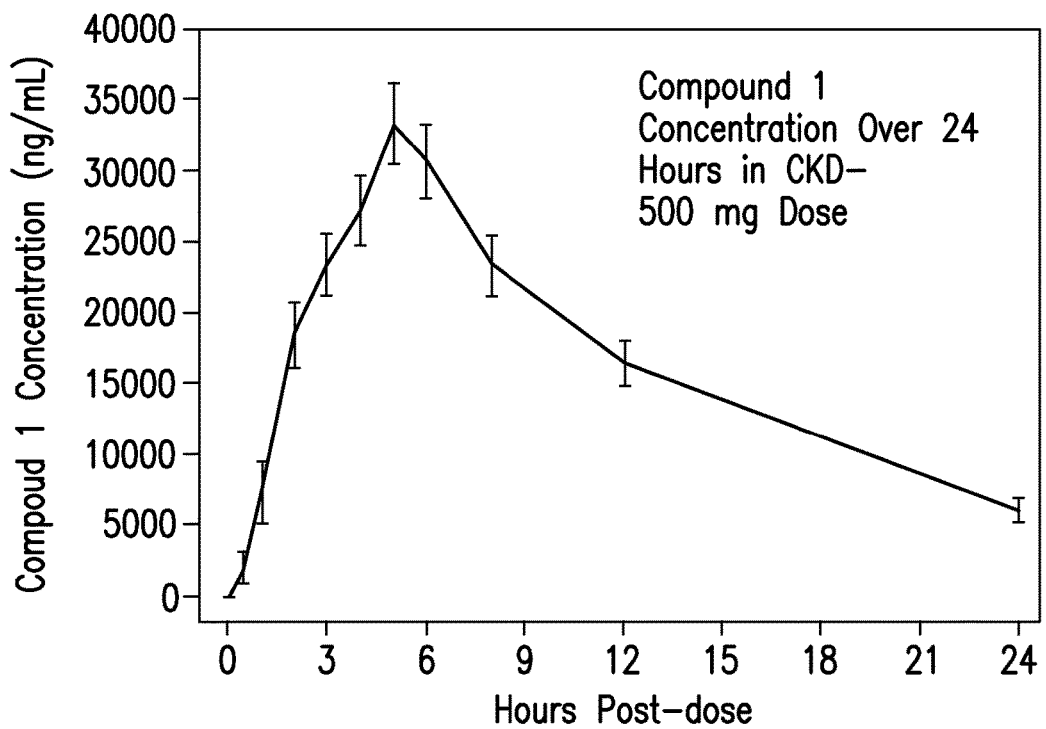
FIG. 3 shows the concentration of Compound 1 in patients with anemia secondary to chronic kidney disease over twenty-four hours.
Figure 4:
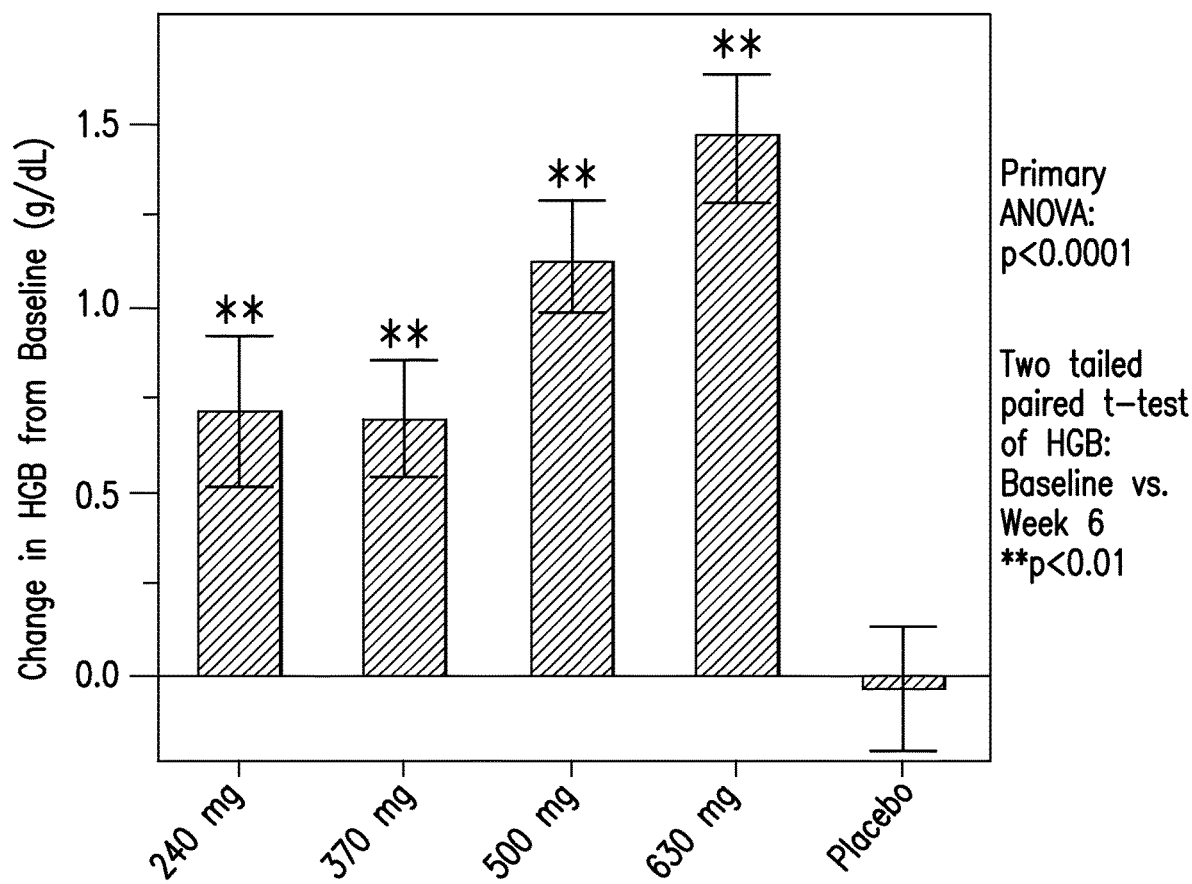
FIG. 4 shows the change in hemoglobin from baseline in patients with anemia secondary to chronic kidney disease when Compound 1 is administered at various doses.
Figure 5:
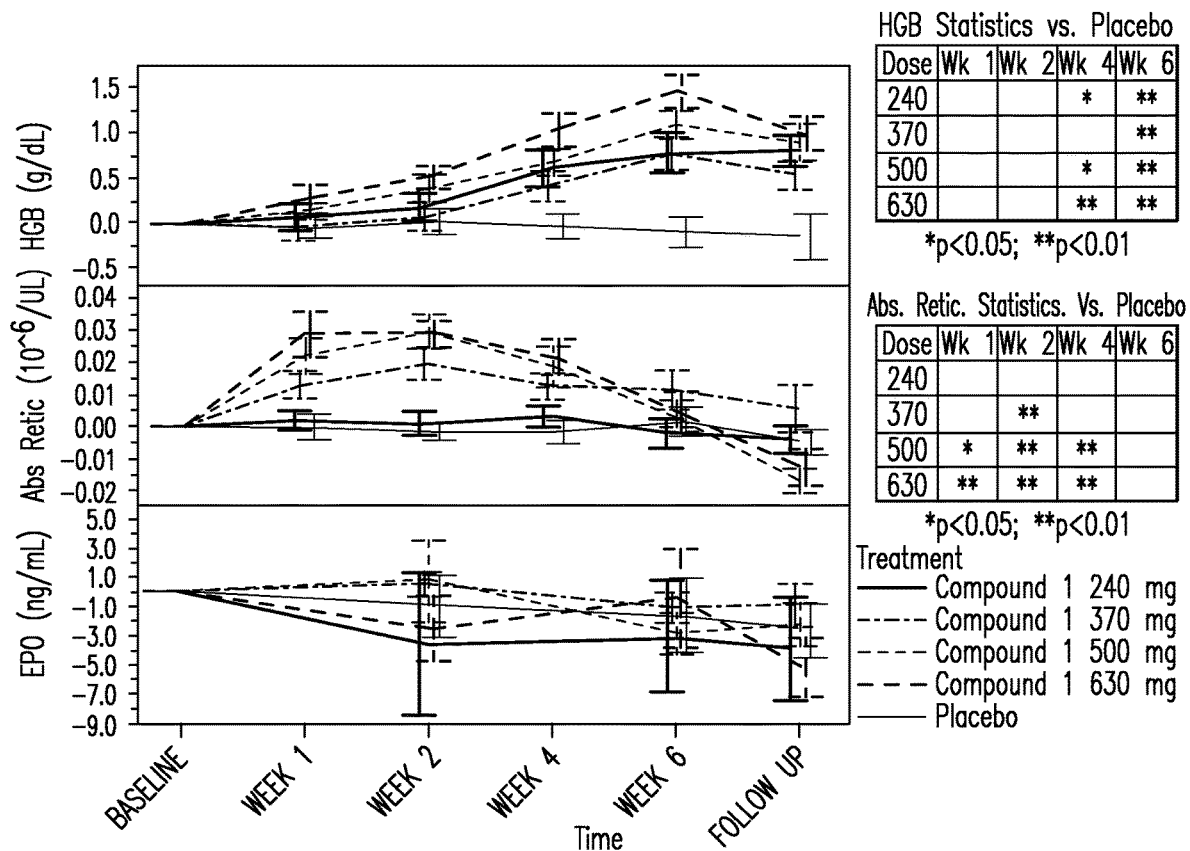
FIG. 5 shows the hemoglobin, reticulocyte, and EPO levels in patients with anemia secondary to chronic kidney disease over six weeks of treatment with Compound 1.

Current treatment of anemia associated with chronic kidney disease (CKD) with erythropoiesis-stimulating agents (ESAs) can lead to supraphysiological levels of circulating erythropoietin (EPO) that persist for days, a profile that may be associated with increased cardiovascular side effects and thromboembolic events. Compound 1, administered at a dose of 500 mg in patients having anemia secondary to CKD were shown to return to baseline EPO levels within 24 hours (FIG. 2). This is true, despite the fact that the half-life of Compound 1 in patients with anemia secondary to CKD is significantly longer (FIG. 3) as compared to the half-life of healthy individuals (FIG. 1b). Compound 1, was shown to induce moderate daily increases in EPO levels in CKD patients, mimicking the physiologic diurnal response in healthy individuals. In a randomized double-blind, placebo-controlled Phase 2a trial, 93 patients with CKD stage 3, 4, or 5 (not on dialysis) received placebo or Compound 1 in the following dose groups: 240, 370, 500, or 630 mg once daily for 6 weeks. At Week 6, Compound 1 significantly increased HGB compared to baseline in all dose groups and compared to placebo (ANOVA, p<0.0001) as shown in FIG. 5. The HGB increase occurred without increasing basal (pre-dose) EPO levels (prior to daily Compound 1 dose). Results at Week 6 also revealed a dose-related increase in total iron binding capacity and a decrease in hepcidin, suggesting enhanced iron mobilization. There was a clear dose-responsive increase in HGB starting from the lowest dose as shown in FIG. 4. Erythropoictin was measured at baseline, week 2, end of treatment and follow up. As shown in FIG. 5, hemoglobin levels increased over time, while serum levels of EPO did not increase significantly over time. Thus, Compound 1 significantly increases HGB in anemic CKD patients by inducing moderate daily increases in EPO levels in a manner similar to the physiologic diurnal response and by enhancing iron mobilization.

Figure 6:
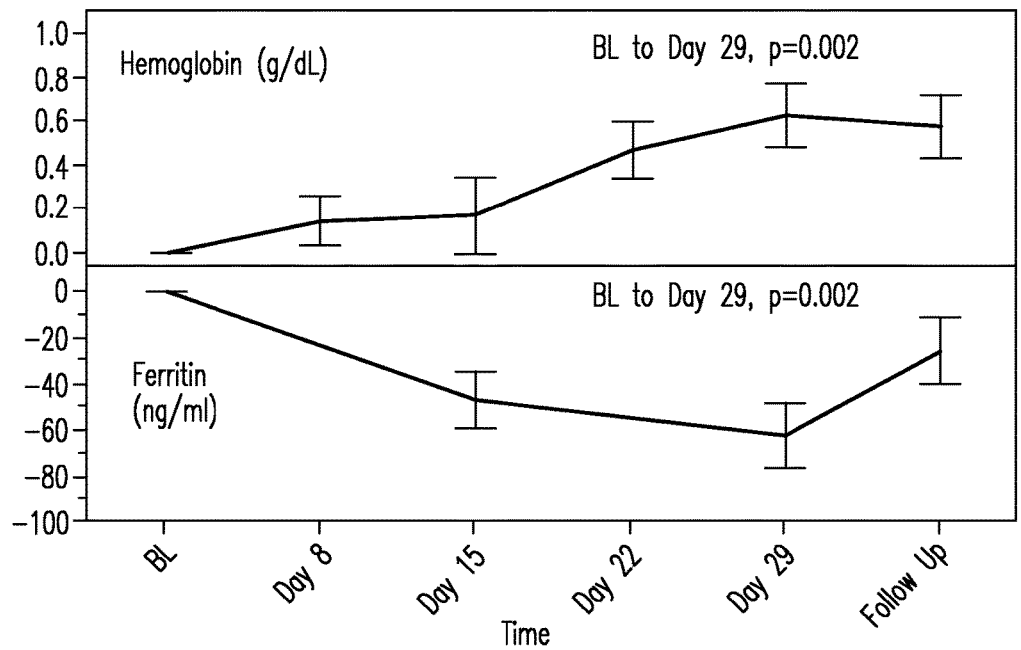
FIG. 6 shows the mean (±SE) absolute change from the mean baseline for hemoglobin and ferritin in a dose escalation study in patients with anemia secondary to chronic kidney disease.

In a Phase 2a dose escalation study, 10 CKD patients received Compound 1 once daily for 28 days. Dosing began at 400 mg in CKD Stage 3 patients and 300 mg in CKD Stage 4 patients. The dose was increased by 100 mg for each week that absolute reticulocyte count (ARC) did not increase by 18,000 above the baseline (BL) average. Results, including both Stage 3 and 4 CKD patients, demonstrated that hemoglobin rose from 9.91 g/dL at BL to 10.54 g/dL by Day 29. Ferritin decreased from 334.10 ng/mL at BL to 271.70 ng/mL by Day 29, indicating that Compound 1 is well-tolerated and increases hemoglobin while decreasing ferritin in a dose-dependent manner in patients with Stage 3 or 4 CKD. The consistent rise in hemoglobin and the concurrent fall in ferritin over the course of the study suggest an efficacious daily dose of Compound 1 begins between 300 and 400 mg. FIG. 6 shows the mean (±SE) absolute change from the mean baseline for hemoglobin and ferritin.

6.7 Total Iron Binding Capacity

Figure 7:
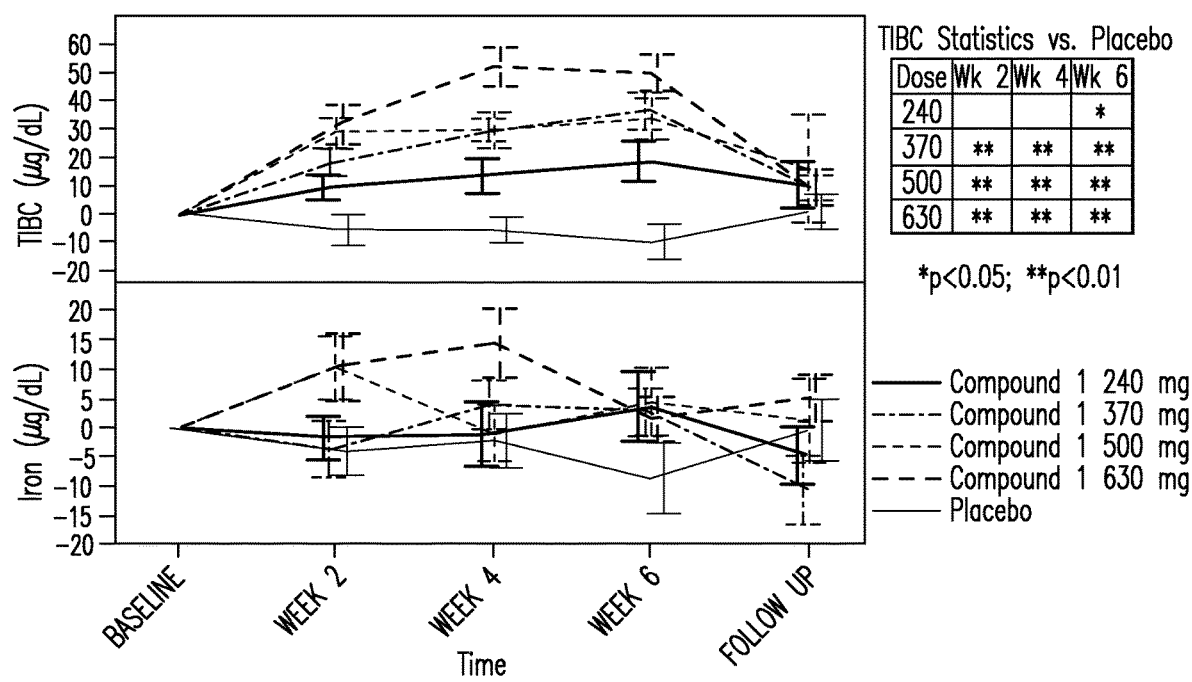
FIG. 7 shows an increase in total iron binding capacity in patients with anemia secondary to chronic kidney disease over six weeks, while also showing no significant increase in serum iron levels when treated with Compound 1.

In a randomized double-blind, placebo-controlled Phase 2a clinical trial, 93 patients with CKD stage 3, 4, or 5 (not on dialysis) received placebo or Compound 1 in the following dose groups: 240, 370, 500, or 630 mg once daily for 6 weeks. At Week 6, Compound 1 significantly increased TIBC compared to baseline in all dose groups and compared to placebo (ANOVA, p<0.0001) as shown in FIG. 7. The TIBC increase occurred without increasing serum iron levels (relative to baseline). Results at Week 6 also revealed a dose-related increase in TIBC and a decrease in TSAT, due to lack of increase in serum iron level, suggesting enhanced iron mobilization. TIBC and serum iron levels were measured at baseline, week 2, week 4, end of treatment (week 6) and follow up.

6.8 Hepcidin Expression

Figure 8:
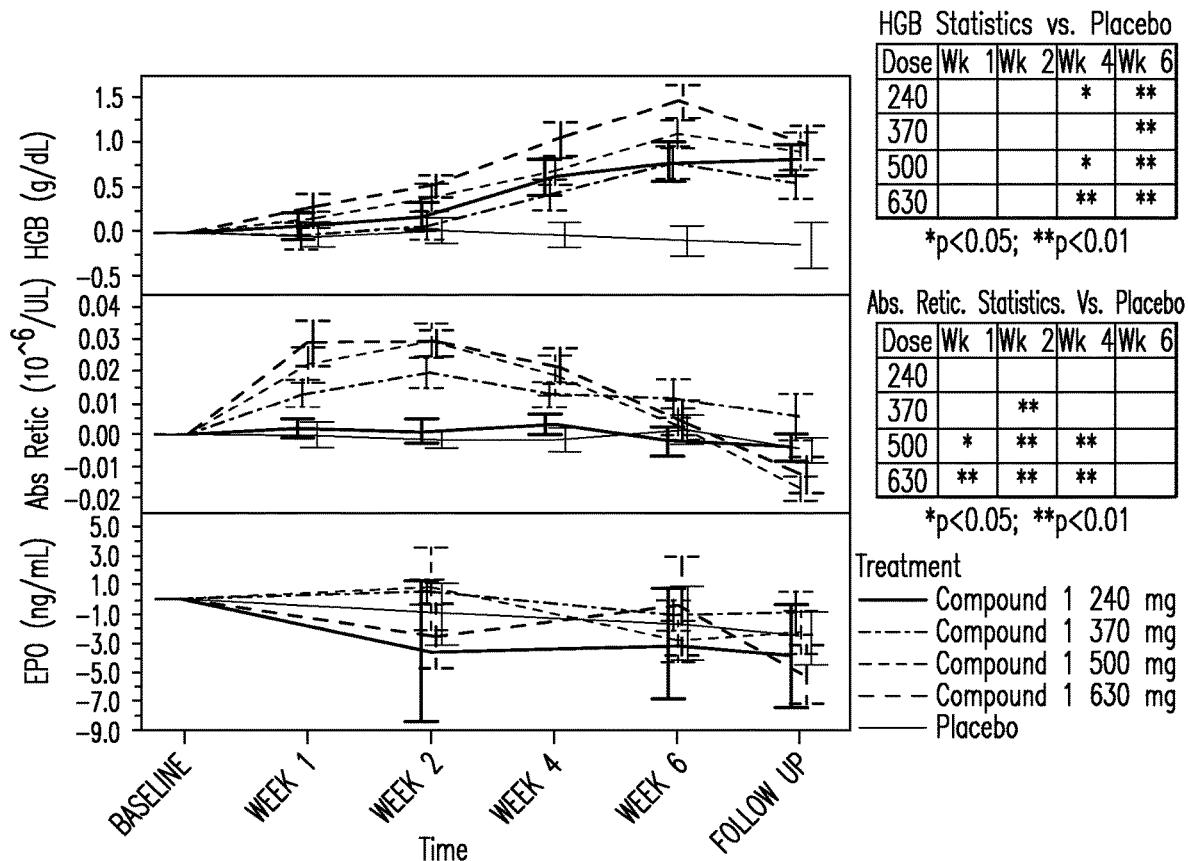
FIG. 8 shows an increase in serum hemoglobin levels relative to baseline in patients with anemia secondary to chronic kidney disease over six weeks when treated with Compound 1.
Figure 9:
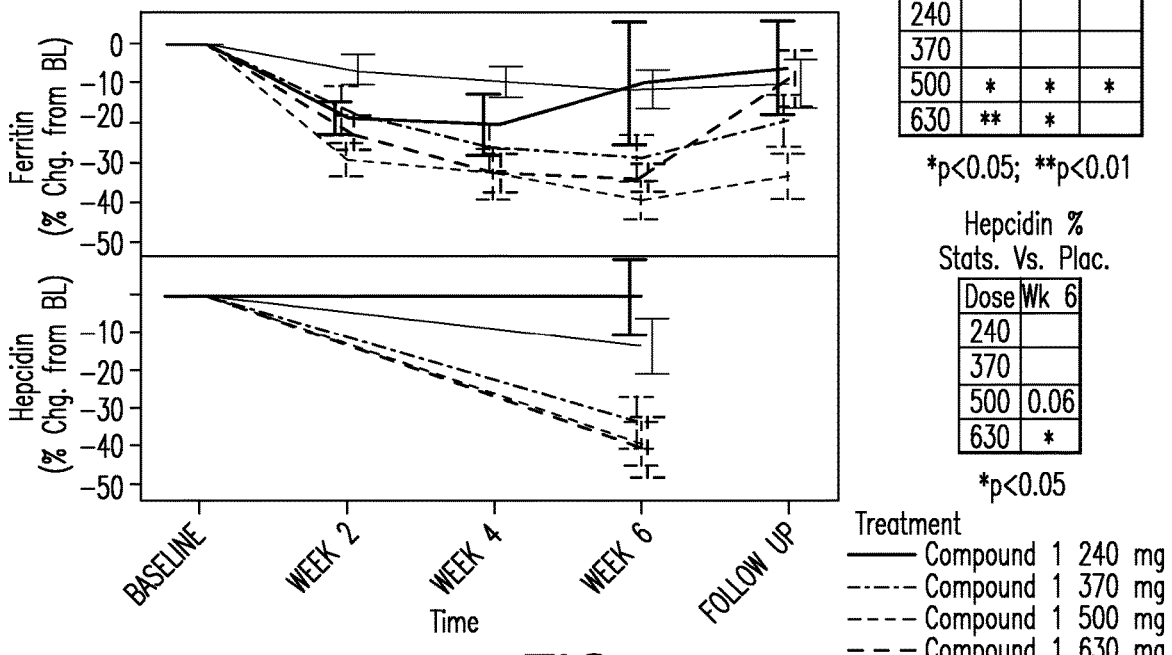
FIG. 9 shows that at low doses, hepcidin expression does not decrease relative to baseline in patients with anemia secondary to chronic kidney disease over six weeks when treated with Compound 1.

In a randomized double-blind, placebo-controlled Phase 2a trial, 93 patients with CKD stage 3, 4, or 5 (not on dialysis) received placebo or Compound 1 in the following dose groups: 240, 370, 500, or 630 mg once daily for 6 weeks. At Week 6, Compound 1 significantly increased hemoglobin levels compared to baseline in all dose groups and compared to placebo (ANOVA, p<0.0001) as shown in FIG. 8. Significantly, at low doses of Compounds 1, such as the 240 mg group, the increase in serum hemoglobin was not accompanied by a decrease in hepcidin expression, as shown in FIG. 9.

6.9
N-(2-aminoethyl)-3-hydroxy-pyridine-2-carboxamide 6.9.1 Procedures
EGLN-1 Activity Assay:
The EGLN-1 (or EGLN-3) enzyme activity is determined using mass spectrometry (matrix-assisted laser desorption ionization, time-of-flight MS, MALDI-TOF MS—for assay details, see reference (Greis et al., 2006)). Recombinant human EGLN-1-179/426 is prepared as described above and in the Supplemental Data. Full-length recombinant human EGLN-3 is prepared in a similar way; however it is necessary to use the His-MBP-TVMV-EGLN-3 fusion for the assay due to the instability of the cleaved protein. For both enzymes, the HIF-1α peptide corresponding to residues 556-574 (DLDLEALAPYIPADDDFQL) is used as substrate. The reaction is conducted in a total volume of 50 uL containing TrisCl (5 mM, pH 7.5), ascorbate (120 μM), 2-oxoglutarate (3.2 μM), HIF-1α (8.6 μM), and bovine serum albumin (0.01%). The enzyme, quantity predetermined to hydroxylate 20% of substrate in 20 minutes, is added to start the reaction. Where inhibitors are used, compounds are prepared in dimethyl sulfoxide at 10-fold final assay concentration. After 20 minutes at room temperature, the reaction is stopped by transferring 10 μL of reaction mixture to 50 μL of a mass spectrometry matrix solution (α-cyano-4-hydroxycinnamic acid, 5 mg/mL in 50% acetonitrile/0.1% TFA; 5 mM NH$_4$PO$_4$). Two microliters of the mixture are spotted onto a MALDI-TOF MS target plate for analysis with an Applied Biosystems (Foster City, CA) 4700 Proteomics Analyzer MALDI-TOF MS equipped with a Nd:YAG laser (355 nm, 3 ns pulse width, 200 Hz repetition rate). Hydroxylated peptide product is identified from substrate by the gain of 16 Da. Data defined as percent conversion of substrate to product is analyzed in GraphPad Prism 4 to calculate IC$_{50}$ values.

VEGF ELISA Assay:
HEK293 cells are seeded in 96-well poly-lysine coated plates at 20,000 cells per well in DMEM (10% FBS, 1% NEAA, 0.1% glutamine). Following overnight incubation, the cells are washed with 100 uL of Opti-MEM (Gibco, Carlsbad, CA) to remove serum. Compound 13 in DMSO is serially diluted (beginning with 100 μM) in Opti-MEM and added to the cells. The conditioned media is analyzed for VEGF with a Quantikine human VEGF immunoassay kit (R&D Systems, Minneapolis, MN). Optical density measurements at 450 nm are recorded using the Spectra Max 250 (Molecular Devices, Sunnyvale, CA). Data defined as % of DFO stimulation is used to calculate EC$_{50}$ values with GraphPad Prism 4 software (San Diego, CA).

Mouse Ischemic Hindlimb Study:
All animal work is conducted in accordance with the Guide for the Care and Use of Laboratory Animals (National Academy of Sciences; Copyright ©1996) and the Institutional Animal Care and Use Committee guidelines at Procter and Gamble Pharmaceuticals. Nine to ten week old male C57Bl/6 mice from Charles River Laboratory (Portage, MI) are used for study. The mice are orally dosed with vehicle (aqueous carbonate buffer, 50 mM; pH 9.0) or Compound 13 in vehicle at 50 mg/kg or 100 mg/kg. The animals are dosed three times: day 1 at 8 am and 5 pm, day 2 at 8 am. One hour after the first dose, unilateral arterial ligation is performed under anesthesia using isoflurane. The femoral artery is ligated proximal to the origin of the popliteal artery. The contralateral limb can undergo a sham surgical procedure. Ligation is performed in an alternating fashion between right and left hindlimbs. Two hours after gam dosing on day 2, blood is obtained by ventricular stick while the mice are anesthetized with isoflurane. Serum samples for EPO analysis are obtained using gel clot serum separation tubes. Heart, liver, and gastroenemius muscles are harvested, snap-frozen in liquid nitrogen, and stored in −80° C. until use.

Mouse Serum EPO Assay:
The mouse serum EPO is detected using Mouse Quantikine Erythropoietin ELISA kit from R&D Systems according to manufacturer's instructions.

Mouse Tissue HIF Western Blot Analysis:
Tissues from mice stored at −80° C. are powdered with mortar and pestle chilled with liquid nitrogen. Nuclear extracts are prepared using an NE-PER kit (Pierce Biotechnology). For immunoprecipitation, nuclear extract is added to monoclonal antibody to HIF-1α (Novus, Littleton, CO) at a tissue to antibody ratio of 200:1. The suspension is incubated in a conical micro centrifuge tube for 4 hours at 4° C. Protein A/G-coupled agarose beads (40 ul of a 50% suspension) are then added to the tube. Following overnight tumbling at 4° C., the beads are washed 3 times with ice-cold phosphate buffered saline. The beads are then prepared for SDS-PAGE with 40 ul of Laemmli sample buffer. Proteins separated on SDS-PAGE are transferred onto nitrocellulose sheets with XCell-II Blot Module system (Invitrogen, Carlsbad, CA). The blots are blocked with 5% BSA prior to incubation with a rabbit antibody to HIF-1α at 1:100 dilution (Novus). The blots can then be washed with Tris-buffered saline/Tween-20 buffer and incubated with horseradish peroxidase-conjugated goat anti-rabbit secondary antibody (Pierce, Rockford, IL). Blots are developed with the ECL reagent (Amersham, Piscataway, NJ). Images of blots are captured with an Epson Expression 1600 scanner.

6.9.2 Experimental Analysis of Putative HIF Prolyl Hydroxylase Inhibitors
Study Objective:
To assess the activity of putative hypoxia inducible factor (HIF) Prolyl Hydroxylase Inhibitors to inhibit HIF prolyl hydroxylase enzyme activity and thereby to stabilize HIF (HRE luciferase activation) and increase EPO production (EPO immunoassay) in a human cell line (Hep3B cells).

Materials and Methods:

Cell Culture: Human hepatocellular carcinoma (Hep3B) cells were obtained from the American Type Culture Collection (ATCC, Mannassas, VA) and cultured according to ATCC recommendations. Cells were cultured at 37° C. in an atmosphere of 95% air and 5% $CO_2$ in a humidified incubator. Compound 13 was diluted to a stock concentration of 50 mM in DMSO (Sigma).

Cell Treatments:

Hep3B cells were plated on 24 well plates. Subsets of Hep3B cultures were transfected with a HIF reporter plasmid (pHRE-luciferase) overnight. (See Sheta, et al., Oncogene. 2001 Nov. 15:20(52):7624-34.) Cells were exposed to vehicle (1:1000 DMSO) or test Compound 13 at 50 μm for 18 hours at 37° C. in an atmosphere of 95% air and 5% $CO_2$ in a humidified incubator.

Analysis:

After 48-hour culture, cell supernatants were subsequently collected, centrifuged at 15,000×g for 15 minutes at 4° C. to sediment debris.

In Vitro EPO Induction Assay:

Secreted EPO levels were assayed by specific immunoassay (MesoScale Discovery, Gaithersburg, MD) in accordance with manufacturer's instructions.

In Vitro HIF Prolyl Hydroxylase Inhibition Assay:

Cell lysates were assayed using the dual luciferase reporter-assay (Promega, Madison, WI, USA). Observed firefly luciferase activity was normalized to a co-transfected *Renilla* luciferase.

Study Results:

Compound 13 was tested for its ability to inhibit HIF prolyl hydroxylase enzyme activity and thereby to stabilize HIF (HRE luciferase activation) and increase EPO production (EPO immunoassay) in vitro in a human cell line (Hep3B cells) as compared to DMSO vehicle as a negative control. Compound 13 was assayed in duplicate. Fold change over the vehicle control was calculated. Compound 13 was tested at a concentration of 50 μm. A compound is considered inactive if it has ≤1.0 fold activity over control. Resulting values for the In Vitro EPO Induction Assay, and In Vitro HIF Prolyl Hydroxylase Inhibition Assay are shown in Table 1 and Table 2. Surprisingly, Compound 13 was found to both inhibit HIF prolyl hydroxylase enzyme activity and increase EPO production.

TABLE 1

In Vitro EPO Induction Assay

| Sample | Mean [EPO] (mIU/mL) | Standard Deviation | Fold Change |
|---|---|---|---|
| Vehicle | 3.0736 | 0.059382 | 1 |
| Compound 13 | 8.9137 | 0.76616 | 2.9001 |

TABLE 2

In Vitro HIF Prolyl Hydroxylase Inhibition Assay

| Sample | Mean HIF PH Inhibition Activity (Relative Luciferase) | Standard Deviation | Fold Change |
|---|---|---|---|
| Vehicle | 1 | 0.21 | 1 |
| Compound 13 | 3.6 | 1.01 | 3.6 |

While particular embodiments of the present disclosure have been illustrated and described, it would be obvious to those skilled in the art that various other changes and modifications can be made without departing from the spirit and scope of the disclosure. It is therefore intended to cover in the appended claims all such changes and modifications that are within the scope of this disclosure.

The invention claimed is:

1. A method for treating anemia secondary to or associated with chronic kidney disease, comprising orally administering to a patient having said anemia an effective amount of a compound which is {[5-(3-chlorophenyl)-3-hydroxypyridine-2-carbonyl]amino}acetic acid having the structure, Compound 1

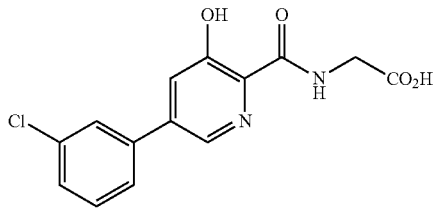

or a pharmaceutically acceptable salt thereof, wherein a daily dose comprises 150±30 mg, 300±30 mg, 450±30 mg, 600±30 mg, or 750±30 mg of the compound.

2. The method of claim 1, wherein the compound is a pharmaceutically acceptable salt of {[5-(3-chlorophenyl)-3-hydroxypyridine-2-carbonyl]amino}acetic acid.

3. The method of claim 1, wherein the compound is {[5-(3-chlorophenyl)-3-hydroxypyridine-2-carbonyl]amino}acetic acid.

4. The method of claim 1, wherein the chronic kidney disease is stage 3, 4, or 5 chronic kidney disease.

5. The method of claim 1, wherein the chronic kidney disease is pre-dialysis chronic kidney disease.

6. The method of claim 1, wherein the daily dose is administered orally, once daily.

7. The method of claim 1, wherein the patient has not been previously treated for anemia.

8. The method of claim 1, where the patient is refractory to treatment with recombinant erythropoietin.

9. The method of claim 1, wherein the patient has been previously treated for anemia.

10. The method of claim 1, wherein hemoglobin levels of the patient
   a. are maintained at a level of at least about 9.0 g/dL and at or below about 13.0 g/dL; or
   b. are maintained at a level of at least about 10.0 g/dL and at or below about 13.0 g/dL; or
   c. are maintained at a level of at least about 11.0 g/dL and at or below about 13.0 g/dL; or
   d. are increased by at least about 1.2 g/dL relative to a baseline hemoglobin level.

11. The method of claim 10 wherein the hemoglobin levels are tested at least about 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, or about 8 weeks after the initial administering of the compound.

12. The method of claim 1, wherein the compound is administered in combination with another medicament.

13. The method of claim 12, wherein the other medicament is an iron supplement.

14. The method of claim 13, wherein the iron supplement is administered at least two hours following administration of the compound.

15. The method of claim 13, wherein the iron supplement is administered in an amount such that ferritin is maintained at a level of between about 50 ng/mL and about 300 ng/mL.

16. The method of claim 13, wherein the iron supplement is administered orally at a daily dose about 50 mg of elemental iron.

17. The method of claim 13, wherein the iron supplement is administered (i) on an as needed basis; (ii) continuously; and/or (iii) indefinitely.

18. The method of claim 1, wherein the compound is administered once a day every day during treatment at the same time of the day.

19. The method of claim 18, wherein the time of day is in the morning or 2 pm.

20. The method of claim 1, further comprising
taking a first measurement of the hemoglobin level in the patient and subsequently taking a second measurement of the hemoglobin level in the patient, wherein
i. if the hemoglobin level in the patient at the second measurement is less than about 10.0 g/dL and the level of hemoglobin has increased by less than about 0.5 g/dL as compared to the level at the first measurement; or
ii. if the hemoglobin level in the patient at the second measurement is less than about 10.0 g/dL and the level of hemoglobin has changed by up to about 0.4 g/dL as compared to the level at the first measurement; or
iii. if the hemoglobin level in the patient at the second measurement is between about 10.0 and about 10.9 g/dL and the level of hemoglobin has decreased by less than about 0.5 g/dL as compared to the level at the first measurement; then
administering an adjusted daily dose of the compound that is greater than the initial daily dose.

21. The method of claim 1, further comprising
taking a first measurement of the hemoglobin level in the patient and subsequently taking a second measurement of the hemoglobin level in the patient, wherein
i. if the hemoglobin level in the patient at the second measurement is less than about 10.0 g/dL and the level of hemoglobin has increased by greater than about 1.5 g/dL as compared to the level at the first measurement; or
ii. if the hemoglobin level in the patient at the second measurement is between about 10.0 and about 10.9 g/dL and the level of hemoglobin has increased by greater than about 1.5 g/dL as compared to the level at the first measurement; or
iii. if the hemoglobin level in the patient at the second measurement is between about 11.0 and about 12.2 g/dL and the level of hemoglobin has increased by between about 1.0 and about 1.4 g/dL as compared to the level at the first measurement; or
iv. if the hemoglobin level in the patient at the second measurement is between about 12.3 and about 12.9 g/dL and the level of hemoglobin has decreased by up to about 0.4 g/dL or increased by up to about 0.4 g/dL as compared to the at the first measurement; or
v. if the hemoglobin level in the patient at the second measurement is between about 12.3 and about 12.9 g/dL and the level of hemoglobin has increased by about 0.5 to about 0.9 g/dL as compared to the level at the first measurement; then
administering an adjusted daily dose of the compound that is less than the initial daily dose.

22. The method of claim 1, further comprising
taking a first measurement of the hemoglobin level in the patient and subsequently taking a second measurement of the hemoglobin level in the patient, wherein
i. if the hemoglobin level in the patient at the second measurement is between about 11.0 and about 12.2 g/dL and the level of hemoglobin has increased by greater than about 1.5 g/dL as compared to the level at the first measurement; or
ii. if the hemoglobin level in the patient at the second measurement is between about 12.3 and about 12.9 g/dL and the level of hemoglobin has increased by between about 1.0 and about 1.4 g/dL as compared to the level at the first measurement; or
iii. if the hemoglobin level in the patient at the second measurement is between about 12.3 and about 12.9 g/dL and the level of hemoglobin has increased by greater than between about 1.5 g/dL as compared to the level at the first measurement; then
administering an adjusted daily dose of the compound that is less than the initial daily dose.

23. The method of claim 1, wherein the patient has predialysis chronic kidney disease.

24. The method of claim 1, wherein the patient is a dialysis patient.

25. The method of claim 1, wherein the daily dose is administered as two tablets, each comprising 150 mg of the compound.

26. The method of claim 20, wherein the adjusted daily dose of the compound is about 150 mg greater than the initial daily dose.

27. The method of claim 20, wherein the adjusted daily dose of the compound is 600 mg.

28. The method of claim 21, wherein the adjusted daily dose of the compound is about 150 mg less than the initial daily dose.

29. The method of claim 22, wherein the adjusted daily dose of the compound is about 150 mg less than the initial daily dose.

30. The method of claim 1, wherein a daily dose comprises 300±30 mg of the compound.

\* \* \* \* \*